(12) United States Patent
Felden

(10) Patent No.: US 7,858,316 B2
(45) Date of Patent: Dec. 28, 2010

(54) EUBACTERIAL TMRNA SEQUENCES AND USES THEREOF

(75) Inventor: Brice Felden, Le Lou du Lac (FR)

(73) Assignee: University of Utah Research Foundation, Salt Lake City, UT (US)

( * ) Notice: Subject to any disclaimer, the term of this patent is extended or adjusted under 35 U.S.C. 154(b) by 238 days.

(21) Appl. No.: 12/163,512

(22) Filed: Jun. 27, 2008

(65) Prior Publication Data

US 2009/0104607 A1    Apr. 23, 2009

Related U.S. Application Data

(62) Division of application No. 11/329,230, filed on Jan. 11, 2006, now Pat. No. 7,611,843, which is a division of application No. 09/958,206, filed as application No. PCT/US00/08988 on Apr. 6, 2000, now Pat. No. 7,115,366.

(60) Provisional application No. 60/128,058, filed on Apr. 7, 1999.

(51) Int. Cl.
*C12Q 1/68* (2006.01)
*A01N 43/04* (2006.01)
*A61K 31/70* (2006.01)
*C07H 21/02* (2006.01)
*C07H 21/04* (2006.01)
*C12P 19/34* (2006.01)

(52) U.S. Cl. .................. 435/6; 435/91.1; 435/91.2; 514/44 R; 536/23.1; 536/23.7

(58) Field of Classification Search ...................... None
See application file for complete search history.

(56) References Cited

U.S. PATENT DOCUMENTS 5,861,245 A * 1/1999 McClelland et al. ........... 435/6

OTHER PUBLICATIONS

Himmelreich et al. (Nucleic Acids Res. 24 (22), 4420-4449; 1996).*
B. Felden et al., "Eubacterial tmRNAs: everywhere except the alpha-Proteobacteria?" Biochimica et Biophysica Acta 1446:145-148, 1999.
N. Nameki et al., "Three of four pseudoknots in tmRNA are interchangeable and are substitutable with single-stranded RNAs," FEBS Lett 470(3):345-349, Mar. 31, 2000.
N. Nameki et al., "Functional and structural analysis of a pseudoknot upstream of the tag-encoded sequence in E. coli tmRNA," J. Mol. Biol 286(3):733-744, Feb. 26, 1999.
W. Schönhuber et al., "Utilization of tmRNA squences for bacterial identification,".MBC Microbiology 2001, 1:20 (online, 8 pages).
K.P. Williams et al., "Phylogenetic analysis of tmRNA secondary structure," RNA 2:1306-1310, 1996.
C. Zwieb et al., "Survey and Summary, Comparative sequence analysis of tmRNA," Nucleic Acids Research 27(10):2063-2071, 1999.
Huang, C. et al., "Charged tmRNA but not tmRNA-mediated proteolysis is essential for Neisseria gonorrhoeae viability," The EMBO Journal, vol. 19, No. 5, pp. 1098-1107, 2000, copyright European Molecular Biology Organization.
Ley, B.E. et al., "Eubacterial approach to the diagnosis of bacterial infection," Archives of Disease in Childhood 1997;77:148-149.
NCBI Sequence Revision History, Accession No. AE000035, http://www.ncbi.nlm.nih.gov/sviewer/girevhist.cgi?val=AE000035, printed Jun. 8, 2010, 25 pages.
NCBI Sequence Revision History, Accession No. AE000045, http://www.ncbi.nlm.nih.gov/sviewer/girevhist.cgi?val=AE000045, printed Jun 8, 2010, 20 pages.

* cited by examiner

*Primary Examiner*—Janet Epps-Smith
(74) *Attorney, Agent, or Firm*—Rothwell, Figg, Ernst & Manbeck p.c.

(57) ABSTRACT

The present invention is directed to eubacterial tmDNA sequences and the corresponding tmRNA sequences. The present invention is further directed to alignments of eubacterial tmDNA sequences and the use of the sequences and sequence alignments for the development of antibacterial drugs. The present invention is also directed to the use of the sequences for the development of diagnostic assays.

6 Claims, 24 Drawing Sheets

```
                     ┌─CODING SEQUENCE                                          H4
                     │                                                         ┌──────┐
Tab.saccha  AUAAAC│gcaaacgauaau--------------uuagcuuacgcugcuUAA│UA-CAAGCAGC---
C.acetobut  ******│************--------------******************│***********---
C.stercora  AUAAAC│gcaaacaacgauaacuac--------gcuuuagcugcugcgUAA│GUAACACGCAGCC--
C.perfrige  AUAAAC│gcagaagauaau--------------uuugcauuagcagcuUAA│UUUAGCGCUGCU---
C.lentocel  GUAAAC│gcugaagauaau--------------uuagcaaucgcugccUAA│UA-AGGC-GC----
Hlb.mobili  UUAAUU│gccgaagauaac--------------uacgcuuuagcugcuUUA│UUGCAGUCUAA----
Hsp.gestii  UUAAUU│gccgaagauaac--------------uacgcuuuagcugcuUUA│UUGCAGUCUAA----
Bb.brevis   UUAACU│ggcaacaaacaa--------------cuuucucucgcugcuUAA│UAACCAGUGAG----
B.subtilis  AUAACU│ggcaaaacuaacaguuuuaaccaaaacguagcauuagcugcCUAA│UAAGCGCAGCGA---
B.badius    AUAACU│ggcaaaaagau--------------uuagcuuuagcugcCUAA│UAUAGGUUCAGCU--
B.megateri  AUAACU│ggcaaaucuaacaauaac--------uucgcuuuagcugcaUAA│UAGUAGCUUAGC---
B.thermole  AUAACU│ggcaaacaaaac--------------uacgcuuuagcugcCUAA│UUGCUGCAGCUA---
Eco.fecium  AUAACU│gcuaaaaacgaaaacaacucu------uacgcuuuagcugcCUAA│AAA-CAGUUAGCGUA
Eco.faecal  AUAACU│gcuaaaaacgaaaacaauucu------uucgcuuuagcugcCUAA│AAACCAGCUAGCGAA
Stc.pyogen  AUAACU│gcaaaaauacaaacucu---------uacgcuuuagcugcCUAA│AAACCAGCUAGCGU-
Stc.pneumo  AUAACU│gcaaaaauaacacuucu---------uacgcucuagcugcCUAA│AAACCAGCAGGCGU-
Stc.gordon  AUAACU│gcaaaaauaauacuucu---------uacgcuuuagcugcCUAA│AAACCAGCGGGCGU-
Stc.mutans  AUAACU│gcaaaaauacaaauucu---------uacgcaguagcugcCUAA│AAACCAGCCUGUGU-
Stp.epider  AUAACU│gacaaaucaaacaauaau---------uucgcaguagcugcgUAA│UAGCCACUGC-----
Stp.aureus  AUAACU│ggcaaaucaaacaauaau---------uucgcaguagcugcCUAA│UCGCA-CU-CUGC--
L.acidophi  AUAACU│gcaaauaacaaaaauucu---------uacgcauuagcugcuUAA│UUUAGCGCAUGCGU- Tab.saccha  CGUUCAA-CCUU-UGAU-UCCCAC--AUCA-AAGGAUUGGGCGUCG--AUUUAGUGGGG
C.acetobut  ********-********--*AAUCUGGCGUCG----AGAGCGGGG
C.stercora  CGUCGG-C-CCCCGGGGUUCCUGC---GCCUCGGGAUACCGGCGUCA---UCAAGGCAGG
C.perfrige  CAUCCUU--CCU-CAAUUGCCCACG-GUUG-AGAGUAAGGGUGUCAUUUAAAAGUGGGG
C.lentocel  AGUCCU----CCU-AGGUCUUCCGCA-GCCU-AGAUC-AGGGCUUCG---ACUCGCGGAU
Hlb.mobili  CCUCUU-C-UCC-UC-UGUGCUCUCGGUGA-GGAUGUAAGGGGUCA-UUUAAGAGAGCU
Hsp.gestii  CCUCUU-C-UCC-UC-UGUGCUCUCGGUGA-GGAUGUAAGGGGUCA-UUUAAGAGAGCU
Bb.brevis   GCUCUC-CCACU-GCAUCGGCCCGU-GUGC-CGUGGAUAGGGCUCAACUUUAACGGGCU
B.subtilis  GCUCUUC--CUG-ACAU-UGCCUAU-GUGU-CUGU-GAAGAGCACA-UCCAAGUAGGCU
B.badius    GCUCCU--CCCG-CUAU-CGUCCAU-GUAGUCGGGUAAGGGGUCCAAACUUAGUGGACU
B.megateri  GUUCCU--CCCU-CCAU-CGCCCAU-GUGGUAGGGUAAGGGACUCACUUUAAGUGGGCU
B.thermole  GCUCCUC--CCG-CCAU-CGCCCGC-GUGG-CGUUCGAGGGGCUCAUAUGGAGCGGGCU
Eco.fecium  GAUCCU--CUCG-GCAU-CGCCCAU-GUGCUCGAGUAAGGGUCUCAAAUUUAGUGGGAU
Eco.faecal  GAUCCU--CCCG-GCAU-CGCCCAU-GUGCUCGGGUCAGGGUCUAAUCGAAGUGGGAU
Stc.pyogen  GACUUCU--ACA-AGAU-UGCUUGU-GUCC-UGUU-AGAAGUC-UCAAAUAGCAAGCU
Stc.pneumo  GACCC---GAUUU-GGAU-UGCUCGU-GUUC-AAUGA-CAGGUCUUAUUAUUAGCGAGAU
Stc.gordon  GACCC---GAUUC-GGAU-UGCUUGU-GUCU-GAUGA-CAGGUCUUAUUAUUAGCAAGCU
Stc.mutans  GAUCAAU--AAC-AAAU-UGCUUGU-GUUU-GUUG-AUUGGUCUUAUUGUUAACAAGCU
Stp.epider  AUCGCC-UAACA-GCAU-CUCCUAC-GUGC-UGUUAACGCGAUUCAACCCUAGUAGGAU
Stp.aureus  AUCGCC-UAACA-GCAU-UUCCUAU-GUGC-UGUUAACGCGAUUCAACCUUAAUAGGAU
L.acidophi  UGCUCU-UUGUC-GGUU-UACUCGU-GGCU-GACAC-UGAGUAUCA-ACUUAGCGAGUU
                           └────┐          ┌─────┐         ┌─────┐
                                └──────────┘     └─────────┘
                                              PK2
```

FIG. 3B

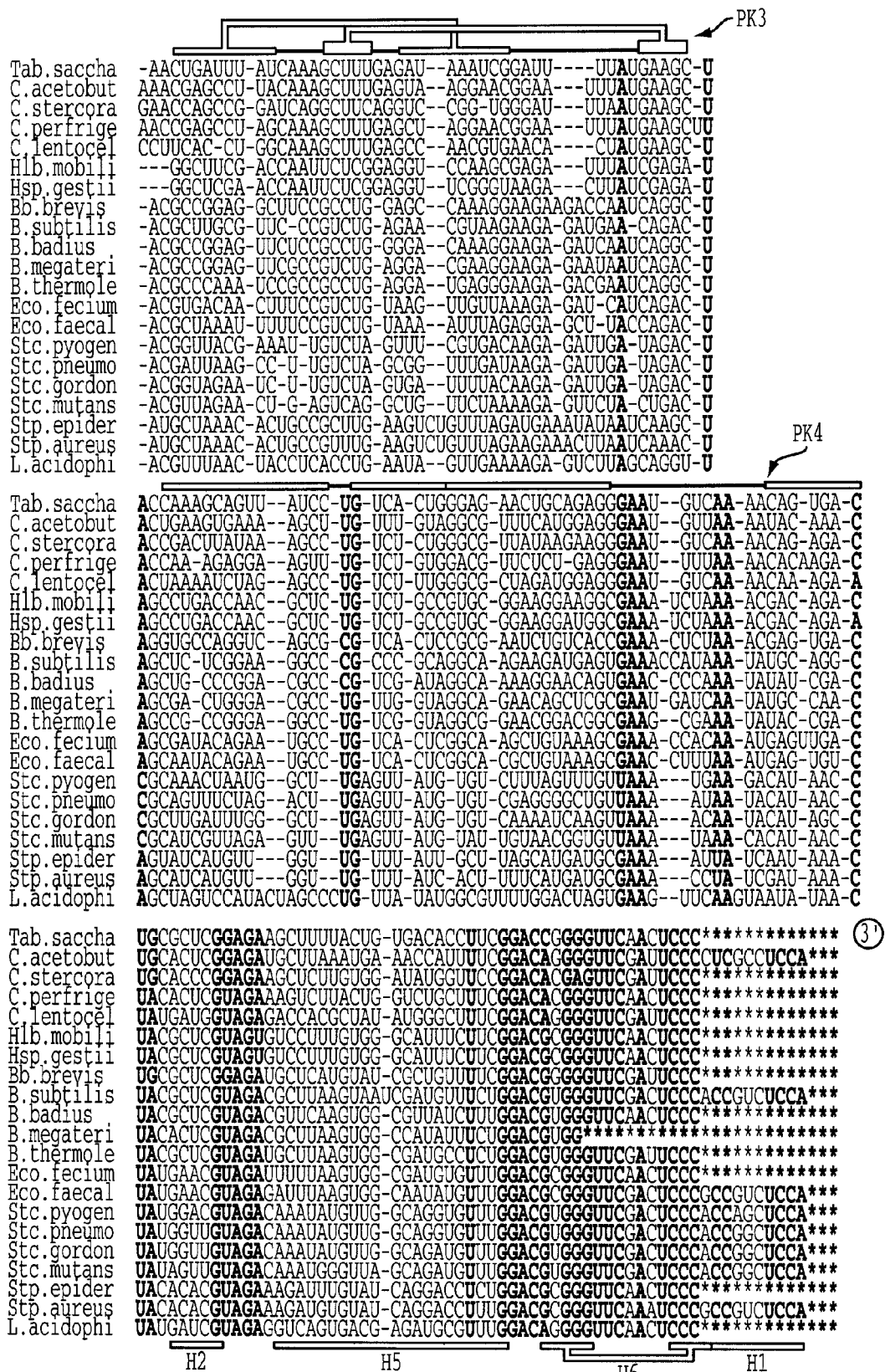
FIG. 3C  +RNA-LIKE DOMAIN H1-H6

```
Aqf.aeolic  CG-GGCUACUCGGU--CGCACGGG-GCUGAGUAGCUGACACCUAACCCGUGCU ⎫
Tt.maritim  A--CCGAUUCAG--UUCGCCUUCCGGCCUGAAUCGGGAAAACUCAGGAAGGCU ⎪
Tt.neapoli  A--CCGAUCUGGGCUCCGCCUUCCGGCCCGGAUCGGGAAGGUUCAGGAAGGCU ⎪
T.thermoph  A--GCCCGGGGC--CACGCCCUCU--AACCCCGGGCGAAGCUUGAAGGGGGCU ⎪
D.radiodur  A--GCCC-AGGC--GAUUCUCCAU--AGCCGACGGCGAAACU-UUAUGGAGCU ⎪
D.proteoly  A--GCUU-AGGU--GAGGUUCCAU--AGCCAAAAGUGAAACC-AAAUGGAAAU ⎬ PK3
Tmc.roseum  GCCCCUGGCCCA--AGCGCCGGUG---CGGGCCAGGUCAAGCGUGAUCCGGCU ⎪
Ctb.proteo  GC-UCUUAAGCAG--UGGCACCAG--CUGUUUAAGGGUGAAAAGAGUGGUGCU ⎪
Her.aurant  CGCUCCCCUAGUU--AUGUCUGUG--GGCUAGGGG--CUAAGAUUAACAGGCU ⎪
Tdb.commun  UU-GGGAGGCUUAA-UCGGUGGGG--UUAAGCCUCCCGAGAUUACAUCCCACCU ⎪
Ver.spinos  G--GCCAAAAGAGC-GGGCGACCG-GC-CCCAAGGCGAGAUCUACAGGCCGCU ⎪
Dcg.thermo  GCCCCUUCCG-----ACUCCCCUA-----AGGAAGGGAAAGA-UGUAGGGGAU ⎭
            ══════════════    ══════════════    ════════════

Aqf.aeolic  A--CCCUC-GGGGAGCUUGCCCGUGGGCGACCC-GAGGG--GAAAUCC-UGAACACGGGC ⎫
Tt.maritim  G-UGGGAGAGGACACCCUGCCCGUGGGAGGUCC-CUCCC--GAGACG-AAAACACGGGC ⎪
Tt.neapoli  G-UGGGAAGCGACACCCUGCCCGUGGGGGUC-CUUCCC--GAGACAC-GAAACACGGGC ⎪
T.thermoph  C-GCUCCUGGCC--GCCCGUCCGCGGGCCAAGCCAGGAG--GACACGC-GAAACGCGGAC ⎪
D.radiodur  A-CGGCCUGCGAGAACCUGCCCACUGGUGAGCGCCGGCCC-GACAAUC-AAACAGUGGGA ⎪
D.proteoly  A-AGGCGGACGGCAGCCUGUUUGCUGGCAGCCCAGGCCC--GACAAUU-UAAGAGCAGAC ⎬ PK4
Tmc.roseum  C-GGCUGACCGGGAUCCUGUCGGUGGGAGCCUGG-CAGC--GACAGUA--GAACACCGAC ⎪
Ctb.proteo  G--GGCAGUGCGGUU--GGGCU-UCCUGGGCUGCACUGUC-GAGACUU-CACAGGAGGGC ⎪
Her.aurant  G-GUCGUGGC-CCGCUUUGUCUAUCGGGUGGUGCACCGAU-AAGAUUU-AAUCAAUAGAC ⎪
Tdb.commun  G--GUAGGGUUGCUGGGUGCCUGUGACAAGCA-CCCUAC--GAGAUUU--UCCCACAGGC ⎪
Ver.spinos  G--GAUGGACGGCAUCCUGGCAGUAGGAGGCUGGACAUC--GAGAUCA--AAUNAUUGCC ⎪
Dcg.thermo  AGGUGCUUACAGAAUCCUGCGGGAGGGAGUCUGUAAGUGCCGAAAAGUUAAAACUCCCGC ⎭
            ═══════════════════════════════════════════════

Aqf.aeolic  UAAGCC-UGUAGAGCCUCGGAUGUGGCCGCCGUCCUCGGACGCGGGUUCGAUUCCCGCCGCCUCCACCA
Tt.maritim  UGCGCU-CGGAGAAGCCCAGGGG---CCUCCAUCUUCGGACGGGGGUUCGAAUCCCCCCGCCUCCACCA
Tt.neapoli  UGCGCU-CGGAGAAGCCCAGGGG---CCUCCAUCUUCGGACGGGGGUUCGAUUCCCGCCGCCUCCA***
T.thermoph  UACGCG-CGUAGAGGCcacgccc---cggcgaccuucggacgggggUUCGAUUCCCCCCaccuccacca
D.radiodur  UACACA-CGUAGACGCA-CGCUG--GACGGACCUUUGGACGGCGGGUUCGACUCCGCCCACCUCCACCA
D.proteoly  UACGCA-CGUAGAUGCA-CGCUG--GAUGGACCUUUGGACGGCGGGUUCGAUUCCCGCCGCCU-CACCA
Tmc.roseum  UAAGCC-UGUAGCAUAUCCUCGG---CUGAACGCUCUGGACGGGGGGUUCAACUCCCGCCAGCUCCACCA
Ctb.proteo  UAAGCC-UGUAGACGCGAAAGGU---GGCGGCUCGUCGGACGCGGGUUCGAUUCCCGCCGCCUCCACCA
Her.aurant  UACGCU-UGUAGAUGCUUGCGGU----UUAACUUUUUGGACGCGGGUUCGAUUCCCGCCGCCUCCACCA
Tdb.commun  UAAGCC-UGUAGCGGUUUAAUCU---GAACUAUCUCCGGACGCGGGUUCGAUUCCCGCCGCCUCCACCA
Ver.spinos  UGAGCA-UGGAGACGCUUUCAUA-----AAGGNGUUCGGACAGGG*****************
Dcg.thermo  UAAGCU-UGUAGAGGCUUUUGAU---UCUUGCUCUCUGGACGCGGGUUCGAUUCCCGCCGCCUCCACCA ③'
             ═════      ═════════           ════════           ═════      ═════
              H2          H5                   H6                        H1
                                             ═══════════════════════
                                             +RNA-LIKE DOMAIN H1-H6
```

FIG. 4B

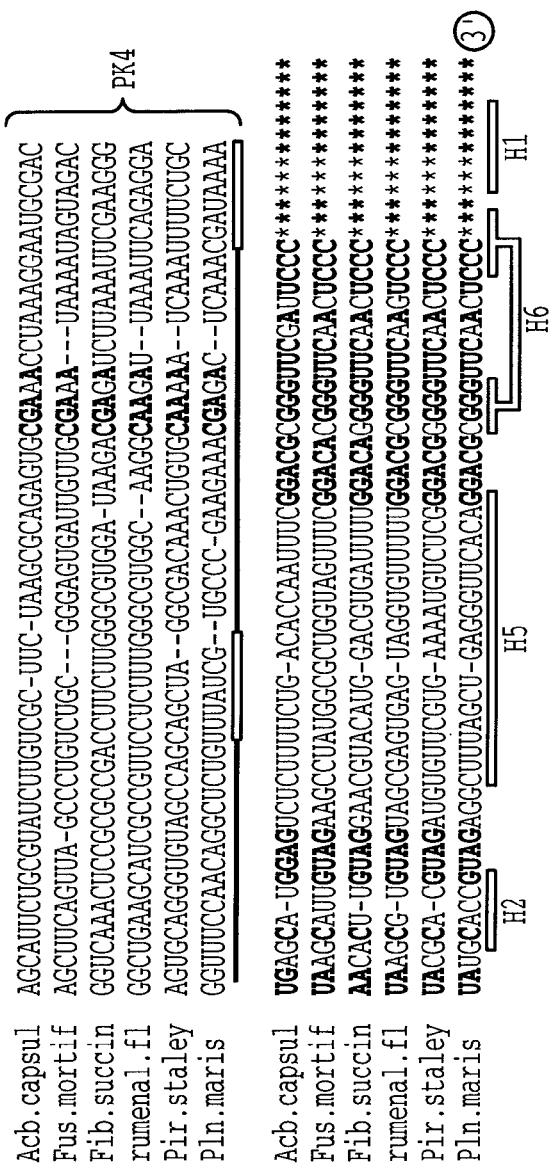

Clm.tracho  GGGGGUGUAAGGUUUCGACUUAG-AAAUGAAGCGUUAAUUGCAUGCGGAGGGCGUUGGCUUCCUAAAAAAGCCGACAAAACA
Clm.mousep  GGGCGUGUAAAGGUUUCGACUUAG-AAAUGAAGCGUUAAUUGCAUGCGGAGGGCGUUGGCUGGCUCCUAAAAAAGCCGACAAAACA
Clm.pneumo  GGGGUGUAUAGGUUUCGACUUGA-AAAUGAAGUGUUAAUUGCAUGCGGAGGGCGUUGGCUGGCUCCUAAAAAAGCCAACAAAACA Clm.tracho  AUAAAUgccgaaccuaaggcugaaugcgaaauuaucagcuucgcugaucucgaauucgaagaguagcugcuUAAuuagcaa-aguuguuacc----uaaauacg-gguGAC
Clm.mousep  AUAAAUgccgaaccuaaggcugaaugcgaaauaucagcuucgcugaucucgaauucgaagaguagcugcuUAAuuagcaa-aguuguuacc----uaaguacu-gguAAC
Clm.pneumo  AUAAAUgccgaaccuaaggcugaaugcgaaauuaugcaguucgcugaucucgaauucuaagagaggaggaaagacuagcuugcuUAAuuagcaaaaaguguuuagcuacuuagcuaguaauucuaguaac
                                                                                    CODING SEQUENCE            H4

Clm.tracho  CCGGUGCUUCGCGAGCUCCACCAGAGGGUUUCGAAACACCCUCGAAUCUGGUU
Clm.mousep  CCGGUGCUUCGCGAGCUCCACCAGAGAGCGCCGUCGAAACGCCGUCGAAUCUGGGUU
Clm.pneumo  CCGGUAUCUCGGCGAGCUCCAGAGACCGUCAAAAAUACCGUCAAUUUAUCUGGGUU
                                                                PK2

Clm.tracho  AGAACUUAGGUCCUUUAAAUCUCGAGGAAAUGAGUUGAAAUUAAUGAGAGU
Clm.mousep  AGAAUUAGGGCCUUUAAAUUCUCUAAUUCCUAGGAAGUUGAAUUGAAAUGAGAGU
Clm.pneumo  GGAACUACUUUCUCUAAAUUCCUAGGAAGUUCGUUGAGAUUU-UUGAGAGU
                                                                PK3

Clm.tracho  CGUUA-GUCUCUAUAGGGUUUCUAGGAGACAUUAACUAGAGUA-CCUAGGAAC
Clm.mousep  CGUUG-GUCUCUAUAGAGAGGCUUCUAGCGAGAGACGAUAAUUAACUAGAAAC
Clm.pneumo  CAUUGG-CUGGCAUAGAGAGCCUUUAUAGGAGUCCAAUCUAAUUUAACAAUCUAGGAAGA
                                                                PK4

Clm.tracho  UAAGCAUGUAGAGGACGAGAGUUCGACUCUCCACCUCCAcca
Clm.mousep  UAAGCAUGUAGAGGACGAGAGUUCGAAUCUCCACCUCCAcca
Clm.pneumo  UAAGCAUGUAGAGGACGAGAGUUCGAGUCUCCACCUCCAcca (3')
                                                                H6         H1

```
Alc.faecal  GCAGUGUUAU-UUACAAAGAAU---C-GAAUCGGUCUGCGCCACGAAGUCCGGUUCUAAAA-CUUAGUGGAU
Alc.eutrop  GCGAGGUCAU-UUACGUCAGAU---A-AGCUCCGGAAGGGUCACGAAGCCCGGGACGAAAA-CCUAGUGACU
Ral.picket  GCGAGGUCAU-UUACGUCAGAU---A-AGCUUUAGGUGAGUCACGGGCCUAGAGACGAAAA-CUUAGUGAAU
Nis.gonorr  GCAACGUCAUCUUACAUUGACU---G-GUUUCCAGCCGGGUUACUUGGCAGGAAAUAAGACUUAAGGUAACU
Nis.meninS  GCAACGUCAUCUUACAUUGACU---G-GUUUCCUGCCGGGUUAUUUGGCAGGAAAUGAGAUUUAAGGUAACU
Chb.violac  GUAGUGUCACUCUACAUCUGCU---A-GUGCUGUUCCGGGUUACUUGGUUCAGUGCGAAAUAAUAGGUAACU
Nms.cryoto  GCAGAGUCAU-UAG-CAAGGAU---C-GCGUUCUGUAGGGUCACUUUACAGAACGUUAAACAAUAGGUGACU
Mtb.glycog  GCAGCGUCAU-UAAGAGAGGAU---C-GUGCGAUAUUGGGUUACUUAAUAUCGUAUUAAAUCCAAGGUAACU
Ps.testost  GCAAGGGAAU-UUUCAUUAGCU---G-GCUGGAUACCGGCUUCUUGGUAUUUGGCGAGAUUUUAGGAAGCU
Vx.paradox  GCAAGGAUAA-CUACAUGGGCU---G-GCUCCGAUCCGGGUACCUUGGGUCGGGGCGAGAAAAAUAGGGUACU
Hph.paller  GCAAGGUAAU-UUACAUCGGCU---G-GUUCUGCGUCGGGCACCUUGGCGCAGGAUGAGAUUCAAGGAUGCU
Brd.pertus  GCAGCGACAU-UCACAAGGAAU---CGGCCACCGCUGGGGUCACA-CGGCGUUGGUUUAAA-UUACGUGAAU
                                  PK2                                              } PK3

Alc.faecal  CGCCAAGG-AAAGGCCUGUCA-AUUGGCAUAGUCCAAGGUUAAAACUUAAAAUUAAU-UGAC
Alc.eutrop  CGCCGUCG-UAGAGCGUGUUC-GUCCGCGAUG-CGCCGGUUAAAU---CAAA-UGACAGAAC
Ral.picket  CGCCGUCG-UAGAGCGUGUUC-GUCCGCGAUG-CGGCGGUUAAAU---CAAA-UGACAGAAC
Nis.gonorr  GGUUUCCA-AAAGGCCUGUUG-GUCGGCAUGA-UGGAAAUAAGAUUUUCAAAUAGACACAAC
Nis.meninS  GGUUUCCA-AAAGGCCUGUUG-GUCGGCAUGA-UGGAAAUAAGAUUUUCAAAUAGACACAAC
Chb.violac  CGCCAAAGUCCA-GCCUGUCC-GUCGGCGUGG-CAGAGGUUAAAUC--CAAA-UGACACGAC
Nms.cryoto  CGCCUGCC-AUCAGCCCGCCA-GCUGGCGGUU-GUCAGGUUAAAU---UAAA-GAGCAUGGC
Mtb.glycog  CGCCUGCU-GUUUGCUUGCUC-GUUGGUGAGC-AUCAGGUUAAAU---CAAA-CAACACAGC
Ps.testost  GGCUACCCAAGCAGCGUGUGC-CUGCGGGGUUUGGGUGGCGAGAUU--UAAA-ACAGAGCAC
Vx.paradox  GGCGUCCGGUUUAGCGUGUGA-CUGCGCGACUCCGGAAGCGAGACU--CAAA-ACAGAUCAC
Hph.paller  GGCUUCCCGUUUAGCGUGCCA-CUGCGCGACUCGGCGGCGAGACC--CAAA-UCAGACGGC
Brd.pertus  CGCCCUGG-UCCGGCCCGUCG-AUCGGCUAAGUCCAGGGUUAAAUC--CAAAUAGAU-CGAC
                                                                           } PK4

Alc.faecal  UACACAUGUAGAACUGUCUGUGGACGGCUUGCGGACGGGGGUUCGAUUCCC************
Alc.eutrop  UAAGUAUGUAGAACUCUCUGUGGAGGGCUUACGGACGCGGGUUCGAUUCCCGCCGGCUCCACCA
Ral.picket  UAAGUAUGUAGAACUCUCUGUGGAGGGCUUGCGGACGCGGGUUCGAUUCCC************
Nis.gonorr  UAAGUAUGUAGAACGCUUUGUAGAGGACUUUCGGACGGGGGUUCGAUUCCCCCCGCCUCCACCA
Nis.meninS  UAAGUAUGUAGAACGCUUUGUAGAGGACUUUCGGACGGGGGUUCGAUUCCCCCCGCCUCCACCA
Chb.violac  UAAGUAUGUAGAACUCACUGUAGAGGACUUUCGGACGCGGGUUCAACUCCC************
Nms.cryoto  UAAGUAUGUAGAACUGUCUGUAGAGGACUUGCGGACGCGGGUUCAACUCCC************
Mtb.glycog  UAAGUAUGUAGAACUGUCUGUGGAGGGCUUGCGGACGGGGGUUCGAUUCCC************
Ps.testost  UAAACAUGUAGAUCUGUCCGGCGAAGGCUUACGGACGCGGGUUCAAUUCCCGCCGGCUCCA***
Vx.paradox  UAAACAUGUAGAACUGCGCGAUGAAGGCUUGCGGACGGGGGUUCAACUCCC************
Hph.paller  UACACAUGUAGAACUGCUCGAAAAAGGCUUGCGGACGGGGGUUCAACUCCC************
Brd.pertus  UAAGCAUGUAGAACUGGUUGCGGAGGGCUUGCGGACGGGGGUUCAAUUCCCCCCGGCUCCACCA (3')
                 H2         H5              H6    H1
```

FIG. 9B

```
             H1                  H5              H2
         5'  ━━                 ━━━━━━━━━━━━━━━━━━━━━
Leg.pneumo  *******************CGUGGGUUGCAAAACCGGAAGUGCAUGC
Chr.vinosu  *******************CGUGGGUCGCGAAACCUAAGGUGCAUGC
Dcb.nodosu  ***************************CUCGAGGUGCAUGU
Ps.aerugin  GGGGCCGAUU-AGGAUUCGACGCCGGUAACAAAACUUGAGGGGCAUGC
Ps.fluores  *******************CGCCGGUUGCGAACCUUUAGGUGCAUGC
Mar.hydroc  *******************CGCCGGUGACGAACCCUUGGGUGCAUGC
Shw.putref  GGGGGCGAUUCUGGAUUCGACAGGAUUCACGAAACCCUGGGAGCAUGC
Psm.halopl  *******************CGGAAUUCAAGAAGCCCGAGGUGCAUGU
Ae.salmoni  *******************CAAGAUUCACGAAACCCAAGGUGCAUGC
S.typhimur  GGGGCUGAUUCUGGAUUCGACGGGAUUUGCGAAACCCAAGGUGCAUGC
E.coli      GGGGCUGAUUCUGGAUUCGACGGGAUUUGCGAAACCCAAGGUGCAUGC
Yer.pestis  GGGGCUGAUUCUGGAUUCGACGGGAUUCGCGAAACCCAAGGUGCAUGC
V.cholerae  GGGGCUGAUUCAGGAUUCGACGGGAAUUUUGCAGUCUGAGGUGCAUGC
H.influenz  GGGGCUGAUUCUGGAUUCGACGGGAUUAGCGAAGCCCAAGGUGCACGU
H.actinomy  GGGGCUGAUUCUGGAUUCGACGGGAUUAGCGAAGCCCGAAGUGCACGU
                                   PK1
                        ┌─────────────────────────────┐
Leg.pneumo  CGAG-AAGGAGAUC-UCUCGUAAAUA-AGA-CUCAAUUA-AAU
Chr.vinosu  CGAG-GUGCGGUUGACCUCGUAAAAC--CCUCCGCAAA--CUU
Dcb.nodosu  CGAG-AAUGAGAGAAUCUCGUUAAAU--ACUUUCAAAA--CUU
Ps.aerugin  CGAGCUGGUAGCAGAACUCGUAAAUUCGCUGCUGCAAA--CUU
Ps.fluores  CGAGUUGGUAACAGAACUCGUAAAUCCACUGUUGCAACUUUCU
Mar.hydroc  CGAGAUGGCAGCGAAUCUCGUAAAUCCAAAGCUGCAAC--GUA
Shw.putref  CGAG-GGGCGGUUGGCCUCGUAAA----AAGCCGCAAA--GUU
Psm.halopl  CGAG-GUGCGGUUUGCCUCGUAAAA---AAGCCGCAAUU-UAA
Ae.salmoni  CGAG-GUGCGGUAGGCCUCGUUAAC---AAACCGCAAA--AAA
S.typhimur  CGAG-GGGCGGUUGGCCUCGUAAA----AAGCCGCAAA--AAA
E.coli      CGAG-GGGCGGUUGGCCUCGUAAA----AAGCCGCAAA---AA
Yer.pestis  CGAG-GUGCGGUG-GCCUCGUAAA----AAACCGCAAA-AAAA
V.cholerae  CGAG-GUGCGGUAGGCCUCGUUAAC---AAACCGCAAA--AAA
H.influenz  CGAG-GUGCGGUAGGCCUCGUAAAU---AAACCGCAAA--AAA
H.actinomy  CGAG-GUGCGGUAGGCCUCGUAAAU---AAACCGCAAA--AAA
                                                    CODING SEQUENCE
                                                          ↓
Leg.pneumo  A-UAAAU gcaaacgaugaaaacuuugcugguggggaagcuaucgcugcc UAA-----UAAGCACUUU
Chr.vinosu  A-UAGUU gccaacgacgacaacuac-----------gcucucgcugcu UAA-----UCCCAGCGGG
Dcb.nodosu  A-UAGUU gcaaacgacgacaacuac-----------gcuuuagcggcu UAA-----UUCCCGCUUU
Ps.aerugin  A-UAGUU gccaacgacgacaacuac-----------gcucuagcugcu UAA------UGCGGCUAG
Ps.fluores  A-UAGUU gccaaugacgaaaccuac---gggaauacgcucucgcugcg UAA-------GCAGCCUU
Mar.hydroc  A-UAGUC gcaaacgacgaaaacuac-----------gcacuggcggcg UAA---GCCGUU-CCAGU
Shw.putref  A-UAGUU gcaaacgacgauaacuac-----------gcucuagccgcu UAA------UGCCGCUAG
Psm.halopl  AGUAAUC gcaaacgacgauaacuac-----------ucucuagcagcu UAG------GCUGGCUAG
Ae.salmoni  A-UAGUC gcaaacgacgaaaacuac-----------gcacuagcagcu UAAUAACCUGCAUAGAGC
S.typhimur  A-UAGUC gcaaacgacgaaaccuac-----------gcuuuagcagcu UAAUAACCUGCUUAGAGC
E.coli      A-UAGUC gcaaacgacgaaaacuac-----------gcuuuagcagcu UAAUAACCUGCUUAGAGC
Yer.pestis  A-UAGUU gcaaacgacgaaaacuac-----------gcacuagcagcu UAAUAACCUGCUUAGAGC
V.cholerae  A-UAGUC gcaaacgacgaaaacuac-----------gcacagcagcu UAAUACCCUGCUCAGAGC
H.influenz  A-UACUC gcaaacgacgaacaauac-----------gcuuuagcagcu UAAUACCUGCAUUUAGC
H.actinomy  A-UAGUC gcaaacgacgaacaauac-----------gcuuuagcagcu UAAUACCUGCCUUUAGC
                                                              H4
```

FIG. 10A

```
Leg.pneumo  AGUUAAACCAUCACUGUGUACUGGCCAAUAAACCCAGUAUC
Chr.vinosu
Dcb.nodosu
Ps.aerugin
Ps.fluores  AGCCCUUCCCUCCUGGUACCUUCGGGUCCAG
Mar.hydroc
Shw.putref
Psm.halopl
Ae.salmoni
S.typhimur
E.coli
Yer.pestis
V.cholerae
H.influenz
H.actinomy Leg.pneumo  CCGUUCG-ACCGAGCCC--GCUUAUC-GGUAUCGAA-------UCAACGGUCAU-AAGAGAU-AAGCU
Chr.vinosu  CCUCUGA-CCGUCACUU--GCCUGUGGGCGGCGGAUU------CCAGGGGUAAC-CUCACAC-AGGAU
Dcb.nodosu  CGCUUAC-CUAGAUUU---GUCUGUGGGUUUACC---------GUAAGCGACAU--UAACAC-AGAAU
Ps.aerugin  CAGUCGC-UAGGGGAU---GCCUGUAAACCCGAAA---------CGACUGUCAG-AUAGAAC-AGGAU
Ps.fluores  CAAUCAU-CAGGGGAU---GUCUGUAAACCCAAAG---------UGAUUGUCAU-AUAGAAC-AGAAU
Mar.hydroc  CGUCCUG-GCUGAGGC---GCCUAUAACUCAGUAGCAACAUCCCAGGACGUCAU-CGCUUAU-AGGCU
Shw.putref  CCAUCUA-CCACACGCUUUGCACAUGGGCAGUGGAUU------UGAUGGUCAU-CUCACAUCGUGCU
Psm.halopl  CGCUCCU-UCCAUGUAU--UCUUGUG-GACUGGAUUUU------GGAGUGUCACCCUAACAC-CUGAU
Ae.salmoni  CCUUCUA-CCCUAGCUU--GCCUGUGUCCUAGGGAAUC------GGAAGGUCAU-CCUUCAC-AGGAU
S.typhimur  CCUCUCU-CCCUAGCCUCCGCUCUUAGGACGGGGAUCA-----AGAGAGGUCAAACCCAAAA-GAGAU
E.coli      CCUCUCU-CCCUAGCCUCCGCUCUUAGGACGGGGAUCA-----AGAGAGGUCAAACCCAAAA-GAGAU
Yer.pestis  CCUCUCU-CCCUAGCCUCCGCUCUUAGGACGGGGAUCA-----AGAGAGGUCAAACCUAAAA-GAGCU
V.cholerae  CCUUCCU-CCCUAGCUUCCGCUUGUAAGACGGGGAAAUC----AGGAAGGUCAAACCAAAUC-AAGCU
H.influenz  CUUCGCG-CUCCAGCUUCCGCUCGUAAGACGGGGAUAA-----CGCGGAGUCAAACCAAAAC-GAGAU
H.actinomy  CUUCGCU-CCCCAGCUUCCGCUCGUAAGACGGGGAUAA-----AGCGGAGUCAAACCAAAAC-GAGAU
                                        PK2
```

FIG. 10B

```
                                    PK3
             ╔══════════════════════════════════════════════════╗
Leg.pneumo   -AGCG-UCCU-AAUCU--AUCCC-GGGUU-AUGG-CGCGAAA-CU-CA--GGGAAU
Chr.vinosu   -CGUG-GUGA-CGGGA--GUCCG-GACCU-GAUC-CACUAAAACC-UA-ACGGAAU
Dcb.nodosu   -CGCU-GGUU-AACG---CGUCCGC-UGUU-AAUC-GGUUAAA-UU-AA-GCGGAAU
Ps.aerugin   -CGCC-GCCA-AGUU--CGCUGUA-GACG-UAAC-GGCUAAAACU-CA-UACAGCU
Ps.fluores   -CGCC-GUGC-AGUA--CGUUGUG-GACG-AAGC-GGCUAAAACU-UA-CACAACU
Mar.hydroc   GCUCC-GUUC-ACCAG-AGCUCA-CUGGU-GUUC-GGCUAAG-AU-UA-AAGAGCU
Shw.putref   -AGCGAGGGA-ACCC--UGUCUGG-GGGU-GAAC-CGCGAAACAG-UA-CCGGACU
Psm.halopl   -CGCGACGGA-AACCC-UGGCCG-GGGUU-GAAG-CGUUAAAACU-AA-GCGGCCU
Ae.salmoni   -CGUG-UGGA-AGUCC-UGCUCG-GGGCG-GAAG-CAUUAAAACC-AA-UCGAGCU
S.typhimur   -CGCG-CGGA-UGCCC-UGCCUG-GGGUU-GAAG-CGUUAAAACG-AA-UCAGGCU
E.coli       -CGCG-UGGA-AGCCC-UGCCUG-GGGUU-GAAG-CGUUAAACUUAA-UCAGGCU
Yer.pestis   -CGUG-UGGA-AACCU-UGCCUG-GGGUG-GAAG-CAUUAAAACU-AA-UCAGGAU
V.cholerae   -GGCG-UGGA-UUCCCCCACCUGA-GGGAUGAAG-CGCGAGAUCU-AAUUCAGGUU
H.influenz   -CGUG-UGGA-AGCCACCGUUUGA-GGAUCGAAG-CACUAAAUUG-AA-UCAAACU
H.actinomy   -CGUG-UGGA-AGCCACCGUUUGA-GGAUCGAAG-CAUUAAAUUA-AA-UCAAAGU ╔══════════════════════════════════════════════════════════╗
Leg.pneumo   CGCUGUGUAU-CAUCCUGCCC-GUCGGAGGAGCCACAGUUAAAUUCAAAAGACAAGGC--  ⎫
Chr.vinosu   CGCCGACUGAUCGCCCUGCCC-UUCGGGCGGCAGAAGGCUAAAAACAAUAGAGUGGGC--  ⎪
Dcb.nodosu   CGCUUGUAAA-AUGCCUGAGC-GUUGGCUGUUUAUGAGUUAAACCUAAUUAACUGCUC-   ⎪
Ps.aerugin   CGCUCCAAGC--ACCUGCCA-CUCGGGCGGCGCGGAGUUAA-CUCAGUAGAGCUGGC--   ⎪
Ps.fluores   CGCCCAAAGC--ACCCUGCCC-GUCGGGUCGCUGAGGGUUAA-CUUAAUAGACACGGC--  ⎪
Mar.hydroc   CGCCUCUUGC--ACCCUGACC-UUCGGGUCGCUUGAGGUUAA-AUCAAUAGAA-GGACAC  ⎪
Shw.putref   CACCGUGUGG-GAUCCUGUCU-UUCGGAGUUCAAACGGUUAA-ACAAUA-GAA-AGAC--  ⎬ PK4
Psm.halopl   CGCCUUUAUC-UACCGUGUUU-GUCCGGGAUUUAAAGGUUAA-UUAAAU-GACAAUAC--  ⎪
Ae.salmoni   AGUCAAUUCG-UGGCGUGUCU-CUCCGCAGCGGGUUGGCGAA-UGUAAA-GAG-UGAC--  ⎪
S.typhimur   AGUCUGGUAG-UGGCGUGUCC-GUCCGCAGGUGCCAGGCGAA-UGUAAA-GAC-UGAC--  ⎪
E.coli       AGUUUGUUAG-UGGCGUGUCC-GUCCGCAGCUGGCAAGCGAA-UGUAAA-GAC-UGAC--  ⎪
Yer.pestis   AGUUUGUCAG-UAGCGUGUCC-AUCCGCAGCUGGCCGGCGAA-UGUAAU-GAUUGGAC--  ⎪
V.cholerae   AGCCAUUCGU-UAGCGUGUCG-GUUCGCAGGCG-GUGGUGAA-AUUAAA-GAU-CGAC--  ⎪
H.influenz   AGCUUAAGUU-UAGCGUGUCU-GUCCGCA-UGCUUAAGUGAA-AUUAAA-GACGAGAC--  ⎪
H.actinomy   AGCUUAAUUG-UCGCGUGUCC-GUCAGCA-GGAUUAAGUGAA-UUUAAA-GACCGGAC--  ⎭

Leg.pneumo   UAUGCAUGUAGAGCUAAAGGCAGAGGACUUGCGGACGCGG*********************
Chr.vinosu   UAAGCAUGUAGGACCGAGGGCAGAGGGCUUGCGGACGCGG*********************
Dcb.nodosu   UAAACAUGUAGUACCAAAAGUUAAGGAUUCGCGGACGGGGGUUCAAAUCCCCCGCCUCCACCA
Ps.aerugin   UAAGCAUGUAGAACCGAUAGCGGAGAGCUGGCGGACGGGGGUUCAAAUCCCCCCGGCUCCACCA
Ps.fluores   UACGCAUGUAGUACCGACAGCAGAGUACUGGCGGACGGGG*********************
Mar.hydroc   UAAGCAUGUAGACCUCAAGGCCUAGUGCUGGCGGACGCGG*********************
Shw.putref   UAAGCAUGUAGCGCCUUGGAUGUAGGUUUUCUGGACGCGGGUUCAAGUCCCGCCGCCUCCACCA
Psm.halopl   UAAACAUGUAGUACCGACGGUCGAGGCUUUUCGGACGGGG*********************
Ae.salmoni   UAAGCAUGUAGUACCGAGGAUGUAGUAAUUUUGGACGGGG*********************
S.typhimur   UAAGCAUGUAGUACCGAGGAUGUAGGAAUUUCGGACGCGGGUUCAACUCCCGCCAGCUCCACCA
E.coli       UAAGCAUGUAGUACCGAGGAUGUAGGAAUUUCGGACGCGGGUUCAACUCCCGCCAGCUCCACCA
Yer.pestis   UAAGCAUGUAGUGCCGACGUGUAGUAAUUUCGGACGGGGGUUCAAAUCCCCCCAGCUCCACCA
V.cholerae   UAAGCAUGUAGUACCAAAGAUGAAUGGUUUUCGGACGGGGGUUCAACUCCCCCCAGCUCCACCA
H.influenz   UAAACGUGUAGUACUGAAGGUAGAGUAAUUUCGGACGGGGGUUCAACUCCCCCCAGCUCCACCA
H.actinomy   UAAACGUGUAGUGCUAACGGCAGAGGAAUUUCGGACGGGGGUUCAACUCCCCCCAGCUCCACCA ③'
             ══════      ══════════  ═══════    ══  ══
               H2           H5         H6       H1
```

EUBACTERIAL TMRNA SEQUENCES AND USES THEREOF

CROSS-REFERENCE TO RELATED APPLICATIONS

The present application is division of U.S. patent application Ser. No. 11/329,230 filed on 11 Jan. 2006, which in turn in a division of U.S. patent application Ser. No. 09/958,206 filed on 20 Feb. 2002, now U.S. Pat. No. 7,115,366, which in turn is a national stage filing under 35 U.S.C. §371 of International patent application No. PCT/US00/08988 filed on 6 Apr. 2000, which in turn is related to and claims priority under 35 U.S.C. §119(e) to U.S. provisional patent application Ser. No. 60/128,058 filed on 7 Apr. 1999. Each of these applications is incorporated herein by reference.

This application was made with Government support under Grant No. GM 48152, funded by the National Institutes of Health, Bethesda, Md. The Government has certain rights in this invention.

BACKGROUND OF THE INVENTION

The present invention is directed to eubacterial tmDNA sequences and the corresponding tmRNA sequences. The present invention is further directed to alignments of eubacterial tmDNA sequences and use of the sequences and sequence alignments for the development of antibacterial drugs. The present invention is also directed to the use of the sequences for the development of diagnostic assays.

The publications and other materials used herein to illuminate the background of the invention or provide additional details respecting the practice are incorporated by reference, and for convenience are respectively grouped in the appended List of References.

Eubacterial tmRNAs (10Sa RNAs) are unique since they function, at least in E. coli, both as tRNA and as mRNA (for a review, see Muto et al., 1998). These ≈360±10% nucleotide RNAs are charged with alanine at their 3'-ends (Komine et al., 1994; Ushida et al., 1994) and also have a short reading frame coding for 9 to 27 amino acids depending on the bacterial species. E. coli tmRNA mediates recycling of ribosomes stalled at the end of terminatorless mRNAs, via a trans-translation process (Tu et al., 1995; Keiler et al., 1996; Himeno et al., 1997). In E. coli, this amino acid tag is co-translationally added to polypeptides synthesized from mRNAs lacking a termination codon, and the added 11 amino acid C-terminal tag makes the protein a target for specific proteolysis (Keiler et al., 1996).

Structural analyses based on phylogenetic (Felden, et al., 1996; Williams and Bartel, 1996) and probing (Felden et al., 1997; Hickerson et al., 1998) data have led to a compact secondary structure model encompassing 6 helices and 4 pseudoknots. tmRNAs have some structural similarities with canonical tRNAs, especially with tRNA acceptor branches. E. coli tmRNA contains two modified nucleosides, 5-methyluridine and pseudouridine, located in the tRNA-like domain of the molecule, in a seven-nucleotide loop mimicking the conserved sequence of T loops in canonical tRNAs (Felden et al., 1998).

Fifty-three tmRNA sequences are now known from both experimental data and Blast searches on sequenced genomes (summarized in Williams, 1999; Wower and Zwieb, 1999). These sequences cover only 10 phyla, less than one third of the known bacterial taxa. It is desired to determine additional tmRNA sequences and to use the tmRNA sequences for drug development.

SUMMARY OF THE INVENTION

The present invention relates to eubacterial tmDNA sequences and the corresponding tmRNA sequences. The present invention further relates to alignments of eubacterial tmDNA sequences and use of the sequences and sequence alignments for the development of antibacterial drugs.

In one aspect of the present invention, an extensive phylogenetic analysis was performed. Fifty-eight new tmDNA sequences including members from nine additional phyla were determined. Remarkably, tmDNA sequences could be amplified from all species tested apart from those in the alpha-Proteobacteria. This aspect of the invention allowed a more systematical study of the structure and overall distribution of tmRNA within eubacteria In a second aspect of the invention, alignments are made with the newly isolated tmDNA sequences and previously disclosed tmRNA sequences.

In a third aspect of the invention, the alignments of the tmRNA sequences allow the identification of targets for development of antibacterial drugs.

In a fourth aspect of the invention, the novel tmDNA or tmRNA sequences of the present invention are used to develop diagnostic assays, such as amplification-based assays, for the bacterial species disclosed herein.

BRIEF DESCRIPTION OF THE FIGURES

FIGS. 3A, 3B and 3C show the sequence alignment, structural domains and structural features for the tmRNA of several species of *Firmicutes*. The tmRNA sequences are set forth in SEQ ID NOs:67-87.

FIGS. 4A and 4B show the sequence alignment, structural domains and structural features for the tmRNA of several species of *Thermophiles*. The tmRNA sequences are set forth in SEQ ID NOs:88-99.

FIGS. 7A-1, 7A-2, 7B, 7C and 7D show the sequence alignment, structural domains and structural features for the tmRNA of several species of *Mesophiles* (7A-1, 7A-2, 7C, 7D) and environmental sludge (7B). The tmRNA sequences of the *Mesophiles* are set forth in SEQ ID NOs:118-123 and 125-128, and the tmRNA sequence of the environmental sludge is set forth in SEQ ID NO:124.

Figure 8B:
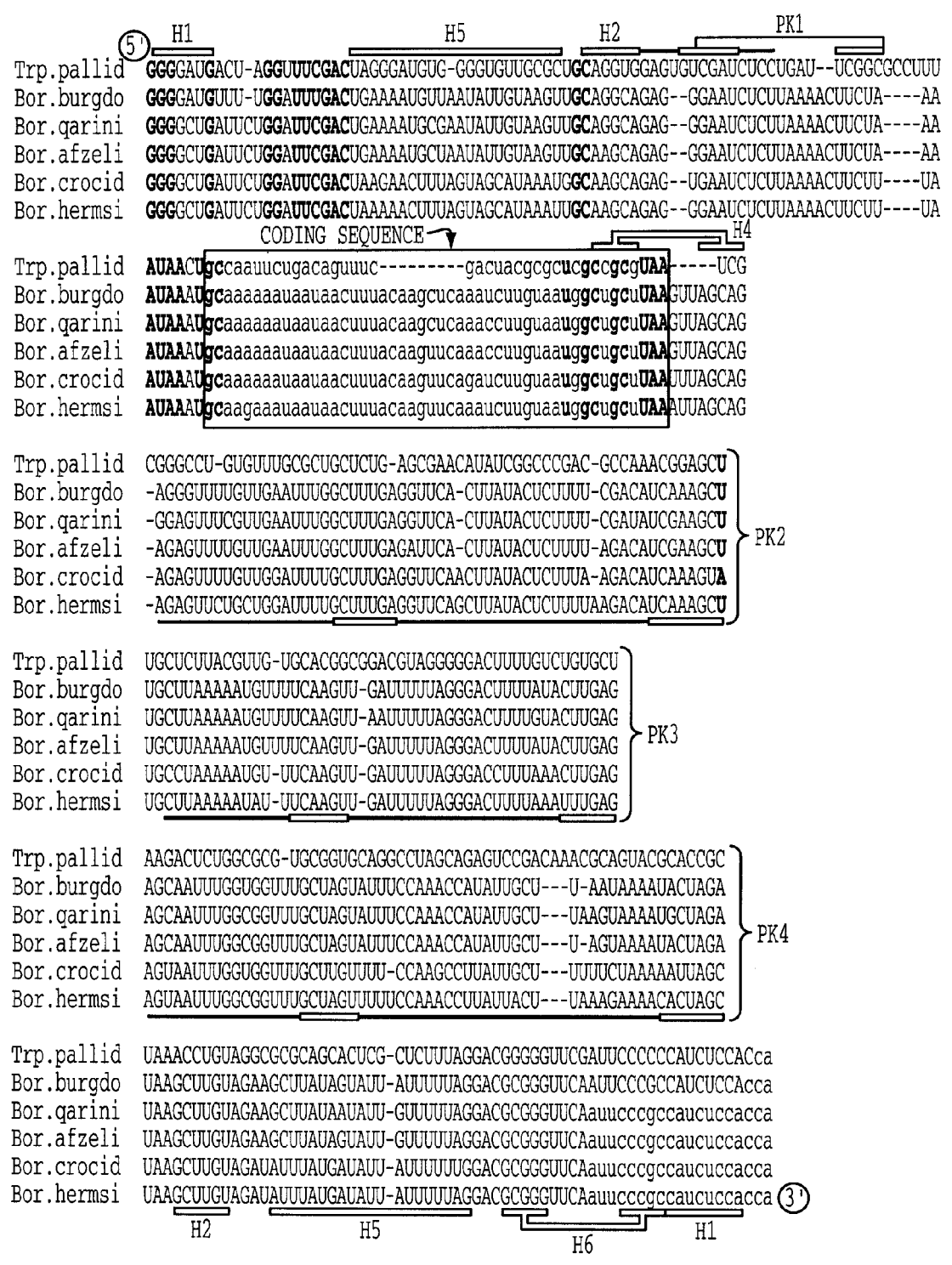

FIGS. 8A and 8B show the sequence alignment, structural domains and structural features for the tmRNA of several species of *Actinobacteries* (8A) and *Spirochaetes* (8B). The tmRNA sequences of the *Actinobacteries* are set forth in SEQ ID NOs:132-136, and the tmRNA sequences of the *Spirochaetes* are set forth in SEQ ID NOs:137-142.

FIGS. 9A and 9B show the sequence alignment, structural domains and structural features for the tmRNA of several species of *Pourpres* beta. The tmRNA sequences are set forth in SEQ ID NOs:143-154.

FIGS. 10A, 10B and 10C show the sequence alignment, structural domains and structural features for the tmRNA of several species of *Pourpres* gamma. The tmRNA sequences are set forth in SEQ ID NOs:155-169.

DETAILED DESCRIPTION OF THE INVENTION

Figure 1B:
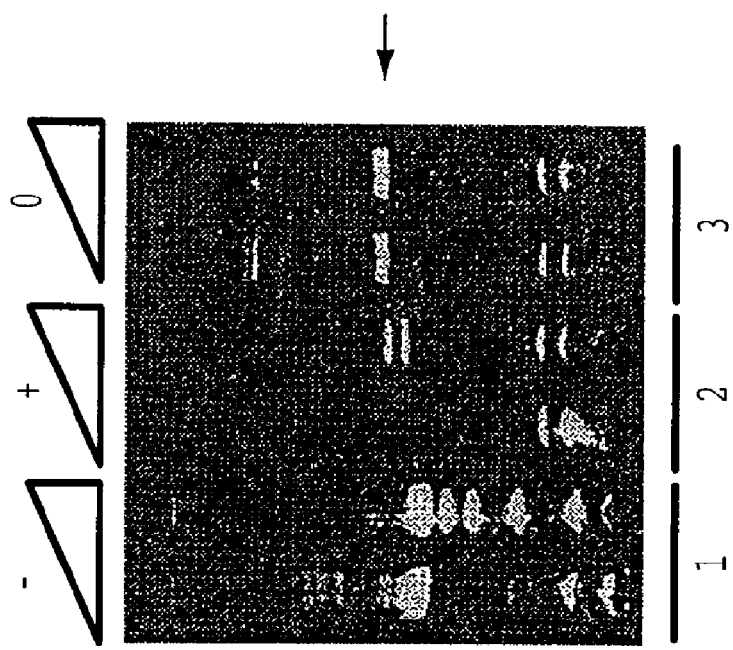
FIGS. 1A-1B show the effect of the annealing temperature (FIG. 1A) and magnesium concentration (FIG. 1B) on amplifying eubacterial tmRNA genes from genomic DNAs using PCR. A: Varying the annealing temperature from 50° to 70° C. during the PCR amplification of *Thermus aquaticus* (1). B; Varying the magnesium concentration to amplify tmDNA genes from *Thermus aquaticus* (1), negative effect of increasing the magnesium concentration), *Acholeplasma laidlawii* (2), positive effect of increasing the magnesium concentration, the upper band is the tmDNA gene) and from *Mycoplasma salivarium* (3), no discernible effect of magnesium ions in that concentration range). The arrows point toward the 4 novel tmDNA genes that have been sequenced.

The present invention is directed to eubacterial tmDNA sequences and the corresponding tmRNA sequences. The present invention is further directed to alignments of eubacterial tmDNA sequences and use of the sequences and sequence alignments for the development of antibacterial drugs.

The novel eubacterial tmDNA sequences determined in accordance with the present invention are set forth in Tables 1-58, below. The alignment of tmRNA sequences is shown in FIGS. 3A-11B, which also show the structural domains and structural features of the tmRNA. The present invention also includes the tmRNA sequences set forth in these figures to the extent they differ from the sequences set forth in Tables 1-58.

The sequences, especially as identified by the sequence alignment, represent targets for the development of drugs which may be broadly applicable to many kinds of bacteria, or may be broadly applicable only to a particular genera of phylum of bacteria, or may be specifically applicable to a single species of bacteria. Thus, the present invention is further directed to the development of drugs for the therapeutic treatment of bacteria, generically or specifically. Suitable drugs are developed on the basis of the tmRNA sequences as described herein.

For all the novel tmRNA sequences, as well as with the ones that are already known, there are systematically several structural domains that are always found. These domains can be used as targets for the development of drugs which may be genera specific or which may be eubacteria specific. These domains are either RNA helices which can be sometimes interrupted by bulges or pseudoknots. The RNA helices which are always present are H1, H2, H5 and H6. Helices H1 and H6 are found in all canonical transfer RNAs. Thus, H1 and H6 are not good targets for drug development because drugs that would target them will also interfere with the biology of the individual that has a given disease. Consequently, very good candidates for development of drugs for targeting as many bacteria as possible are helices H2 and H5. Moreover, helices H2 and H5 are critical for the folding of all these tmRNA since both of them connect the two ends of the molecule together. Disruption of either H2 or H5 with a specific drug would lead to inactive tmRNA molecules in vivo. Similarly, pseudoknots PK1, PK2 and PK3 are always found in the bacterial tmRNAs. Since these pseudoknots are not found in all canonical transfer RNAs, they can also be targeted with specific drugs. Disruption of either PK1 or PK2 or PK3 with a specific drug would lead to inactive tmRNA molecules in vivo.

In addition to developing drugs which broadly target many bacteria, drugs are developed which are more genera specific. For trying to target specifically a given bacteria or a complete phylum, the coding sequence (shown in all the alignments) is a very good candidate. Indeed, this region of the RNA is very accessible for DNA antisense binding (such as shown for *Escherichia coli*; Matveeva et al., 1997), and thus, is also available for interaction with other drugs. Moreover, the coding sequence is a critical functional domain of the molecule in its quality-control mechanism in cells.

Interestingly, some structural domains are present only in a given bacterial phyla and could be targeted for discovering a drug that will be specific of a phylum, but not of the others. For example:

(1) in the cyanobacteria, the fourth pseudoknot PK4 is made of two smaller pseudoknots called PK4a and PK4b;

(2) in the mycoplasma, helix H2 is made of only 4 base-pairs instead of 5 in the other species;

(3) for two sequences of chlorobium as well as *Bacteroides thetaiotaomicron* and ppm gingiv., there is an additional domain just downstream of the coding sequence that is unique to them;

(4) there is always a stem-loop in the coding sequence of the actinobacteria (Felden et al., 1999); and (5) all the beta proteobacteria possess a sequence insertion in pseudoknot PK2 (shown in the alignment).

The novel sequences described herein, when aligned, show that specific structural domains within tmRNA are strictly conserved, as for example pseudoknot PK1 is located upstream (at the 5'-side) of the coding sequence. As previously disclosed, this pseudoknot is a target for future antibacterial drugs. Moreover, recent data have shown that this PK1 pseudoknot, among all the four pseudoknots within tmRNA gene sequences (sometimes there's only 2 or 3 detectable pseudoknots, depending upon the sequences), is the only one that its correct folding is essential for the biological activity of tmRNA (Nameki et al., 1999; Nameki et al., 2000).

It has recently been discovered that even the alpha-proteobacteria possess tmRNA genes. These genes are permuted and are made in two parts, connected via a processed linker. These tmRNA gene sequences from alpha-proteobacteria were not found in the course of the present invention because usual PCR methods could not amplify them.

Recent reports have shown that whereas the gene encoding tmRNA is non-essential in *E. coli* (does not kill the bacteria when disrupted), it is indeed essential in *Neisseria gonorrheae* (Huang et al., 2000). Also, tmRNA is directly involved in *Salmonella typhymurium* pathogenticity (Julio et al., 2000).

In summary, tmRNA genes are present in all eubacterial genomes, with no exceptions, but are not present in any genomes from archebacteries or eukaryotes, with the exception of some chloroplasts. The very specific location of tmRNA genes within one of the three main kingdoms of life make them ideal targets for the design of novel antibiotics that will, in principle, interfere very weakly with human biochemistry, compared to usual antibiotics. For a recent review about designing novel antibiotics, see Breithaupt (1999).

The present invention is also directed to diagnostic assays and kits for the detection of bacterial infection, particularly infections caused by bacterial agents disclosed herein. In one embodiment, the coding sequence of each bacterial species is used to design specific primers for use in amplification-based diagnostic assays for infectious diseases. Specific primers are designed in accordance with well known techniques, and such design is readily done by a skilled artisan. Amplification-based diagnostic assays are performed in accordance with conventional techniques well known to skilled artisans. Examples of amplification-based assays include, but are not limited to, polymerase chain reaction (PCR) amplification, strand displacement amplification (SDA), ligase chain reaction (LCR) amplification, nucleic acid sequence based amplification (3SR or NASBA) and amplification methods based on the use of Q-beta replicase.

Drugs which target the sequences described herein are active agents can be formulated in pharmaceutical compositions, which are prepared according to conventional pharmaceutical compounding techniques (*Remington's*, 1990). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may dissolved in a pharmaceutical carrier and administered as either a solution of a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in an therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences* (18).

Alternatively, targeting therapies may be used to deliver the active agent more specifically to certain types of cell, by the use of targeting systems such as antibodies or cell-specific ligands. Targeting may be desirable for a variety of reasons, e.g. if the agent is unacceptably toxic, or would otherwise require too high a dosage, or otherwise be unable to enter the target cells.

Antisense active agents can also be delivered by techniques described in U.S. Pat. Nos. 5,811,088; 5,861,290 and 5,767,102.

EXAMPLES

The present invention is further detailed in the following Examples, which are offered by way of illustration and are not intended to limit the invention in any manner. Standard techniques well known in the art or the techniques specifically described below are utilized.

Example 1

Materials and Methods

1. Extraction of Genomic DNA

Bacterial genomic DNAs were prepared from ≈10 mg freeze-dried cells provided from ATCC (American Type Culture Collection, Virginia, USA). Cell pellets were resuspended in 750 µL of lysis buffer (50 mM Tris (pH 8.0), 50 mM EDTA and 20% sucrose). 150 µL of a 10 mg/mL solution of lysozyme was mixed and let stand at room temperature for 15 min. 150 µL of 1% SDS was added and let stand at room temperature for 15 minutes. Four to five phenol/chloroform extractions were performed, until the sample was clear and there was no interphase. Two to five µL of a 10 mg/mL solution of RNase DNase-free was added and incubated at room temperature for 30 minutes. After a phenol/chloroform extraction of the enzyme, the genomic DNA was precipitated with 1/10 volume of 3M NaOAc (pH 5.5) and 1 volume isopropanol, and stored at −20° C. for 2 hours. After centrifugation, the genomic DNAs were washed with 70% ethanol, vacuum-dried and diluted in sterile water to a final concentration of 10 ng/µL.

2. Primer Sets for PCR Reactions

The following primer sets were used during the PCR:

```
primer set A
(based on E. coli tmRNA termini):
5'-GGG GCT GAT TCT GGA TTC GAC-3'    (SEQ ID NO: 1)
and

5'-TGG AGC TGG CGG GAG TTG AAC-3';   (SEQ ID NO: 2)

primer set B
(based on T. neapolitana tmRNA termini):
5'-GGG GGC GGA AAG GAT TCG ACG-3'    (SEQ ID NO: 3)
and

5'-TGG AGG CGG CGG GAA TCG AAC-3';   (SEQ ID NO: 4)
```

-continued

```
primer set C
(based on M. pneumoniae tmRNA termini):
5'-GGG GAT GTC ATG GTT TTG ACA-3'      (SEQ ID NO: 5)
and 5'-TGG AGA TGG CGG GAA TCG AAC-3';     (SEQ ID NO: 6)
and primer set D
(based on C. tepidum tmRNA termini):
5'-GGG GAT GAC AGG CTA TCG ACA-3'      (SEQ ID NO: 7)
and

5'-TGG AGA TGG CGG GAC TTG AAC-3'.     (SEQ ID NO: 8)
```

3. PCR Reaction

Sequences of tmRNA genes were obtained by polymerase chain reaction (PCR) in 25 μL using 40 ng of genomic DNA per reaction. The following general scheme was utilized for all of the sequences:

(a) 94° C. to 96° C. for 4 min. (first denaturation of genomic DNAs, done only once); then (b) 35 to 40 PCR cycles with 2.5 to 5 Units of Taq DNA polymerase in a 25 μL reaction volume, according to the following scheme (40 ng of genomic DNAs/PCR reaction):

1. denature at 94° to 96° C. for 25 to 30 sec;

2. anneal at 44° to 55° C. for 20 to 30 sec; and 3. extension at 72° C. for 10 sec.

The magnesium conc. was optimized for each phyla from 3.5 to 13.5 mM.

4. Elution of Amplified DNAs

The various PCR-amplified tmDNA bands were gel purified (5% PAGE), stained (ethidium bromide staining), cut using a sterile razor blade, and shaken over-night (passive elution, using a vibrator) in a 350 μl solution containing 10 mM Tris-HCl buffer (pH 8.1). The following day, the PCR amplified tmDNAs were ethanol precipitated, washed in 70% ETOH, vacuum dried and the DNA pellets were dissolved in 18 μl of RNase-DNase free sterile water.

5. DNA Sequencing

Six μL of amplified DNAs were added to 3.2 picomoles of the primer that was used in the PCR. To verify the novel tmDNA sequences, each of the two primers were used independently to sequence each of the two PCR-amplified DNA strands. Some tmDNAs were already engineered at their 5'-ends with a T7 promoter, to be able to transcribe directly the tmDNAs into tmRNAs by in vitro transcription.

Dye terminator sequencing was achieved at the DNA sequencing facility of the Human Genetics Institute. In addition to novel tmRNA sequences that are not available publicly, several tmDNA sequences that were already known have been verified and several sequencing mistakes have been found and corrected (especially for *Alcaligenes eutrophus* tmRNA).

Example 2

Amplification Reactions for Eubacterial tmDNA

Eubacterial tmDNA was amplified by PCR in accordance with Example 1, using the following conditions.

*Acidobacterium:*
Primer Set B; Annealing temp. during PCR: 53° C. for 20 sec; $Mg^{2+}$ conc.: 4.5 mM.

*Coprothermobacter:*
Primer Set B; Annealing temp. during PCR: 55° C. for 30 sec; $Mg^{2+}$ conc.: 5.5 mM.

*Cytophagales:*
Primer Set A; Annealing temp. during PCR: 46° C. for 30 sec; $Mg^{2+}$ conc.: 4.5 mM.

*Dictyoglomus:*
Primer set B; Annealing temp. during PCR: 55° C. for 30 sec; $Mg^{2+}$ conc.: 4.5 mM.

Environmental Samples:
Sludge DNA
Primer set C; Annealing temp. during PCR: 51° C. for 20 sec; $Mg^{2+}$ conc.: 13.5 mM.
Rumenal Fluid DNA
Primer set D; Annealing temp. during PCR: 50° C. for 30 sec; $Mg^{2+}$ conc.: 9.5 mM.

*Fibrobacter:*
Primer set A; Annealing temp. during PCR: 51° C.; $Mg^{2+}$ conc.: 3.5 mM.

*Firmicutes:*
Fusobacteria:
Primer set A; Annealing temp. during PCR: 52° C.; $Mg^{2+}$ conc.: 5.5 mM.
High G-C:
Primer set A; Annealing temp. during PCR: 50-55° C.; $Mg^{2+}$ conc.: 4.5 mM.
Low G-C:
Primer sets A or B; Annealing temp. during PCR: 52° C.; $Mg^{2+}$ conc.: 5.5 to 7.5 mM.
Mycoplasmes:
Primer set A; Annealing temp. during PCR: 52° C.; $Mg^{2+}$ conc.: 3.5 to 5.5 mM.

Green Non-Sulfur:
Primer sets A or B; Annealing temp. during PCR: 46 to 52° C.; $Mg^{2+}$ conc.: 4.5 mM.

Green Sulfur:
Primer set A; Annealing temp. during PCR: 46° C.; $Mg^{2+}$ conc.: 4.5 mM.

*Planctomycetales:*
Primer set A; Annealing temp. during PCR: 48 to 52° C.; $Mg^{2+}$ conc.: 7.5 mM.

*Proteobacteria:*
beta:
Primer sets A and/or B; Annealing temp. during PCR: 50° C. for 25 sec; $Mg^{2+}$ conc.: 3.5 mM.
delta:
Primer set B; Annealing temp. during PCR: 55° C.; $Mg^{2+}$ conc.: 3.5 to 4.5 mM.
epsilon:
Primer set A; Annealing temp. during PCR: 46° C. for 30 sec; $Mg^{2+}$ conc.: 3.5 mM.
gamma:
Primer set A; Annealing temp. during PCR: 44° C. for 30 sec; $Mg^{2+}$ conc.: 5.5 mM.

*Spirochetes:*
Primer set A; Annealing temp. during PCR: 52° C.; $Mg^{2+}$ conc.: 4.5 mM.

*Thermodesulfobacterium:*
Primer set B; Annealing temp. during PCR: 55° C.; $Mg^{2+}$ conc.: 5.5 mM.

Thermotogales:

Primer set B; Annealing temp. during PCR: 46° C.; Mg$^{2+}$ conc.: 7.5 mM.

Deinococcales:

Primer set B; Annealing temp. during PCR: 52° C.; Mg$^{2+}$ conc.: 3.5 mM.

Verrucomicrobia:

Primer set A; Annealing temp. during PCR: 53° C. for 25 sec; Mg$^{2+}$ conc.: 3.5 mM.

Example 3

Amplification of Eubacterial tmDNA

Figure 1A:
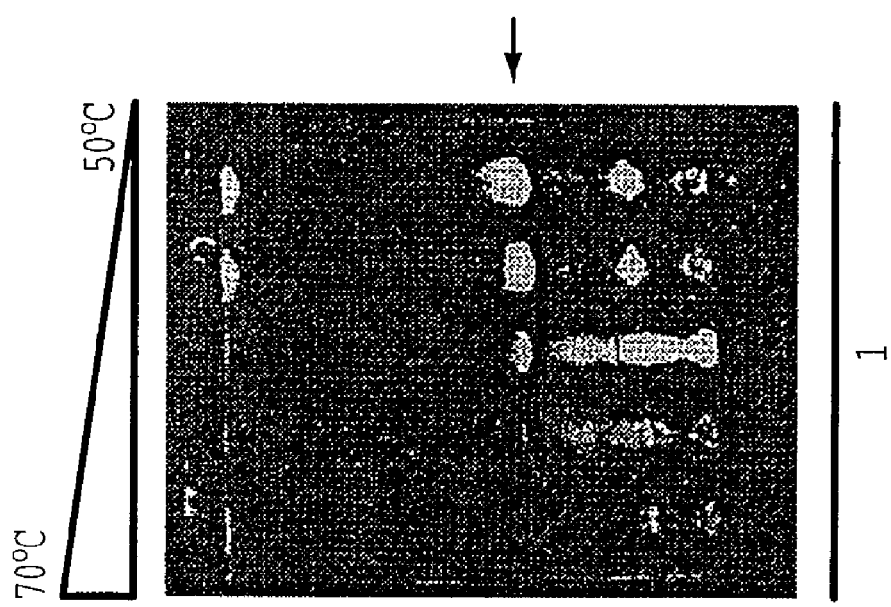

Specific PCR amplification of tmRNA genes was achieved for both thermophilic and mesophilic eubacterial tmRNA genes. For the novel tmDNA genes found in thermophiles, both the magnesium concentration and the annealing temperature (FIG. 1A) were optimized. As shown in FIG. 1A, a specific amplification of *Thermus aquaticus* tmDNA was observed with an annealing temperature around 50° C., whereas at higher temperatures there is a gradual decrease in the amount of amplified tmDNA. For mesophiles, the magnesium concentration during PCR was critical (FIG. 1B), but the annealing temperature could vary from 44° C. to 60° C. without significant effects on the amplification. FIG. 1B shows various effects of increasing the magnesium concentration on the PCR amplification of three novel eubacterial tmDNA genes. Increasing magnesium concentration from 3.5 mM to 5.5 mM has either a negative (FIG. 1B, panel 1), a positive (FIG. 1B, panel 2) or no effect on specifically amplifying eubacterial tmDNA genes.

Figure 2:
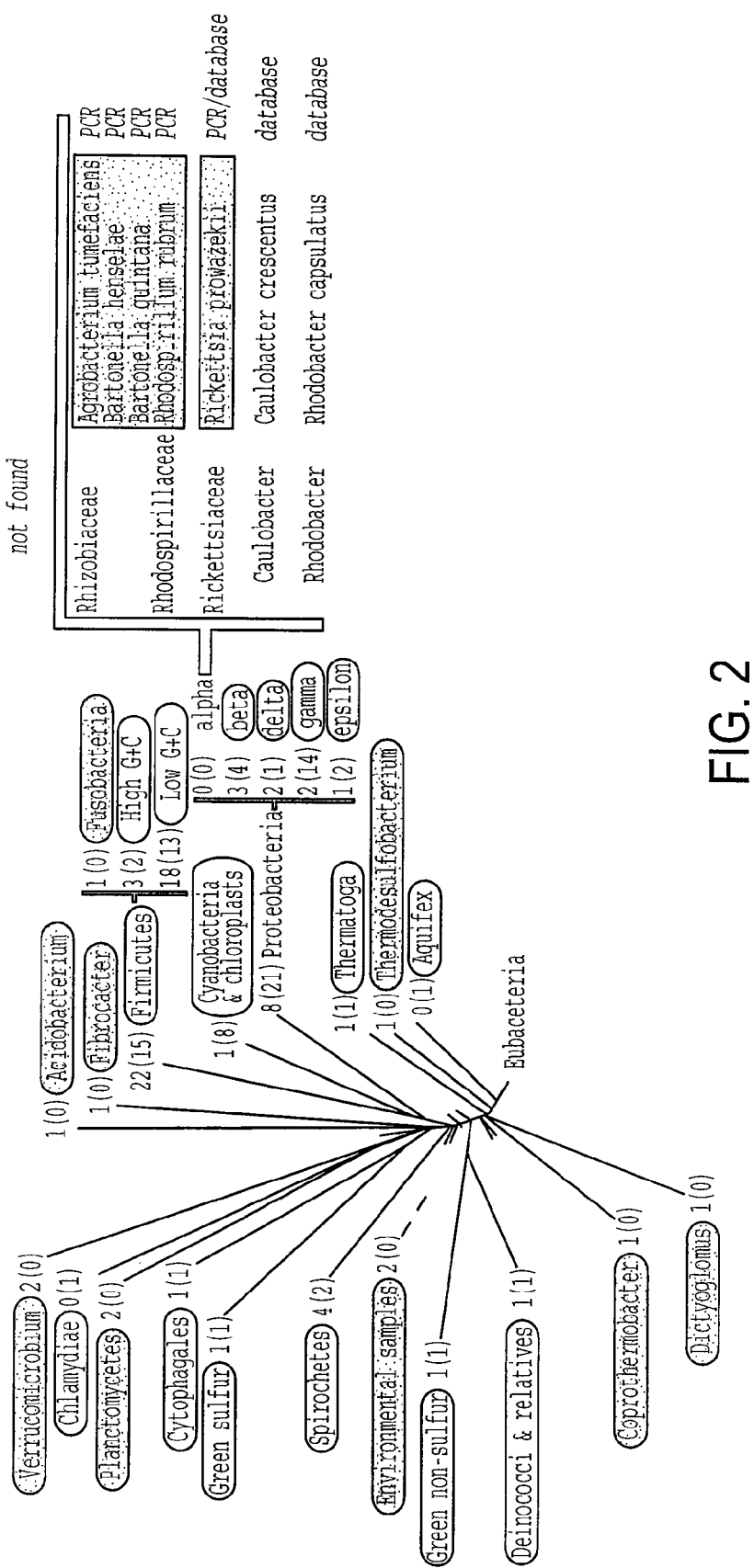
FIG. 2 shows the distribution of tmDNA sequences within eubacterial genomes. The circled phyla or subgroups contain tmDNA sequences and those shaded are new members of this category. The numbers shown close to each phylum are the 51 tmDNA sequences that have are disclosed herein and the numbers in parenthesis are the 53 tmDNA sequences that were previously known (summarized in Williams, 1999; Wower and Zwieb, 1999). The environmental samples are indicated with a dashed line as their connection to the tree is unknown. The 5 alpha-Proteobacteria in which tmDNA sequences were not detected by PCR analysis are labeled "PCR" and the 3 analyzed by Blast search of the complete, or nearly complete, sequenced genomes are labeled "database".
Figure 3A:
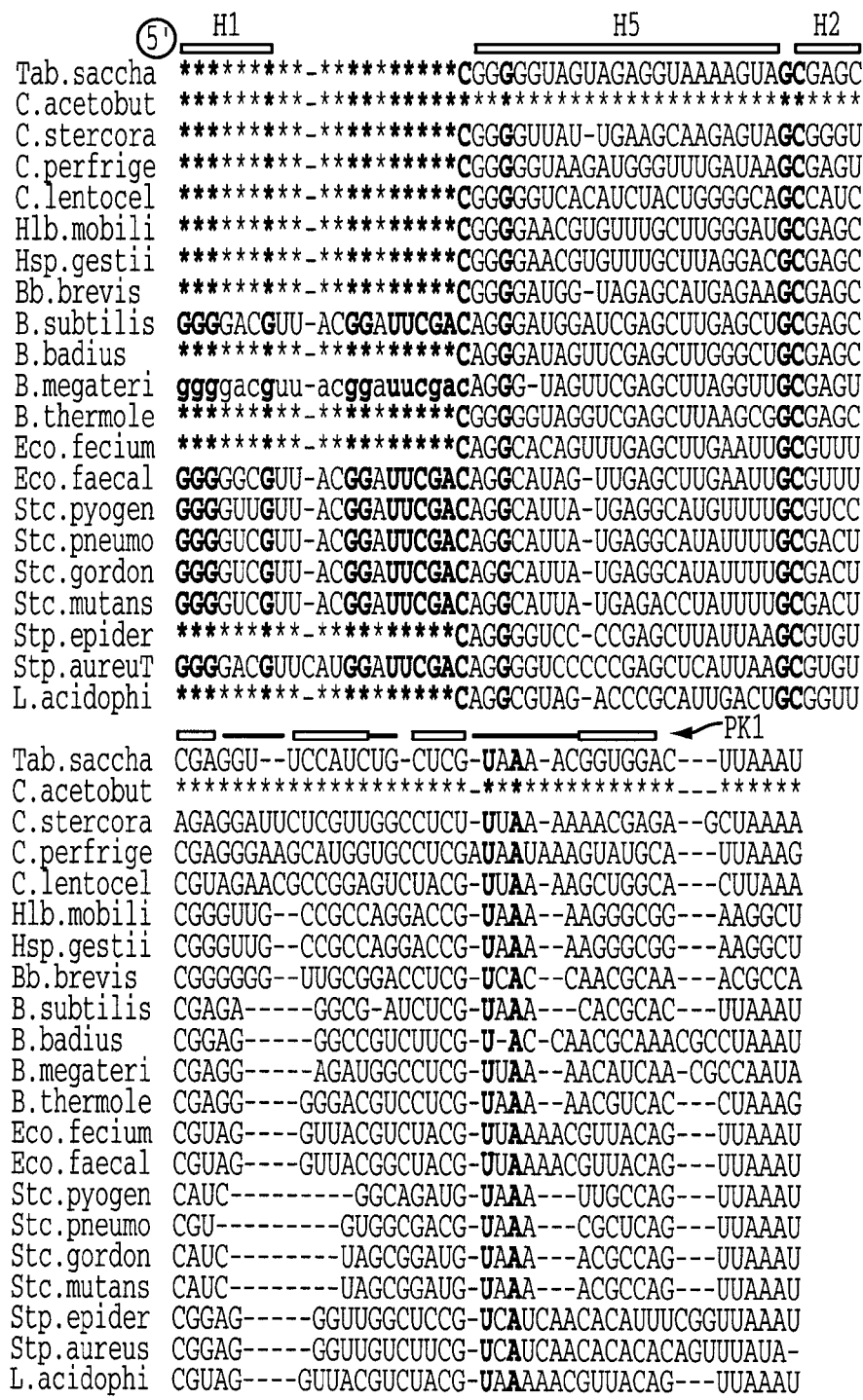
Figure 4A:
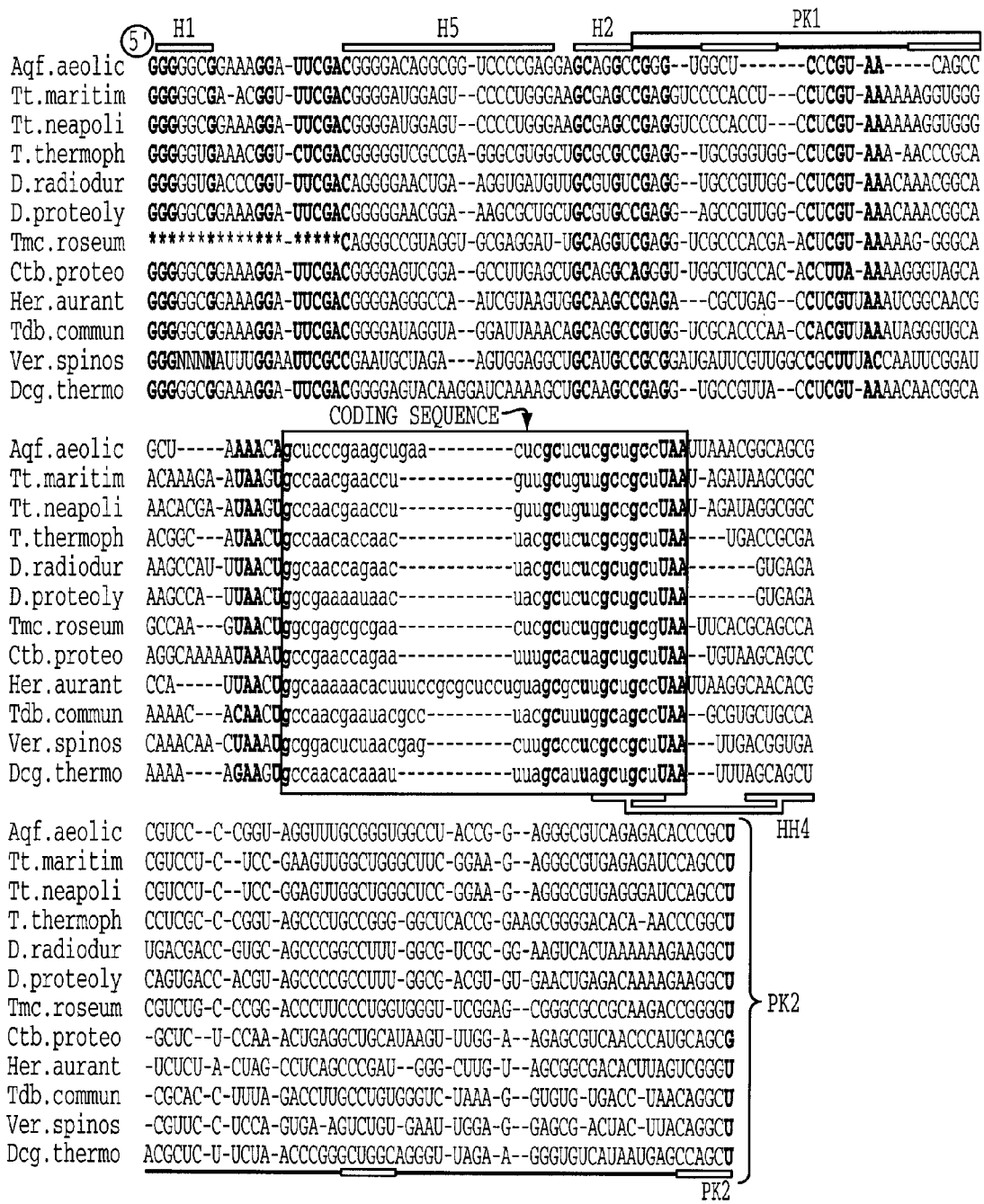
Figure 5A:
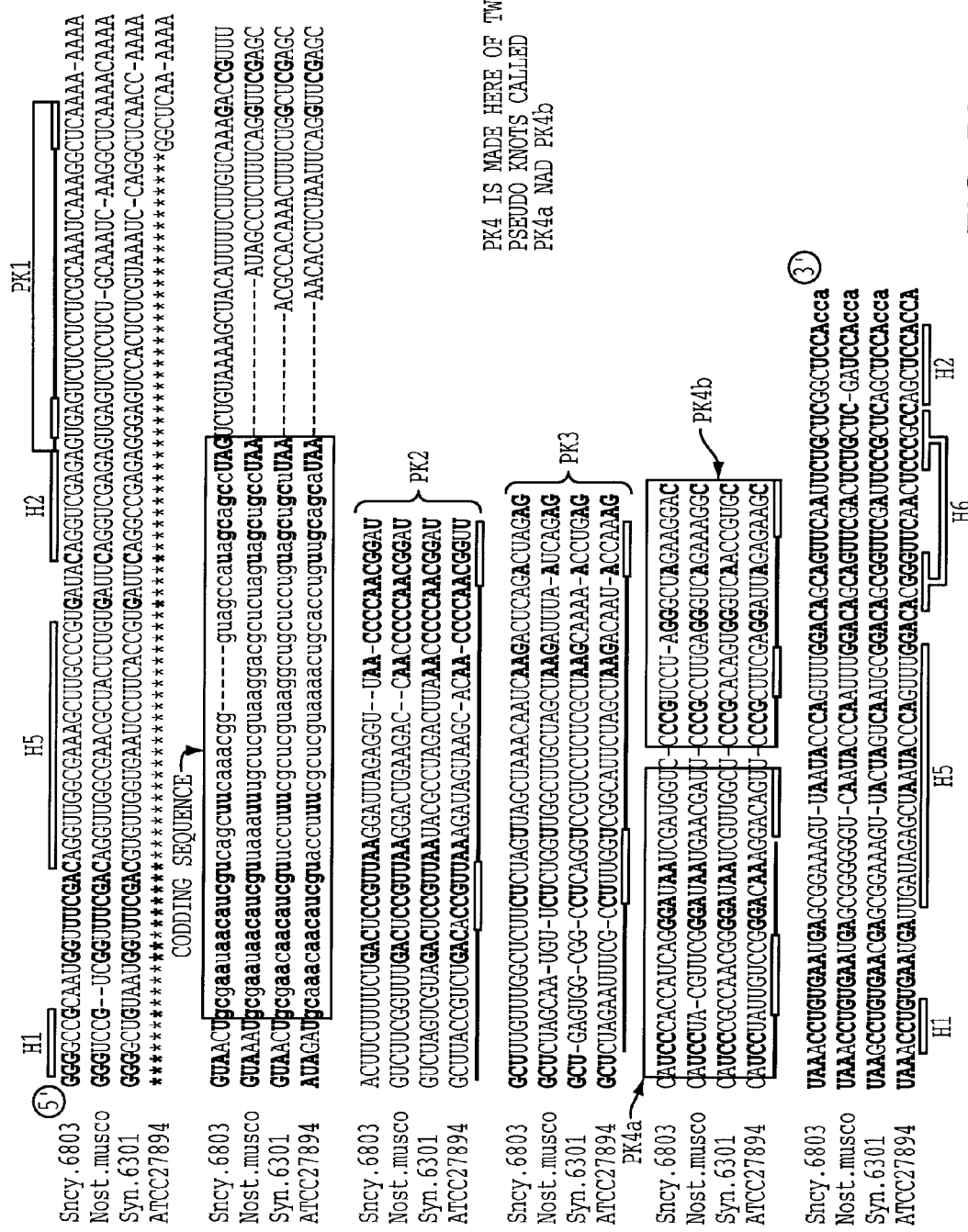
FIGS. 5A and 5B show the sequence alignment, structural domains and structural features for the tmRNA of several species of *Cyanobacteries* (5A) and chloroplasts (5B). The tmRNA sequences of the *Cyanobacteries* are set forth in SEQ ID NOs: 100-103, and the tmRNA sequences of the chloroplasts are set forth in SEQ ID NOs:104-108.
Figure 5B:
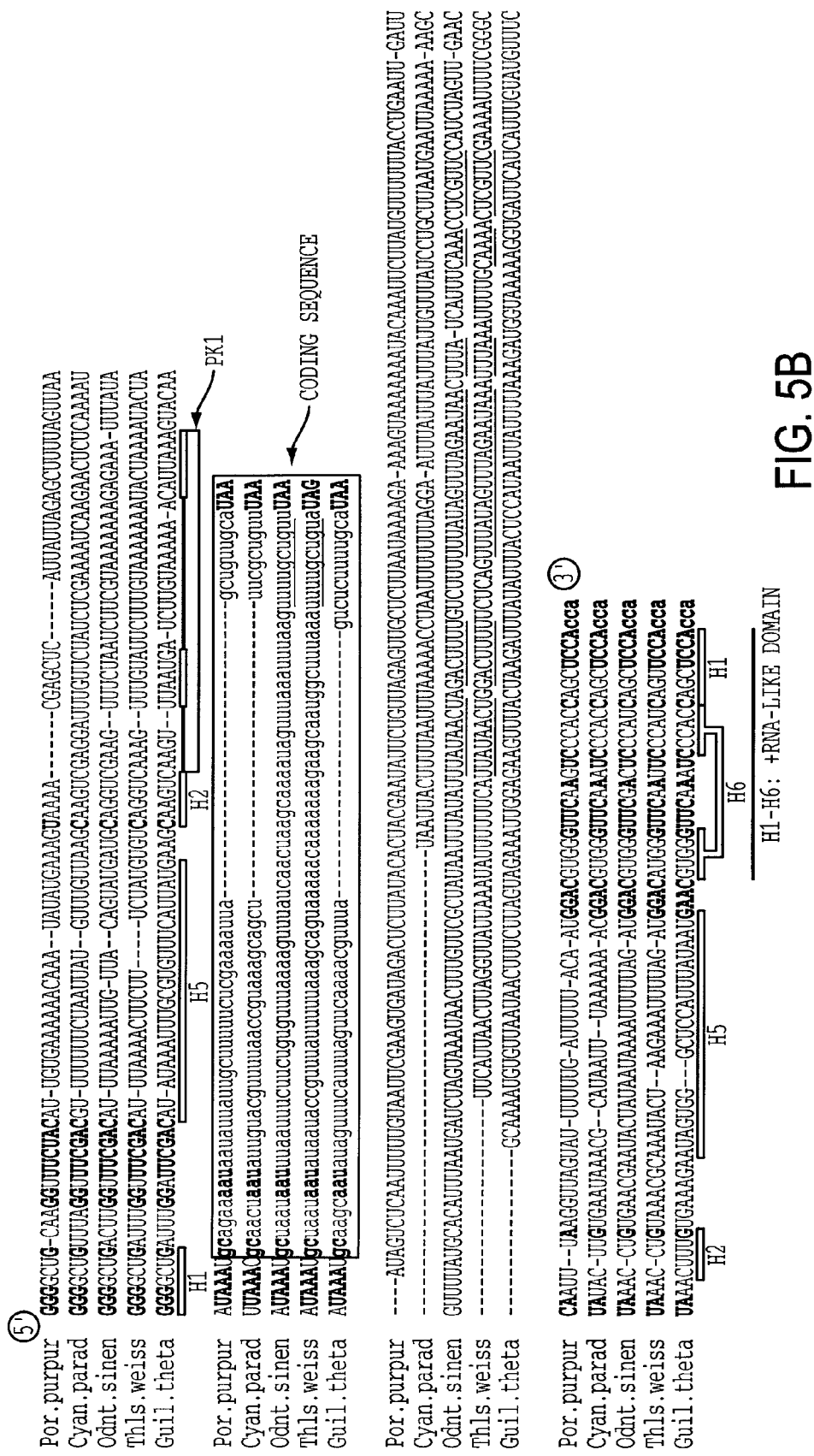
Figure 6A:
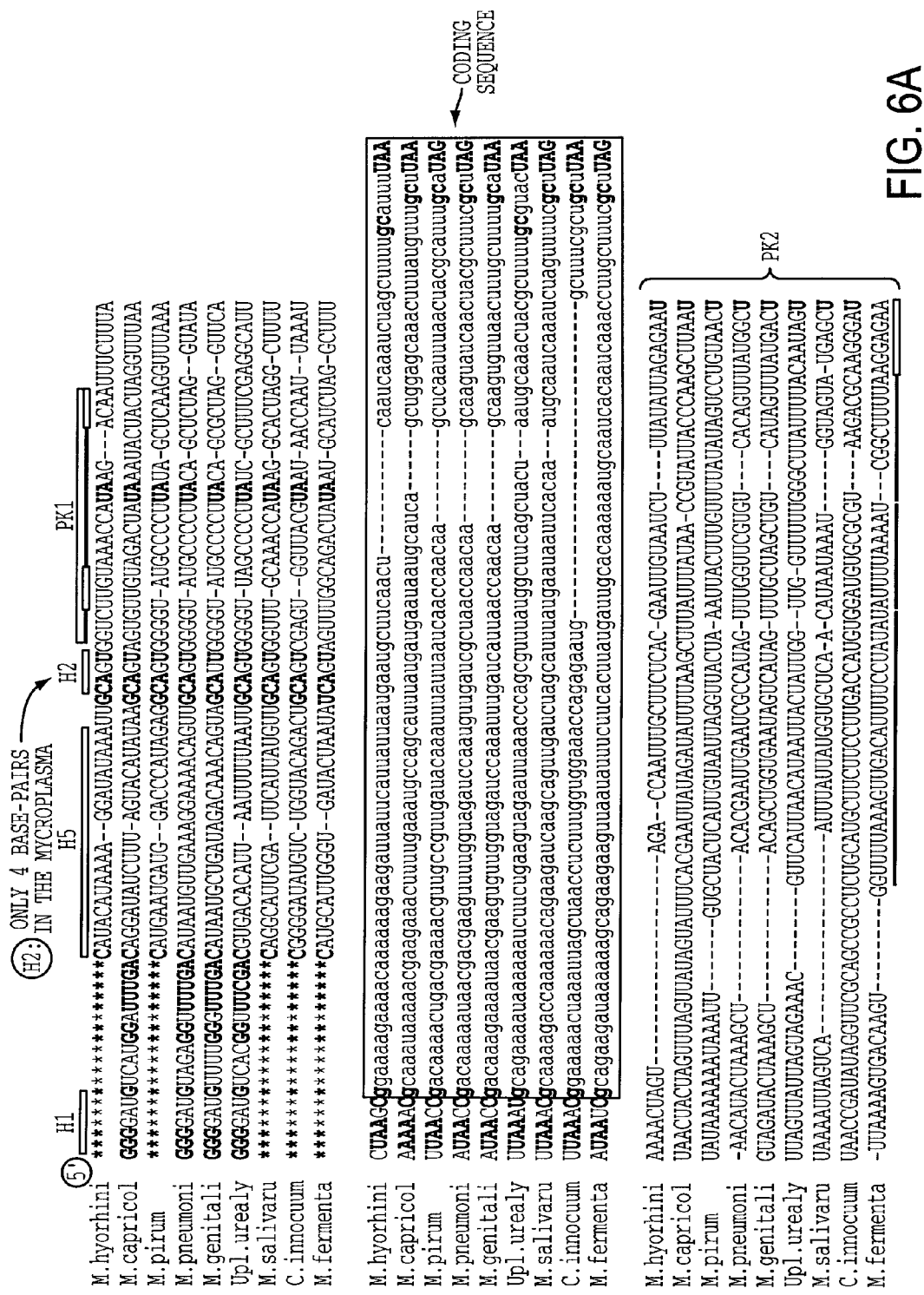
FIGS. 6A and 6B show the sequence alignment, structural domains and structural features for the tmRNA of several species of *Mycoplasmes*. The tmRNA sequences are set forth in SEQ ID NOs:109-117.
Figure 6B:
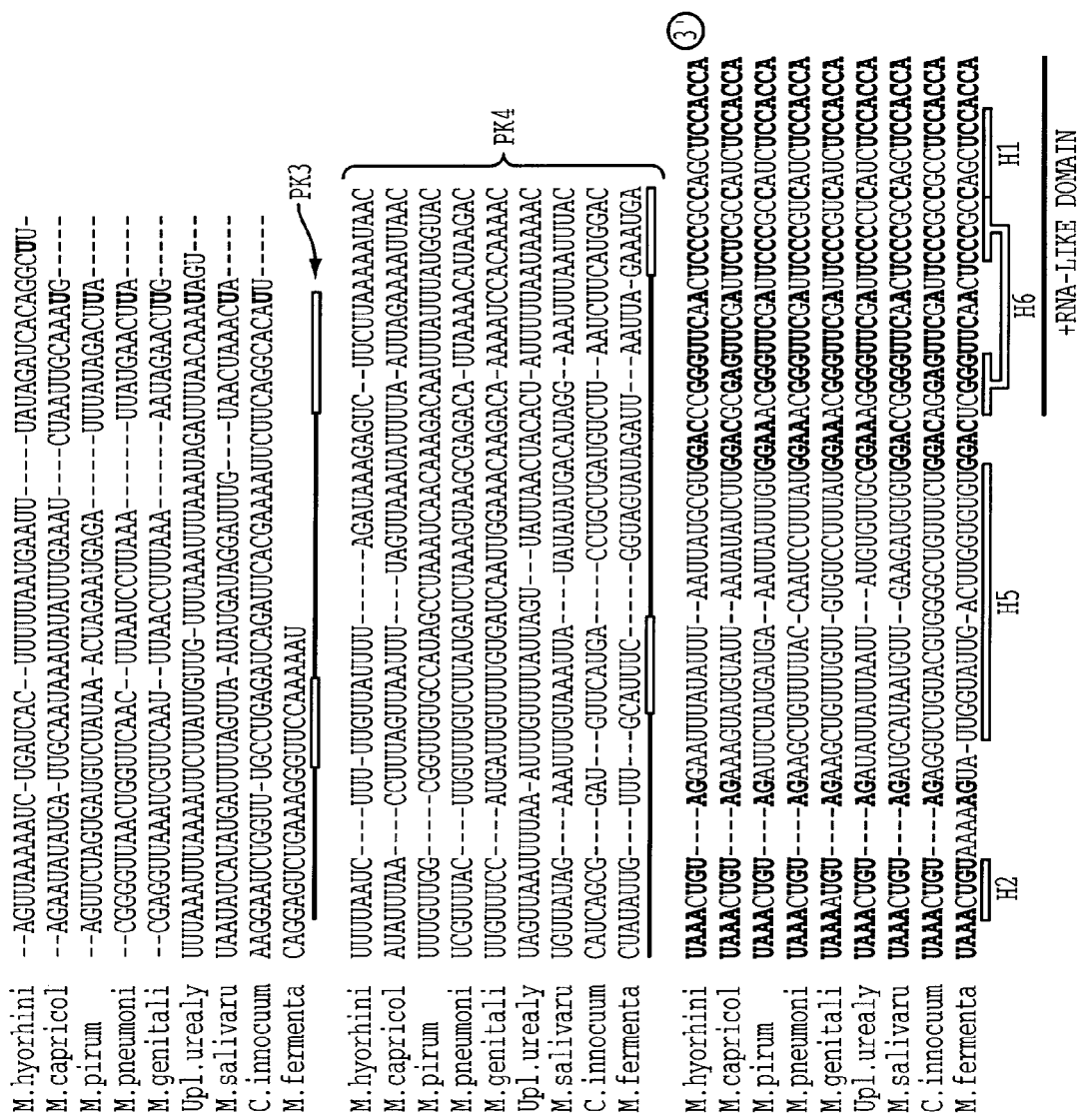
Figures 1, 7A:
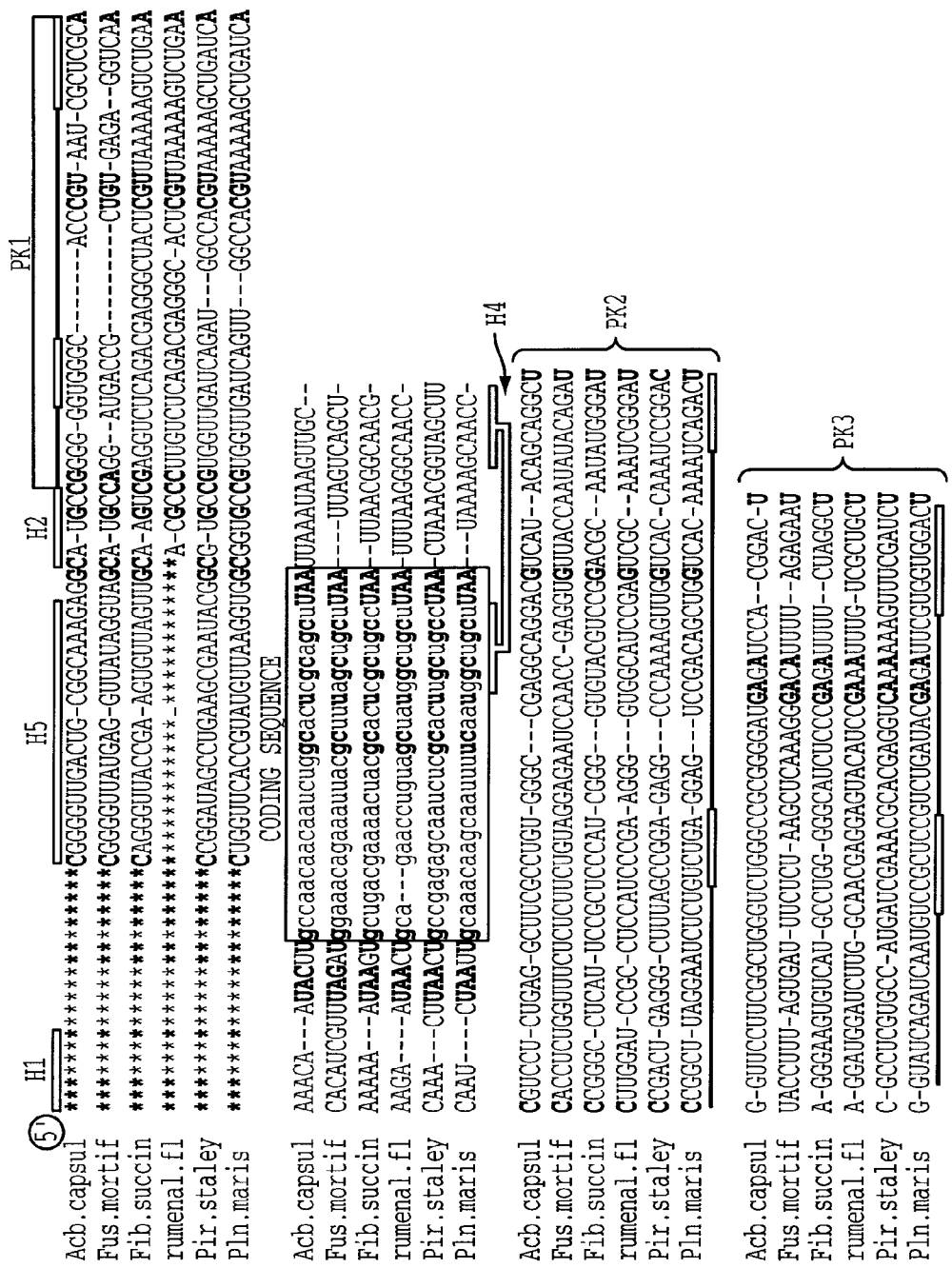
Figure 7C:
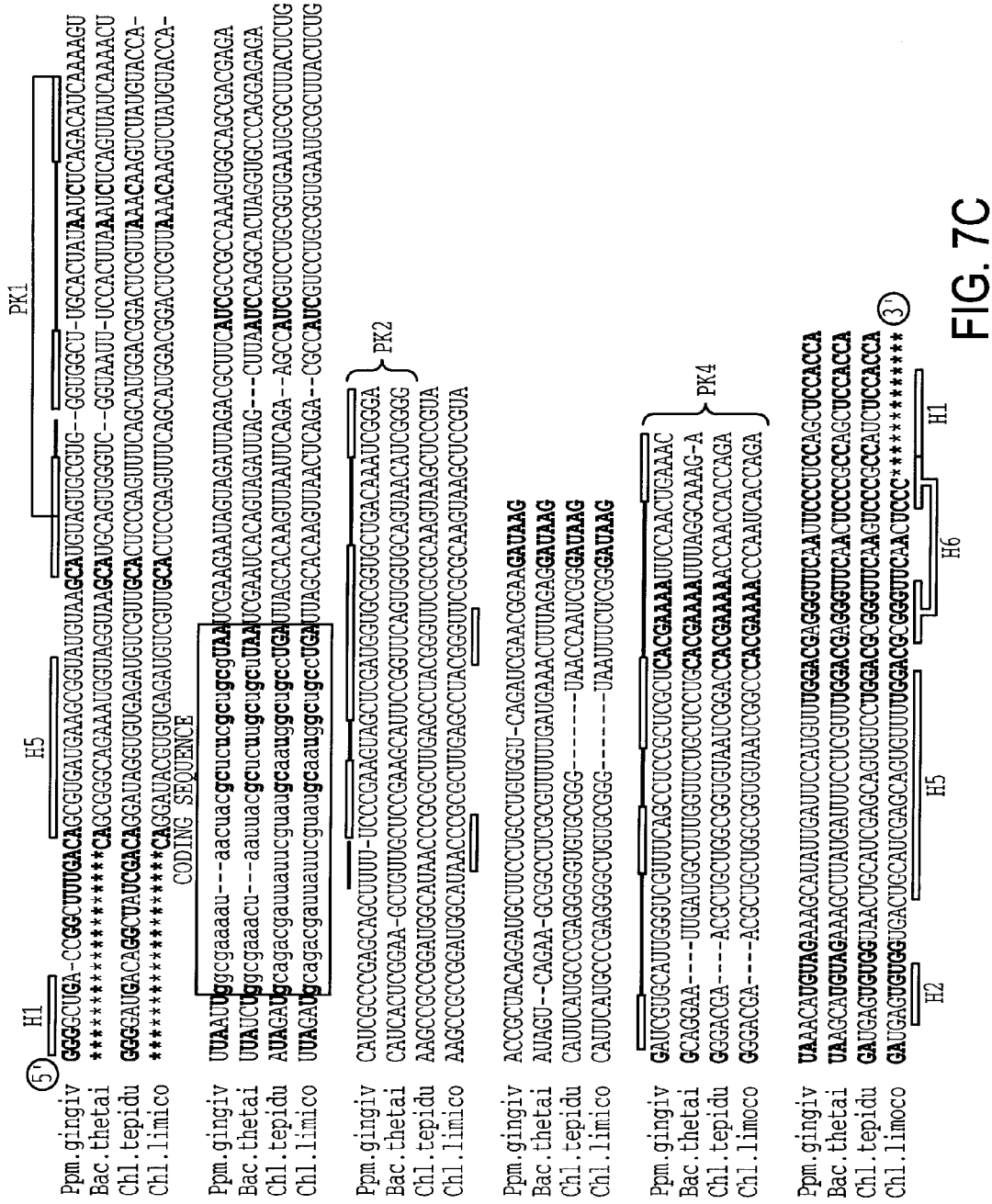
Figure 8A:
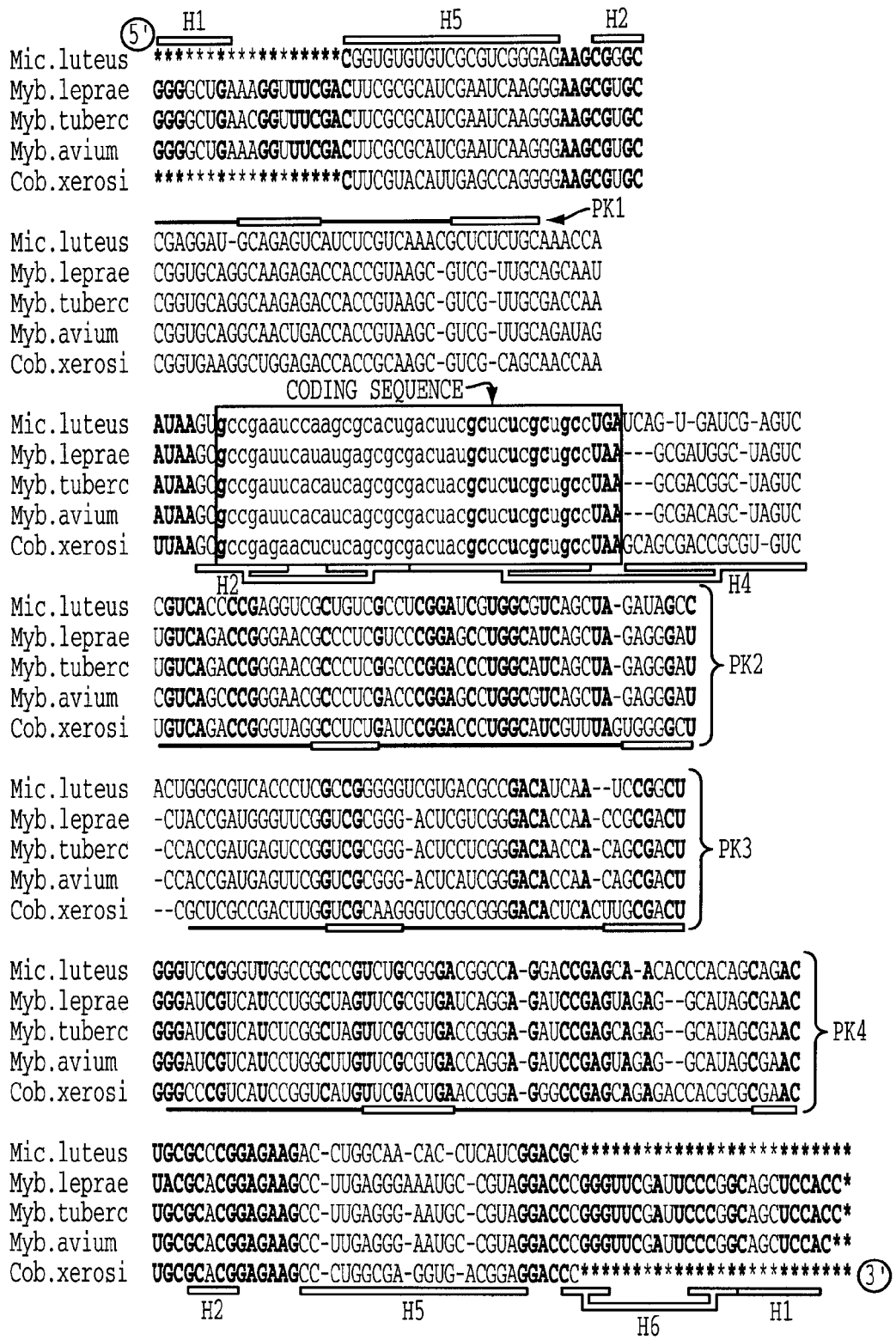
Figure 9A:
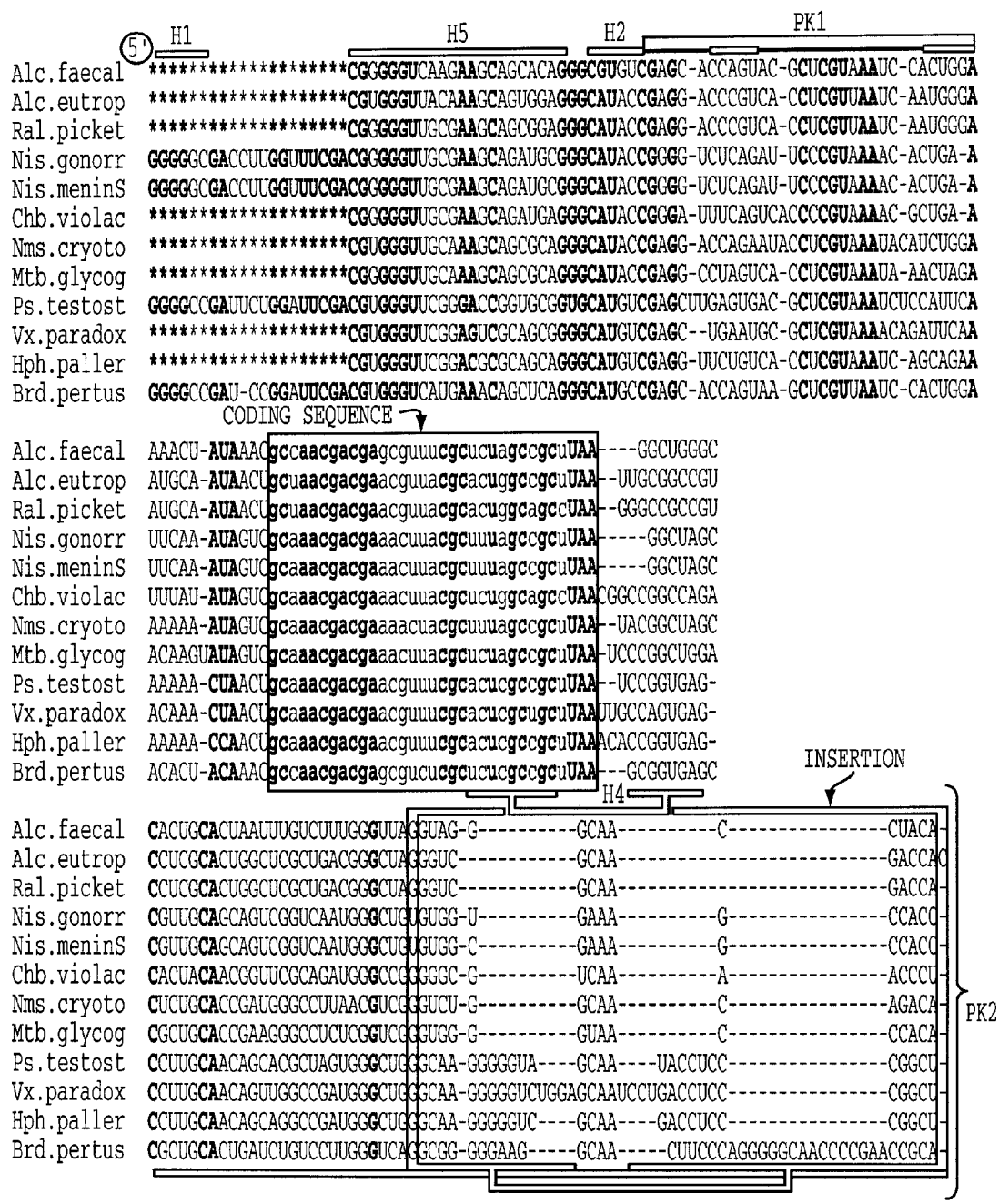
Figure 11A:
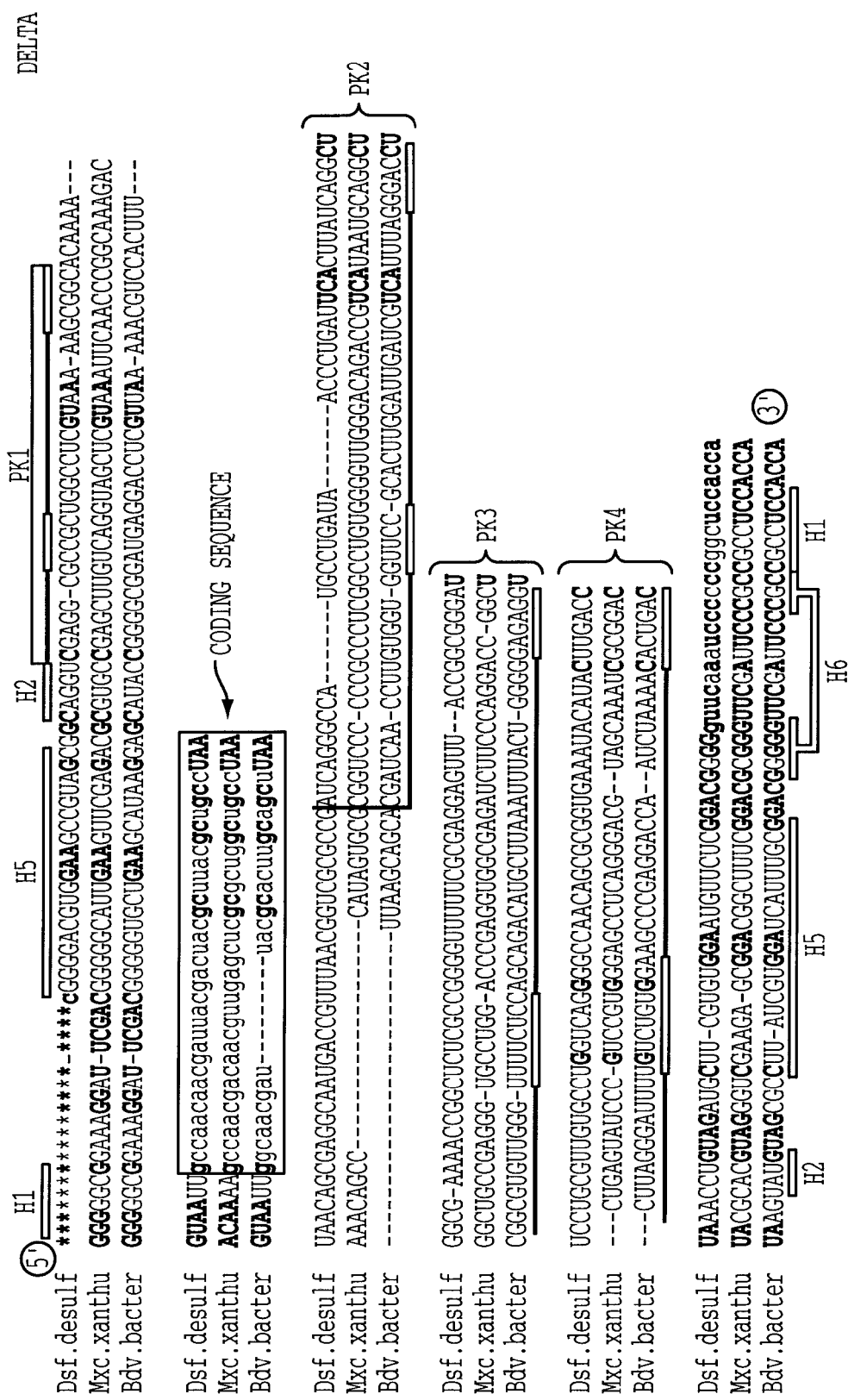
FIGS. 11A and 11B show the sequence alignment, structural domains and structural features for the tmRNA of several species of *Pourpres* delta (11A) and *Pourpres* epsilon (11B). The tmRNA sequences of the *Pourpres* delta are set forth in SEQ ID NOs:170-172, and the tmRNA sequences of the *Pourpres* epsilon are set forth in SEQ ID NOs:173-175.
Figure 11B:
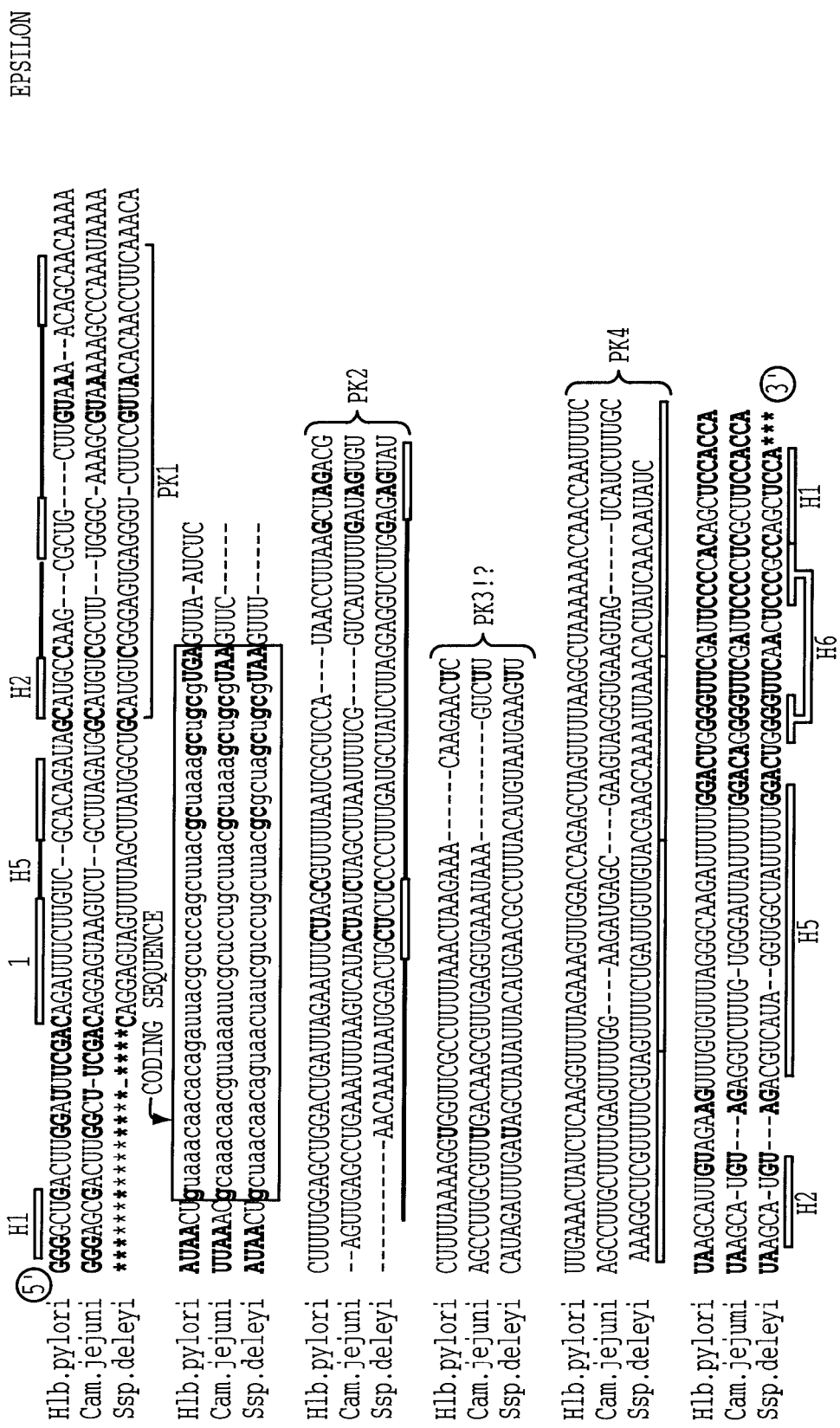

According to these procedures, tmRNA genes from many eubacteria including known human pathogens were amplified. The PCR was facilitated by sequence conservation at both 5' and 3' ends and was performed as described (Williams and Bartel, 1996), with modifications. This study was initiated to collect further sequences from eubacterial tmDNA genes, as well as to test experimentally whether tmDNA genes could be found in all bacterial phyla or subgroups. 51 new tmDNA sequences were determined (FIG. 2), including sequences from members of 8 additional phyla and 1 subgroup (shaded boxes in FIG. 2). The 58 new tmDNA sequences are set forth in Tables 1-58. This brings coverage to a total of 104 sequences in 19 bacterial phyla. Interestingly, tmDNA sequences could be amplified from all species tested apart from those in the alpha-Proteobacteria. Five genomic DNAs from alpha-Proteobacteria (*Agrobacterium tumefaciens, Bartonella henselae, Bartonella quintana, Rhodospirillum rubrum* and *Rickettsia prowazekii*) were extensively checked using various oligonucleotides, annealing temperatures and magnesium concentrations. No specific amplified tmDNA sequences were detected in this subgroup. Moreover, no putative tmDNA sequences could be identified (results herein and Williams, 1999) by Blast searches on the 1 fully sequenced (*Rickettsia prowazekii*) and 2 nearly completed (*Caulobacter crescentus* and *Rhodobacter capsulatus*) alpha-proteobacterial genomes (FIG. 2).

It cannot be ruled out that tmDNA sequences may have largely diverged in the alpha-proteobacterial sub-group compared to other bacterial phyla, and that both PCR methods and Blast searches are missing the relevant sequences. While tmRNA is dispensable in *E. coli* (Ando et al., 1996), it is striking that it has been found in all bacteria tested other than the alpha-Proteobacteria. The alpha-Proteobacteria have undergone reductive evolution. This has been more intensive in one of the two sub-classes than in the other (Gray and Spencer, 1996), but tmRNA sequences have not been found even in the sub-class with the larger genome. Based on sequence comparison, the alpha-Proteobacteria and mitochondria are evolutionary relatives (Yang et al., 1985; Andersson et al., 1998). The drastic downsizing in what has become mitochondrial genomes means that it is not reasonable to draw inferences on the relationship between alpha-Proteobacteria and mitochondria based on their mutual apparent absence of tmRNA. It is nevertheless, of interest, that at least some chloroplasts and cyanelle genomes have tmDNA sequences, and the cyanobacteria, with which they are evolutionary related, also have tmRNA.

TABLE 1 tmDNA Sequence for *Acidobacterium capsulatum* (Acidobacterium)

(SEQ ID NO: 9)
GGGGGCGGAAAGGATTCGACGGGGTTGACTGCGGCAAAGAGGCATGCCGG

GGGGTGGGCACCCGTAATCGCTCGCAAAACAATACTTGCCAACAACAATC

TGGCACTCGCAGCTTAATTAAATAAGTTGCCGTCCTCTGAGGCTTCGCCT

GTGGGCCGAGGCAGGACGTCATACAGCAGGCTGGTTCCTTCGGCTGGGTC

TGGGCCGCGGGGATGAGATCCACGGACTAGCATTCTGCGTATCTTGTCGC

TTCTAAGCGCAGAGTGCGAAACCTAAAGGAATGCGACTGAGCATGGAGTC

TCTTTTCTGACACCAATTTCGGACGCGGGTTCGATTCCCGCCGCCCTCCA

CCA

TABLE 2 tmDNA Sequence for *Coprothermobacter proteolyticus* (60 degrees)

(SEQ ID NO: 10)
GGGGGCGGAAAGGATTCGACGGGGAGTCGGAGCCTTGAGCTGCAGGCAGG

GTTGGCTGCCACACCTTAAAAAGGGTAGCAAGGCAAAAATAAATGCCGAA

CCAGAATTTGCACTAGCTGCTTAATGTAAGCAGCCGCTCTCCAAACTGAG

GCTGCATAAGTTTGGAAGAGCGTCAACCCATGCAGCGGCTCTTAAGCAGT

GGCACCAGCTGTTTAAGGGTGAAAAGAGTGGTGCTGGGCAGTGCGGTTGG

GCTTCCTGGGCTGCACTGTCGAGACTTCACAGGAGGGCTAAGCCTGTAGA

CGCGAAAGGTGGCGGCTCGTCGGACGCGGGTTCGATTCCCGCCGCCTCCA

CCA

TABLE 3 tmDNA Sequence for *Bacteroides thetaiotaomicron* (bacteroides/flavobacterium)

(SEQ ID NO: 11)
GGGGCTGATTCTGGATTCGACAGCGGGCAGAAATGGTAGGTAAGCATGCA

GTGGGTCGGTAATTTCCACTTAAATCTCAGTTATCAAAACTTTATCTGGC

GAAACTAATTACGCTCTTGCTGCTTAATCGAATCACAGTAGATTAGCTTA

ATCCAGGCACTAGGTGCCAGGACGAGACATCACTCGGAAGCTGTTGCTCC

GAAGCATTCCGGTTCAGTGGTGCAGTAACATCGGGGATAGTCAGAAGCGG

TABLE 3-continued tmDNA Sequence for *Bacteroides thetaiotaomicron* (bacteroides/flavobacterium)

CCTCGCGTTTTTGATGAAACTTTAGAGGATAAGGCAGGAATTGATGGCTT

TGGTTCTGCTCCTGCACGAAAATTTAGGCAAAGATAAGCATGTAGAAAGC

TTATGATTTCCTCGTTTGGACGAGGGTTCAACTCCCGCCAGCTCCACCA

TABLE 4 tmDNA Sequence for *Dictyoglomus thermophilum* (70 degrees)

(SEQ ID NO: 12)
GGGGCTGATTCTGGATTCGACAGGGAGTACAAGGATCAAAAGCTGCAAGC

CGAGGTGCCGTTACCTCGTAAAACAACGGCAAAAAAGAAGTGCCAACACA

AATTTAGCATTAGCTGCTTAATTTAGCAGCTACGCTCTTCTAACCCGGGC

TGGCAGGGTTAGAAGGGTGTCATAATGAGCCAGCTGCCCCTTCCGACTCC

CCTAAGGAAGGGAAAGATGTAGGGGATAGGTGCTTACAGAATCCTGCGGG

AGGGAGTCTGTAAGTGCCGAAAAGTTAAAACTCCCGCTAAGCTTGTAGAG

GCTTTTGATTCTTGCTCTCTGGACGCGGGTTCAACTCCCGCCAGCTCCAC

CA

TABLE 5 tmDNA Sequence for Environmental Sample from Rumenal Fluid (SEQ ID NO: 13)
ACGCCCTTGTCTCAGACGAGGGCACTCGTTAAAAAGTCTGAAAAGAATAA

CTGCAGAACCTGTAGCTATGGCTGCTTAATTTAAGGGCAACCCTTGGATC

CGCCTCCATCCCGAAGGGGTGGCATCCGAGTCGCAAATCGGGATAGGATG

GATCTTGGCAACGAGGAGTACATCCGAAATTTGTCGCTGCTGGCTGAAGC

ATCGCCGTTCCTCTTTGGGCGTGGCAAGGCAAGATTAAATTCAGAGGATA

AGCGTGTAGTAGCGAGTGAGTAGGTGTTTTTGGACGCGGGTTCAAGTCCC

GCCATCTCCACCA

TABLE 6 tmDNA Sequence for Environmental Sample from Sludge (SEQ ID NO: 14)
GGGGATGTCATGGTTTTGACAGGGAACCAGGAGGTGTGAGATGCATGCCG

GAGACGCTGTCCGCTCCGTTATCAAGCAGCAAACAAAACTAATTGCAAAC

AACAATTACTCCTTAGCAGCGTAAGCAGCTAACGTTCAACCTCTCCGGAC

CGCCGGGAGGGGATTTGGGCGTCGAAACAGCGCGGACGCTCCGGATAGGA

CGCCCATAATATCCGGCTAAGACCATGGGTCTGGCTCTCGCGGGTCTGAT

TGTCTTCCACCGCGCGGGCCGCGATCAAAGACAACTAAGCATGTAGGTTC

TTGCATGGCCTGTTCTTTGGACGCGGGTTCGATTCCCGCCATCTCCACCA

TABLE 7 tmDNA Sequence for *Fibrobacter succinogenes* (Fibrobacter)

(SEQ ID NO: 15)
GGGGCTGATTCTGGATTCGACAGGGTTACCGAAGTGTTAGTTGCAAGTCG

AGGTCTCAGACGAGGGCTACTCGTTAAAAAGTCTGAAAAAAAATAAGTGC

TGACGAAAACTACGCACTCGCTGCCTAATTAACGGCAACGCCGGGCCTCA

TTCCGCTCCCATCGGGGTGTACGTCCGGACGCAATATGGGATAGGGAAGT

GTCATGCCTGGGGCATCTCCCGAGATTTTCTAGGCTGGTCAAACTCCGC

GCCGACCTTCTTGGGCGTGGATAAGACGAGATCTTAAATTCGAAGGGAAC

ACTTGTAGGAACGTACATGGACGTGATTTTGGACAGGGGTTCAACTCCCG

CCAGCTCCA

TABLE 8 tmDNA Sequence for *Fusobacterium mortferum*

(SEQ ID NO: 16)
GGGGCTGATTCTGGATTCGACGGGGTTATGAGGTTATAGGTAGCATGCCA

GGATGACCGCTGTGAGAGGTCAACACATCGTTTAGATGGAAACAGAAATT

ACGCTTTAGCTGCTTAATTAGTCAGCTCACCTCTGGTTTCTCTCTTCTGT

AGGAGAATCCAACCGAGGTGTTACCAATATACAGATTACCTTTAGTGATT

TCTCTAAGCTCAAAGGGACATTTTAGAGAATAGCTTCAGTTAGCCCTGTC

TGCGGGAGTGATTGTTGCGAAATAAAATAGTAGACTAAGCATTGTAGAAG

CCTATGGCGCTGGTAGTTTCGGACACGGGTTCAACTCCCGCCAGCTCCAA

TABLE 9 tmDNA Sequence for *Corynebacterium xerosis* (gram +, high G-C content)

(SEQ ID NO: 17)
GGGGCTGATTCTGGATTCGACTTCGTACATTGAGCCAGGGGAAGCGTGCC

GGTGAAGGCTGGAGACCACCGCAAGCGTCGCAGCAACCAATTAAGCGCCG

AGAACTCTCAGCGCGACTACGCCCTCGCTGCCTAAGCAGCGACCGCGTGT

CTGTCAGACCGGGTAGGCCTCTGATCCGGACCCTGGCATCGTTTAGTGGG

GCTCGCTCGCCGACTTGGTCGCAAGGGTCGGCGGGGACACTCACTTGCGA

CTGGGCCCGTCATCCGGTCATGTTCGACTGAACCGGAGGGCCGAGCAGAG

ACCACGCGCGAACTGCGCACGGAGAAGCCCTGGCGAGGTGACGGAGGACC

CGGGTTCAACTCCCGCCAGCTCCACCA

TABLE 10 tmDNA Sequence for *Micrococcus luteus* (parfait)

(SEQ ID NO: 18)
GGGGCTATTCTGGATTCGACGGTGTGTGTCGCGTCGGGAGAAGCGGGCCG

AGGATGCAGAGTCATCTCGTCAAACGCTCTCTGCAAACCAATAAGTGCCG

AATCCAAGCGCACTGACTTCGCTCTCGCTGCCTGATCAGTGATCGAGTCC

TABLE 10-continued tmDNA Sequence for *Micrococcus luteus* (parfait)

GTCACCCCGAGGTCGCTGTCGCCTCGGATCGTGGCGTCAGCTAGATAGCC

ACTGGGCGTCACCCTCGCCGGGGGTCGTGACGCCGACATCAATCCGGCTG

GGTCCGGGTTGGCCGCCCGTCTGCGGGACGGCCAGGACCGAGCAACACCC

ACAGCAGACTGCGCCCGGAGAAGACCTGGCAACACCTCATCGGACGCGGG

TTCAACTCCCGCANTCCCACCA

TABLE 11 tmDNA Sequence for *Mycobacterium smegmatis*

(SEQ ID NO: 19)
TCATCTCGGCTTGTTCGCGTGACCGGGAGATCCGAGTAGAGACATAGCGA

ACTGCGCACGGAGAGGGGCTGATTCCTGGATTCGACTTCGAGCATCGAAT

CCAGGGAAGCGTGCCGGTGCAGGCAAGAGACCACCGTAAGCGTCGTTGCA

ACCAATTAAGCGCCGATTCCAATCAGCGCGACTACGCCCTCGCTGCCTAA

GCGACGGCTGGTCTGTCAGACCGGGAGTGCCCTCGGCCCGGATCCTGGCA

TCAGCTAGAGGGACCCACCCACGGGTTCGGTCGCGGGACCTGTGGGGACA

TCAAACAGCGACTGGGATCGAGCCTCGAGGACATGCCGTAGGACCCGGGT

TCAACTCCCGCCAGCTCCACCA

TABLE 12 tmDNA Sequence for *Bacillus badius*

(SEQ ID NO: 20)
GGGGGTGATTCTGGATTCGACAGGGATAGTTCGAGCTTGGGCTGCGAGCC

GGAGGGCCGTCTTCGTACCAACGCAAACGCCTAAATATAACTGGCAAAAA

AGATTTAGCTTTAGCTGCCTAATATAGGTTCAGCTGCTCCTCCCGCTATC

GTCCATGTAGTCGGGTAAGGGGTCCAAACTTAGTGGACTACGCCGGAGTT

CTCCGCCTGGGACAAAGGAAGAGATCAATCAGGCTAGCTGCCCGGACGC

CCGTCGATAGGCAAAAGGAACAGTGAACCCCAAATATATCGACTACGCTC

GTAGACGTTCAAGTGGCGTTATCTTTGGACGTGGGTTCAACTCCCGCCAG

CTCCA

TABLE 13 tmDNA Sequence for *Bacillus brevis*

(SEQ ID NO: 21)
GGGGGCGGAAAGGATTCGACGGGGATGGTAGAGCATGAGAAGCGAGCCGG

GGGGTTGCGGACCTCGTCACCAACGCAAACGCCATTAACTGGCAACAAAC

AACTTTCTCTCGCTGCTTAATAACCAGTGAGGCTCTCCCACTGCATCGGC

CCGTGTGCCGTGGATAGGGCTCAACTTTAACGGGCTACGCCGGAGGCTTC

CGCCTGGAGCCAAAGGAAGAAGACCAATCAGGCTAGGTGCCAGGTCAGCG

CGTCACTCCGCGAATCTGTCACCGAAACTCTAAACGAGTGACTGCGCTCG

TABLE 13-continued tmDNA Sequence for *Bacillus brevis*

GAGATGCTCATGTATCGCTGTTTTCGGACGGGGGTTCGATTCCCGCCGCC

TCACCCA

TABLE 14 tmDNA Sequence for *Bacillus thermoleovorans* (50-60 degres)

(SEQ ID NO: 22)
GGGGGCGGAAAGGATTCGACGGGGTAGGTCGAGCTTAAGCGGCGAGCCG

AGGGGGACGTCCTCGTAAAAACGTCACCTAAAGATAACTGGCAAACAAAA

CTACGCTTTAGCTGCCTAATTGCTGCAGCTAGCTCCTCCCGCCATCGCCC

GCGTGGCGTTCGAGGGGCTCATATGGAGCGGGCTACGCCCAAATCCGCCG

CCTGAGGATGAGGGAAGAGACGAATCAGGCTAGCCGCCGGGAGGCCTGTC

GGTAGGCGGAACGGACGGCGAAGCGAAATATACCGACTACGCTCGTAGAT

GCTTAAGTGGCGATGCCTCTGGACGTGGGTTCGATTCCCGCCGCCTCCCC

ACCA

TABLE 15 tmDNA Sequence for *Clostridium innocuum*

(SEQ ID NO: 23)
GGGGGCGGAAAGGATTCGACGGGGATATGTCTGGTACAGACTGCAGTCGA

GTGGTTACGTAATAACCAATTAAATTTAAACGGAAAAACTAAATTAGCTA

ACCTCTTTGGTGGAAACCAGAGAATGGCTTTCGCTGCTTAATAACCGATA

TAGGTTCGCAGCCGCCTCTGCATGCTTCTTCCTTGACCATGTGGATGTGC

GCGTAAGACGCAAGGGATAAGGAATCTGGTTTGCCTGAGATCAGATTCAC

GAAAATTCTTCAGGCACATTCATCAGCGGATGTTCATGACCTGCTGATGT

CTTAATCTTCATGGACTAAACTGTAGAGGTCTGTACGTGGGGCTGTTTCT

GGACAGGAGTTCGATTCCCGCCGCCTCACCACCA

TABLE 16 tmDNA Sequence for *Clostridium lentocellum*

(SEQ ID NO: 24)
GGGGGCGGAAAGGATTCGACGGGGGTCACATCTACTGGGGCAGCCATCCG

TAGAACGCCGGAGTCTACGTTAAAAGCTGGCACTTAAAGTAAACGCTGAA

GATAATTTAGCAATCGCTGCCTAATTAAGGCGCAGTCCTCCTAGGTCTTC

CGCAGCCTAGATCAGGGCTTCGACTCGCGGATCCTTCACCTGGCAAAGCT

TTGAGCCAACGTGAACACTATGAAGCTACTAAAATCTAGAGCCTGTCTTT

GGGCGCTAGATGGAGGGAATGTCAAAACAAAGAATATGATGGTAGAGACC

ACGCTATATGGGCTTTCGGACAGGGGTTCGATTCCCGCCGCCTTCACCA

TABLE 17

| tmDNA Sequence for *Clostridium perfringens* |
|---|
| (SEQ ID NO: 25) |
| GGGGCTGATTCTGGATTCGACGGGGGTAAGATGGGTTTGATAAGCGAGTC |
| GAGGGAAGCATGGTGCCTCGATAATAAAGTATGCATTAAAGATAAACGCA |
| GAAGATAATTTTGCATTAGCAGCTTAATTTAGCGCTGCTCATCCTTCCTC |
| AATTGCCCACGGTTGAGAGTAAGGGTGTCATTTAAAAGTGGGGAACCGAG |
| CCTAGCAAAGCTTTGAGCTAGGAACGGAATTTATGAAGCTTACCAAAGAG |
| GAAGTTTGTCTGTGGACGTTCTCTGAGGGAATTTTAAAACACAAGACTAC |
| ACTCGTAGAAAGTCTTACTGGTCTGCTTTCGGACACGGGTTCAACTCCCG |
| CCACTCCA |

TABLE 18

| tmDNA Sequence for *Clostridium stercorarium* |
|---|
| (SEQ ID NO: 26) |
| GGGGGCGGAAAGGATTCGACGGGGTTATTGAAGCAAGAGTAGCGGGTAGA |
| GGATTCTCGTTGGCCTCTTTAAAAAACGAGAGCTAAAAATAAACGCAAAC |
| AACGATAACTACGCTTTAGCTGCTGCGTAAGTAACACGCAGCCCGTCGGC |
| CCCGGGGTTCCTGCGCCTCGGGATACCGGCGTCATCAAGGCAGGGAACCA |
| GCCGGATCAGGCTTCAGGTCCGGTGGGATTTAATGAAGCTACCGACTTAT |
| AAAGCCTGTCTCTGGGCCTTATAAGAAGGGAATGTCAAAACAGAGACTGC |
| ACCCGGAGAAGCTCTTGTGGATATGGTTCCGGACACGAGTTCGATTCCCG |
| CCGCCTCCACCA |

TABLE 19

| tmDNA Sequence for *Enterococcus faecium* (sp.) |
|---|
| (SEQ ID NO: 27) |
| GGGGCTGATTATGGATTCGACAGGATNGTTGAGCTTGAATTGCGTTTCGT |
| AGGTTACGGCTACGTTAAAACGTTACAGTTAAATATAACTGCTAAAAACG |
| AAAACAATTCTTTCGCTTTAGCTGCCTAAAAACCAGCTAGCGAAGATCCT |
| CCCGGCATCGCCCATGTGCTCGGGTCAGGGTCCTAATCGAAGTGGGATAC |
| GCTAAATTTTTCCGTCTGTAAAATTTAGAGGAGCTTACCAGACTAGCAAT |
| ACAAGAATGCCTGTCACTCGGCACGCTGTAAAGCGAACCTTTAAATGAGT |
| GTCTATGAACGTAGAGATTTAAGTGGGAATATGTTTTGGACGCGGGTTCA |
| ACTCCCGCCAGCTCCACCA |

TABLE 20

| tmDNA Sequence for *Heliobacillus mobilis* (photosyn/gram +) |
|---|
| (SEQ ID NO: 28) |
| GGGGCTGATTCTGGATTCGACGGGGAACGTGTTTGCTTGGGATGCGAGCC |
| GGGTTGCCGCCAGGACCGTAAAAAGGGCGGAAGGCTTTAATTGCCGAAGA |
| TAACTACGCTTTAGCTGCTTAATTGCAGTCTAACCTCTTCTCCTCTGTGC |

TABLE 20-continued

| tmDNA Sequence for *Heliobacillus mobilis* (photosyn/gram +) |
|---|
| TCTCGGTGAGGATGTAAGGGGTCATTTAAGAGAGCTGGCTTCGACCAATT |
| CTCGGAGGTCCAAGCGAGATTTATCGAGATAGCCTGACCAACGCTCTGTC |
| TGCCGTGCGGAAGGAAGGCGAAATCTAAAACGACAGACTACGCTCGTAGT |
| GTCCTTTGTGGGCATTTCTTCGGACGCGGGTTCAACTCCCGCCAGCTCCA |
| CCA |

TABLE 21

| tmDNA Sequence for *Heliospirillum gestii* |
|---|
| (SEQ ID NO: 29) |
| GGGGCTGATTCTGGATTCGACGGGGAACGTGTTTGCTTAGGACGCGAGCC |
| GGGTTGCCGCCAGGACCGTAAAAAGGGCGGAAGGCTTTAATTGCCGAAGA |
| TAACTACGCTTTAGCTGCTTAATTGCAGTCTAACCTCTTCTCCTCTGTGC |
| TCTCGGTGAGGATGTAAGGGGTCATTTAAGAGAGCTGGCTCGAACCAATT |
| CTCGGAGGTTCGGGTAAGACTTATCGAGATAGCCTGACCAACGCTCTGTC |
| TGCCGTGCGGAAGGATGGCGAAATCTAAAACGACAGAATACGCTCGTAGT |
| GTCCTTTGTGGGCATTTCTTCGGACGCGGGTTCAACTCCCGCCAGCTCCA |
| CCA |

TABLE 22

| tmDNA Sequence for *Lactobacillus acidophilus* |
|---|
| (SEQ ID NO: 30) |
| GGGGCTGATTCTGGATTCGACAGGCGTAGACCCGCATTGACTGCGGTTCG |
| TAGGTTACGTCTACGTAAAAACGTTACAGTTAAATATAACTGCAAATAAC |
| AAAAATTCTTACGCATTAGCTGCTTAATTTAGCGCATGCGTTGCTCTTTG |
| TCGGTTTACTCGTGGCTGACACTGAGTATCAACTTAGCGAGTTACGTTTA |
| ACTACCTCACCTGAATAGTTGAAAAGAGTCTTAGCAGGTTAGCTAGTCCA |
| TACTAGCCCTGTTATATGGCGTTTTGGACTAGTGAAGTTCAAGTAATATA |
| ACTATGATCGTAGAGGTCAGTGACGAGATGCGTTTGGACAGCGGGTTCAA |
| CTCCCGCCAGCTCCACCA |

TABLE 23

| tmDNA Sequence for *Staphylococcus epidermidis* |
|---|
| (SEQ ID NO: 31) |
| GGGGCTGATTCTGCATTCGACAGGGGTCCCCGAGCTTATTAAGCGTGTGG |
| AGGGTTGGCTCCGTCATCAACACATTTCGGTTAAATATAACTGACAAATC |
| AAACAATAATTTCGCAGTAGCTGCGTAATAGCCACTGCATCGCCTAACAG |
| CATCTCCTACGTGCTGTTAACGCGATTCAACCCTAGTAGGATATGCTAAA |
| CACTGCCGCTTGAAGTCTGTTTAGATGAAATATAATCAAGCTAGTATCAT |
| GTTGGTTGTTTATTGCTTAGCATGATGCGAAAATTATCAATAAACTACAC |

TABLE 23-continued

**tmDNA Sequence for *Staphylococcus epidermidis***

ACGTAGAAAGATTTGTATCAGGACCTCTGGACGCGGGTTCAACTCCCGCC

AGCTCCACCA

TABLE 24

**tmDNA Sequence for *Streptococcus faecium***

(SEQ ID NO: 32)
GGGGCTGATTCTGGATTCGACAGGCACAGTTTGAGCTTGAATTGCGTTTC

GTAGGTTACGTCTACGTTAAAACGTTACAGTTAAATATAACTGCTAAAAA

CGAAAACAACTCTTACGCTTTAGCTGCCTAAAAACAGTTAGCGTAGATCC

TCTCGGCATCGCCCATGTGCTCGAGTAAGGGTCTCAAATTTAGTGGGATA

CGTGACAACTTTCCGTCTGTAAGTTGTTAAAGAGATCATCAGACTAGCGA

TACAGAATGCCTGTCACTCGGCAAGCTGTAAAGCGAAACCACAAATGAGT

TGACTATGAACGTAGATTTTTAAGTGGCGATGTGTTTGGACGCGGGTTCA

ACTCCCGCCGTTCCACCA

TABLE 25

**tmDNA Sequence for *Thermoanaerobacterium saccharolyticum* (Bacillus/clostridium)**

(SEQ ID NO: 33)
GGGGTAGTAGAGGTAAAAGTAGCGAGCCGAGGTTCCATCTGCTCGTAAAA

CGGTGGACTTAAATATAAACGCAAACGATAATTTAGCTTACGCTGCTTAA

TTACAAGCAGCCGTTCAACCTTTGATTCCCACATCAAAGGATTGGGCGTC

GATTTAGTGGGGAACTGATTTATCAAAGCTTTGAGATAAATCGGATTTTA

TGAAGCTACCAAAGCAGTTATCCTGTCACTGGGAGAACTGCAGAGGGAAT

GTCAAAACAGTGACTGCGCTCGGAGAAGCTTTTACTGTGACACCTTCGGA

CCGGGGTTCAACTCCCGCCAGCTCCACCA

TABLE 26

**tmDNA Sequence for *Mycoplasma fermentans***

(SEQ ID NO: 34)
GGGGCTGATTCTGGATTCGACATGCATTGGGTGATACTAATATCAGTAGT

TTGGCAGACTATAATGCATCTAGGCTTTATAATCGCAGAAGATAAAAAG

CAGAAGAAGTTAATATTTCTTCACTTATGATTGCACAAAAAATGCAATCA

CAATCAAACCTTGCTTTCGCTTAGTTAAAAGTGACAAGTGGTTTTAAAGT

TGACATTTTCCTATATATTTTAAAATCGGCTTTTAAGGAGAACAGGAGTC

TGAAAGGGTTCCAAAAATCTATATTGTTTGCATTTCGGTAGTATAGATTA

ATTAGAAATGATAAACTGTAAAAGTATTGGTATTGACTTGGTGTGTGGA

CTCGGGTTCAACTCCCGCCAGCTCCACCA

TABLE 27

**tmDNA Sequence for *Mycoplasma hyorhinis***

(SEQ ID NO: 35)
GGGGCTGATTCTGGATTCGACATACATAAAAGGATATAAATTGCAGTGGT

CTTGTAAACCATAAGACAATTTCTTTACTAAGCGGAAAAGAAAACAAAAA

AGAAGATTATTCATTATTAATGAATGCTTCAACTCAATCAAATCTAGCTT

TTGCATTTTAAAAAACTAGTAGACCAATTTGCTTCTCACGAATTGTAATC

TTTATATTAGAGAATAGTTAAAAATCTGATCACTTTTTAATGAATTTATA

GATCACAGGCTTTTTTAATCTTTTTGTTATTTTAGATAAAGAGTCTTCTT

AAAAATAACTAAACTGTAGGAATTTATATTTAATTATGCGTGGACCCGGG

TTCAACTCCCGCCAGCTCCACCA

TABLE 28

**tmDNA Sequence for *Mycoplasma pirum***

(SEQ ID NO: 36)
GGGGAGTCATGGTTTTGACATGAATGATGGACCCATAGAGGCAGTGGGGT

ATGCCCCTTATAGCTCAAGGTTTAAATTAACCGACAAAACTGACGAAAAC

GTTGCCGTTGATCAAATTTATTAATCAACCAACAAGCTCAATTTAACTA

CGCATTTGCATAGTATAAAAAAATAAATTGTGCTACTCATTGTAATTAGG

TTACTAAATTACTTTGTTTTATATAGTCCTGTAACTAGTTCTAGTGATGT

CTATAAACTAGAATGAGATTTATAGACTTATTTGTTGGCGGTTGTGCCAT

AGCCTAAATCAACAAAGACAATTTATTTATGGTACTAAACTGTAGATTCT

ATGATGAAATTATTTGTGGAAACGGGTTCGATTCCCGCCATCTCCACCA

TABLE 29

**tmDNA Sequence for *Mycoplasma salivarium***

(SEQ ID NO: 37)
GGGGCTGATTCTGGATTCGACAGGCATTCGATTCATTATGTTGCAGTGGT

TTGCAAACCATAAGGCACTAGGCTTTTTTAAACGCAAAAGACCAAAAAAC

AGAAGATCAAGCAGTTGATCTAGCATTTATGAATAATTCACAAATGCAAT

CAAATCTAGTTTTCGCTTAGTAAAATTAGTCAATTTATTATGGTGCTCAA

CATAATAAATGGTAGTATGAGCTTAATATCATATGATTTTAGTTAATATG

ATAGGATTTGTAACTAAACTATGTTATAGAAATTTGTAAATTATATATAT

GACATAGGAAATTTAATTTACTAAACTGTAGATGCATAATGTTGAAGATG

TGTGGACCGGGGTTCAACTCCCGCCAGCTCCACCA

TABLE 30

**tmDNA Sequence for *Herpetosiphon aurantiacus***

(SEQ ID NO: 38)
GGGGGCGGAAAGGATTCGACGGGGAGGGCCAATCGTAAGTGGCAAGCCGA

GACGCTGAGCCTCGTTAAATCGGCAACGCCATTAACTGGCAAAAACACTT

TCCGCGCTCCTGTAGCGCTTGCTGCCTAATTAAGGCAACACGTCTCTACT

TABLE 30-continued tmDNA Sequence for *Herpetosiphon aurantiacus*

AGCCTCAGCCCGATGGGCTTGTAGCGGCGACACTTAGTCGGGTCGCTCCC

CTAGTTATGTCTGTGGGCTAGGGGCTAAGATTAACAGGCTGGTCGTGGCC

CGCTTTGTCTATCGGGTGGTGCACCGATAAGATTTAATCAATAGACTACG

CTTGTAGATGCTTGCGGTTTAACTTTTTGGACGCGGGTTCGATTCCCGCC

GCCTCACCACCA

TABLE 31 tmDNA Sequence for *Thermomicrobium roseum*
(352 nts, temp. 70 degrees, green non sulfur)

(SEQ ID NO: 39)
GGGGCTGATTCTGGATTCGACAGGGCCGTAGGTGCGAGGATTGCAGGTCG

AGGTCGCCCACGAACTCGTAAAAAGGGGCAGCCAAGTAACTGGCGAGCGC

GAACTCGCTCTGGCTGCGTAATTCACGCAGCCACGTCTGCCCGGACCCTT

CCCTGGTGGGTTCGGAGCGGGCGCCGCAAGACCGGGGTGCCCCTGGCCCA

AGCGCCGGTGCGGGCCAGGTCAAGCGTGATCCGGCTCGGCTGACCGGGAT

CCTGTCGGTGGGAGCCTGGCAGCGACAGTAGAACACCGACTAAGCCTGTA

GCATATCCTCGGCTGAACGCTCTGGACGCGGGTTCAACTCCCGCCAGCTC

CACCA

TABLE 32 tmDNA Sequence for *Chlorobium limicola*

(SEQ ID NO: 40)
GGGGCTGATTCTGGATTCGACAGGATACGTGTGAGATGTCGTTGCACTCC

GAGTTTCAGCATGGACGGACTCGTTAAACAAGTCTATGTACCATTAGATG

CAGACGATTATTCGTATGCAATGGCTGCCTGATTAGCACAAGTTAACTCA

GACGCCATCGTCCTGCGGTGAATGCGCTTACTCTGAAGCCGCCGGATGGC

ATAACCCGCGCTTGAGCCTACGGGTTCGCGCAAGTAAGCTCCGTACATTC

ATGCCCGAGGGGCTGTGCGGGTAATTTCTCGGGATAAGGGGACGAACGCT

GCTGGCGGTGTAATCGGCCCACGAAAACCCAATCACCAGAGATGAGTGTG

GTGACTGCATCGAGCAGTGTTTTGGACGCGGGTTCAACTCCCGCCAGCTC

CACCA

TABLE 33 tmDNA Sequence for *Pirellula staleyi*
(*planctomyces*)

(SEQ ID NO: 41)
GGGGCTGATTCTGGATTCGACCGGATAGCCTGAAGCGAATACGGCGTGCC

GTGGTTGATCAGATGGCCACGTAAAAGCTGATCACAAACTTAACTGCCG

AGAGCAATCTCGCACTTGCTGCCTAACTAAACGGTAGCTTCCGACTGAGG

GCTTTAGCCGGAGAGGCCCAAAAGTTGGTCACCAAATCCGGACCGCCTCG

TGCCATGATCGAAACGCACGAGGTCAAAAAAGTTTCGATCTAGTGCAGGG

TABLE 33-continued tmDNA Sequence for *Pirellula staleyi*
(*planctomyces*)

TGTAGCCAGCAGCTAGGCGACAAACTGTGCAAAAATCAAATTTTCTGCTA

CGCACGTAGATGTGTTCGTGAAAATGTCTCGGGACGGGGGTTCAACTCCC

GCCACTCCACCA

TABLE 34 tmDNA Sequence for *Planctomyces limnophilus*

(SEQ ID NO: 42)
GGGGCTGATTCTGGATTCGACAACCTCTCAAGAGGAGCGTGGCCACTATG

GGACTCGATTATGTTGAATTCGTCATGGATCTTGAAGAGACCTTCGACAT

CAAACTGGATGACAAACATTTTTCAGCAGTCAAAACACCACGCGATTTGG

CAATCATTATTCGGGATCAATTAGCTGCTGAAGGCAGAATCTGGGATGAA

TCGAATGCTTTTCGCAAAATCTCGAATTTGAATTGGACGATGTTGCCCGA

GTTCCGGATGTGGACTCAAATCAAAAGCTCTCTACCAGTTTCTTTTCACC

GACTGCGTCCCAGCACCCGTCTCGTTCAACTCCCGCCANTCCACCA

TABLE 35 tmDNA Sequence for *Planctomyces maris*

(SEQ ID NO: 43)
GGGGCTGATTCTGGATTCGACTGGTTCACCGTATGTTAAGGTGGCGGTGC

CGTGGTTGATCAGTTGGCCACGTAAAAAGCTGATCACAATCTAATTGCAA

ACAAGCAATTTTCAATGGCTGCTTAATAAAAGCAACCCCGGCTTAGGAAT

CTCTGTCTGAGGAGTCCGACAGCTGGTCACAAAATCAGACTGGTATCAGA

TCAATGTCCGCTCCGTCTGATACGAGATTCGTGGTGGACTGGTTTCCAAC

AGGCTCTGTTTATCGTGCCCGAAGAAACGAGACTCAAACGATAAAATATG

CACCGTAGAGGCTTTAGCTGAGGGTTCACAGGACGCGGGTTCAACTCCCG

CCAGCTCCACCA

TABLE 36 tmDNA Sequence for *Alcaligenes eutrophus*

(SEQ ID NO: 44)
GGGGTTGATTCTGGATTCGACGTGGGTTACAAAGCAGTGGAGGGCATACC

GAGGACCCGTCACCTCGTTAATCAATGGGAATGCAATAACTGCTAACGAC

GAACGTTACGCACTGGCCGCTTAATTGCGGCCGTCCTCGCACTGGCTCGC

TGACGGGCTAGGGTCGCAAGACCACGCGAGGTCATTTACGTCAGATAAGC

TCCGGAAGGGTCACGAAGCCGGGGACGAAAACCTAGTGACTCGCCGTCGT

AGAGCGTGTTCGTCCGCGATGCGCCGGTTAAATCAAATGACAGAACTAAG

TATGTAGAACTCTCTGTGGAGGGCTTACGGACGCGGGTTCAACTCCCGCC

AGCTCCACCA

TABLE 37 tmDNA Sequence for *Alcaligenes faecalis* (beta proteobacteria)

(SEQ ID NO: 45)
GGGGGCGGAAAGGATTCGACGGGGGTCAAGAAGCAGCACAGGGCGTGTCG

AGCACCAGTACGCTCGTAAATCCACTGGAAAACTATAAACGCCAACGACG

AGCGTTTCGCTCTAGCCGCTTAAGGCTGGGCCACTGCACTAATTTGTCTT

TGGGTTAGGTAGGGCAACCTACAGCAGTGTTATTTACAAAGAATCGAATC

GGTCTGCGCCACGAAGTCCGGTTCTAAAACTTAGTGGATCGCCAAGGAAA

GGCCTGTCAATTGGCATAGTCCAAGGTTAAAACTTAAAATTAATTGACTA

CACATGTAGAACTGTCTGTGGACGGCTTGCGGACGGGGGTTCGATTCCCG

CCGCCTCCACCA

TABLE 38 tmDNA Sequence for *Chromobacterium violaceum* (beta-purple)

(SEQ ID NO: 46)
GGGGCTGATTCTGGATTCGACGGGGGTTGCGAAGCAGATGAGGGCATACC

GGGATTTCAGTCACCCCGTAAAACGCTGAATTTATATAGTCGCAAACGAC

GAAACTTACGCTCTGGCAGCCTAACGGCCGGCCAGACACTACAACGGTTC

GCAGATGGGCCGGGGCGTCAAAACCCTGTAGTGTCACTCTACATCTGCT

AGTGCTGTTCCGGGTTACTTGGTTCAGTGCGAAATAATAGGTAACTCGCC

AAAGTCCAGCCTGTCCGTCGGCGTGGCAGAGGTTAAATCCAAATGACACG

ACTAAGTATGTAGAACTCACTGTAGAGGACTTTCGGACGCGGGTTCAACT

CCCGCCAGCTCCACCA

TABLE 39 tmDNA Sequence for *Hydrogenophaga palleroni* (beta-purple)

(SEQ ID NO: 47)
GGGGCTGATTCTGGATTCGACGTGGGTTCGGACGCGCAGCAGGGCATGTC

GAGGTTCTGTCACCTCGTAAATCAGCAGAAAAAACCAACTGCAAACGAC

GAACGTTTCGCACTCGCCGCTTAAACACCGGTGAGCCTTGCAACAGCAGG

CCGATGGGCTGGGCAAGGGGGTCGCAAGACCTCCCGGCTGCAAGGTAATT

TACATCGGCTGGTTCTGCGTCGGGCACCTTGGCGCAGGATGAGATTCAAG

GATGCTGGCTTCCCGTTTAGCGTGCCACTGCGCGACTCGGGCGGCGAGAC

CCAAATCAGACGGCTACACATGTAGAACTGCTCGAAAAAGGCTTGCGGAC

GGGGGTTCAACTCCCGCCAGCTCCACCA

TABLE 40 tmDNA Sequence for *Methylobacillus glycogenes* (beta-purple)

(SEQ ID NO: 48)
GGGGGCGGAAAGGATTCGACGGGGGTTGCAAAGCAGCGCAGGGCATACCG

AGGCCTAGTCACCTCGTAAATAAACTAGAACAAGTATAGTCGCAAACGAC

TABLE 40-continued tmDNA Sequence for *Methylobacillus glycogenes* (beta-purple)

GAAACTTACGCTCTAGCCGCTTAATCCCGGCTGGACGCTGCACCGAAGGG

CCTCTCGGTCGGGTGGGGTAACCCACAGCAGCGTCATTAAGAGAGGATCG

TGCGATATTGGGTTACTTAATATCGTATTAAATCCAAGGTAACTCGCCTG

CTGTTTGCTTGCTCGTTGGTGAGCATCAGGTTAAATCAAACAACACAGCT

AAGTATGTAGAACTGTCTGTGGAGGGCTTGCGGACGGGGGTTCGATTCCC

GCCGCCTCACCACCA

TABLE 41 tmDNA Sequence for *Nitrosomonas cryotolerans* (beta-purple)

(SEQ ID NO: 49)
GGGGCTGATTCTGGATTCGACGTGGGTTGCAAAGCAGCGCAGGGCATACC

GAGGACCAGAATACCTCGTAAATACATCTGGAAAAAAATAGTCGCAAACG

ACGAAAACTACGCTTTAGCCGCTTAATACGGCTAGCCTCTGCACCGATGG

GCCTTAACGTCGGGTCTGGCAACAGACAGCAGAGTCATTAGCAAGGATCG

CGTTCTGTAGGGTCACTTTACAGAACGTTAAACAATAGGTGACTCGCCTG

CCATCAGCCCGCCAGCTGGCGGTTGTCAGGTTAAATTAAAGAGCATGGCT

AAGTATGTAGAACTGTCTGTAGAGGACTTGCGGACGCGGGTTCAACTCCC

GCCAGTCCACCA

TABLE 42 tmDNA Sequence for *Pseudomonas testosteroni*

(SEQ ID NO: 50)
GGGGCTGATTCTGGATTCGACGTGGGTTCGGGACCGGTGCGGTGCATGTC

GAGCTTGAGTGACGCTCGTAAATCTCCATTCAAAAAACTAACTGCAAACG

ACGAACGTTTCGCACTCGCCGCTTAATCCGGTGAGCCTTGCAACAGCACG

CTAGTGGGCTGGGCAAGGGGGTAGCAATACCTCCCGGCTGCAAGGGAATT

TTCATTAGCTGGCTGGATACCGGGCTTCTTGGTATTTGGCGAGATTTTAG

GAAGCTGGCTACCCAAGCAGCGTGTGCCTGCGGGGTTTGGGTGGCGAGAT

TTAAAACAGAGCACTAAACATGTAGATCTGTCCGGCGAAGGCTTACGGAC

GCGGGTTCAACTCCCGCCAGCTCCACCA

TABLE 43 tmDNA Sequence for *Ralstonia pickettii* (Burkholderia)

(SEQ ID NO: 51)
GGGGGCGGAAAGGATTCGACGGGGGTTGCGAAGCAGCGGAGGGCATACCG

AGGACCCGTCACCTCGTTAATCAATGGGAATGCAATAACTGCTAACGACG

AACGTTACGCACTGGCAGCCTAAGGGCCGCCGTCCTCGCACTGGCTCGCT

GACGGGCTAGGGTCGCAAGACCAGCGAGGTCATTTACGTCAGATAAGCTT

TABLE 43-continued tmDNA Sequence for *Ralstonia pickettii* (*Burkholderia*)

TAGGTGAGTCACGGGCCTAGAGACGAAAACTTAGTGAATCGCCGTCGTAG

AGCGTGTTCGTCCGCGATGCGGCGGTTAAATCAAATGACAGAACTAAGTA

TGTAGAACTCTCTGTGGAGGGCTTGCGGACGCGGGTTCGATTCCCGCCGC

CTCACCACCA

TABLE 44 tmDNA Sequence for *Variovax paradoxus* (*pseudomonas sp.*)

(SEQ ID NO: 52)
GGGGCTGATTCTGGATTCGACGTGGGTTCGGAGTCGCAGCGGGGCATGTC

GAGCTGAATGCGCTCGTAAAACAGATTCAAACAAACTAACTGCAAACGAC

GAACGTTTCGCACTCGCTGCTTAATTGCCAGTGAGCCTTGCAACAGTTGG

CCGATGGGCTGGGCAAGGGGGTCTGGAGCAATCCTGACCTCCCGGCTGCA

AGGATAACTACATGGGCTGGCTCCGATCCGGGTACCTTGGGTCGGGGCGA

GAAAATAGGGTACTGGCGTCCGGTTTAGCGTGTGACTGCGCGACTCCGA

AGCGAGACTCAAAACAGATCACTAAACATGTAGAACTGCGCGATGAAGGC

TTGCGGACGGGGGTTCAACTCCCGCCAGCTCCACCA

TABLE 45 tmDNA Sequence for *Bdellovibrio bacteriovorus* (delta proteobacterie)

(SEQ ID NO: 53)
GGGGGCGGAAAGGATTCGACGGGGGTGCTGAAGCATAAGGAGCATACCGG

GGCGGATGAGGACCTCGTTAAAAACGTCCACTTTGTAATTGGCAACGATT

ACGCACTTGCAGCTTAATTAAGCAGCACGATCAACCTTGTGGTGGTTCCG

CACTTGGATTGATCGTCATTTAGGGACCTCGGCGTGTTGGGTTTTCTCCA

GCAGACATGCTTAAATTTACTGGGGGAGAGGTCTTAGGGATTTTGTCTGT

GGAAGCCCGAGGACCAATCTAAAACACTGACTAAGTATGTAGCGCCTTAT

CGTGGATCATTTGCGGACGGGGGTTCGATTCCCGCCGCCTCCACCA

TABLE 46 tmDNA Sequence for *Myxococcus xanthus* (delta proteobacterie)

(SEQ ID NO: 54)
GGGGGCGGAAAGGATTCGACGGGGGCATTGAAGTTCGAGACGCGTGCCGA

GCTTGTCAGGTAGCTCGTAAATTCAACCCGGCAAAGACACAAAAGCCAAC

GACAACGTTGAGCTCGCGCTGGCTGCCTAAAAACAGCCCATAGTGCGCGG

TCCCCCCGCCCTCGGCCTGTGGGGTTGGGACAGACCGTCATAATGCAGGC

TGGCTGCCGAGGGTGCCTGGACCCGAGGTGGCGAGATCTTCCCAGGACCG

GCTCTGAGTATCCCGTCCGTGGGAGCCTCAGGGACGTAGCAAATCGCGGA

TABLE 46-continued tmDNA Sequence for *Myxococcus xanthus* (delta proteobacterie)

CTACGCACGTAGGGTCGAAGAGCGGACGGCTTTCGGACGCGGGTTCGATT

CCCGCCGCCTCCACCA

TABLE 47 tmDNA Sequence for *Sulfurospirillum Deleyianum*

(SEQ ID NO: 55)
GGGGCTGATTCTGGATTCGACAGGAGTAGTTTTAGCTTATGGCTGCATGT

CGGGAGTGAGGGTCTTCCGTTACACAACCTTCAAACAATAACTGCTAACA

ACAGTAACTATCGTCCTGCTTACGCGCTAGCTGCGTAAGTTTAACAAATA

ATGGACTGCTCTCCCCTTTGATGCTATCTTAGGAGGTCTTGGAGAGTATC

ATAGATTTGATAGCTATATTACATGAACGCCTTTACATGTAATGAAGTTA

AAGGCTCGTTTTGCGTAGTTTTCTGATTGTTGTACGAAGCAAAATTAAAC

ACTATCAACAATATCTAAGCATGTAGACGTCATAGGTGGCTATTTTTGGA

CTGCGGGTTCAACTCCCGCCAGCTCCACCA

TABLE 48 tmDNA Sequence for *Chromatium vinosum*

(SEQ ID NO: 56)
GGGGCTGATTCTGGATTCGACGTGGGTCGCGAAACCTAAGGTGCATGCCG

AGGTGCGGTTGACCTCGTAAAACCCTCCGCAAACTTATAGTTGCCAACGA

CGACAACTACGCTCTCGCTGCTTAATCCCAGCGGGCCTCTGACCGTCACT

TGCCTGTGGGCGGCGGATTCCAGGGGTAACCTCACACAGGATCGTGGTGA

CGGGAGTCCGGACCTGATCCACTAAAACCTAACGGAATCGCCGACTGATC

GCCCTGCCCTTCGGGCGGCAGAAGGCTAAAAACAATAGAGTGGGCTAAGC

ATGTAGGACCGAGGGCAGAGGGCTTGCGGACGCGGGTTCAACTCCCGCCA

GCTCCACCA

TABLE 49 tmDNA Sequence for *Pseudomonas fluorescens* (gamma proteobacteria)

(SEQ ID NO: 57)
GGGGCTGATTCTGGATTCGACGCCGGTTGCGAACCTTTAGGTGCATGCCG

AGTTGGTAACAGAACTCGTAAATCCACTGTTGCAACTTTCTATAGTTGCC

AATGACGAAACCTACGGGAATACGCTCTCGCTGCGTAAGCAGCCTTAGC

CCTTCCCTCCTGGTACCTTCGGGTCCAGCAATCATCAGGGGATGTCTGTA

AACCCAAAGTGATTGTCATATAGAACAGAATCGCCGTGCAGTACGTTGTG

GACGAAGCGGCTAAAACTTACACAACTCGCCCAAAGCACCCTGCCCGTCG

GGTCGCTGAGGGTTAACTTAATAGACACGGCTACGCATGTAGTACCGACA

GCAGAGTACTGGCGGACGCGGGTTCAACTCCCGCCAGCTCCACCA

TABLE 50 tmDNA Sequence for *Borrelia afzeli*

(SEQ ID NO: 58)
GGGGCTGATTCTGGATTCGACTGAAAATGCTAATATTGTAAGTTGCAAGC

AGAGGGAATCTCTTAAAACTTCTAAAATAAATGCAAAAAATAATAACTTT

ACAAGTTCAAACCTTGTAATGGCTGCTTAAGTTAGCAGAGAGTTTTGTTG

AATTTGGCTTTGAGATTCACTTATACTCTTTTAGACATCGAAGCTTGCTT

AAAAATGTTTTCAAGTTGATTTTTAGGGACTTTTATACTTGAGAGCAATT

TGGCGGTTTGCTAGTATTTCCAAACCATATTGCTTAGTAAAATACTAGAT

AAGCTTGTAGAAGCTTATAGTATTGTTTTTAGGACGCGGGTTCAACTCCC

GCCAGTCCACCA

TABLE 51 tmDNA Sequence for *Borrelia crociduarae*

(SEQ ID NO: 59)
GGGGCTGATTCTGGATTCGACTAAGAACTTTAGTAGCATAAATGGCAAGC

AGAGTGAATCTCTTAAAACTTCTTTAATAAATGCAAAAAATAATAACTTT

ACAAGTTCAGATCTTGTAATGGCTGCTTAATTTAGCAGAGAGTTTTGTTG

GATTTTGCTTTGAGGTTCAACTTATACTCTTTAAGACATCAAAGTATGCC

TAAAAATGTTTCAAGTTGATTTTTAGGACCTTTAAACTTGAGAGTAATT

TGGTGGTTTGCTTGTTTTCCAAGCCTTATTGCTTTTTCTAAAAATTAGCT

AAGCTTGTAGATATTTATGATATTATTTTTAGGACGCGGGTTCAACTCCC

GCCAGTTCCACCA

TABLE 52 tmDNA Sequence for *Borrelia hermsii*

(SEQ ID NO: 60)
GGGGCTGATTCTGGATTCGACTAAAAACTTTAGTAGCATAAATTGCAAGC

AGAGGGAATCTCTTAAAACTTCTTTAATAAATGCAAGAAATAATAACTTT

ACAAGTTCAAATCTTGTAATGGCTGCTTAAATTAGCAGAGAGTTCTGCTG

GATTTTGCTTTGAGGTTCAGCTTATACTCTTTTAAGACATCAAAGCTTGC

TTAAAAATATTTCAAGTTGATTTTTAGGGACTTTTAAATTTGAGAGTAAT

TTGGCGGTTTGCTAGTTTTTCCAAACCTTATTACTTAAAGAAAACACTAG

CTAAGCTTGTAGATATTTATGATATTATTTTTAGGACGCGGGTTCAACTC

CCGCCAGCTCCACCA

TABLE 53 tmDNA Sequence for *Borrelia garinii*

(SEQ ID NO: 61)
GGGGCTGATTCTGGATTCGACTGAAAATGCGAATATTGTAAGTTGCAGGC

AGAGGGAATCTCTTAAAACTTCTAAAATAAATGCAAAAAATAATAACTTT

ACAAGCTCAAACCTTGTAATGGCTGCTTAAGTTAGCAGGGAGTTTCGTTG

TABLE 53-continued tmDNA Sequence for *Borrelia garinii*

AATTTGGCTTTGAGGTTCACTTATACTCTTTTCGATATCGAAGCTTGCTT

AAAAATGTTTTCAAGTTAATTTTTAGGGACTTTTGTACTTGAGAGCAATT

TGGCGGTTTGCTAGTATTTCCAAACCATATTGCTTAAGTAAAATGCTAGA

TAAGCTTGTAGAAGCTTATAATATTGTTTTTAGGACGCGGGTTCAACTCC

CGCCAGTCCACCA

TABLE 54 tmDNA Sequence for *Thermodesulfobacterium commune* (70 degrees)

(SEQ ID NO: 62)
GGGGGCGGAAAGGATTCGACGGGGATAGGTAGGATTAAACAGCAGGCCGT

GGTCGCACCCAACCACGTTAAATAGGGTGCAAAAACACAACTGCCAACGA

ATACGCCTACGCTTTGGCAGCCTAAGCGTGCTGCCACGCACCTTTAGACC

TTGCCTGTGGGTCTAAAGGTGTGTGACCTAACAGGCTTTGGGAGGCTTAA

TCGGTGGGGTTAAGCCTCCCGAGATTACATCCCACCTGGTAGGGTTGCTT

GGTGCCTGTGACAAGCACCCTACGAGATTTTCCCACAGGCTAAGCCTGTA

GCGGTTTAATCTGAACTATCTCCGGACGCGGGTTCGATTCCCGCCGCCTC

CCCACCA

TABLE 55 tmDNA Sequence for *Thermotoga neapolitana* (Thermotogales)

(SEQ ID NO: 63)
GGGGGCGGAAAGGATTCGACGGGGATGGAGTCCCCTGGGAAGCGAGCCGA

GGTCCCCACCTCCTCGTAAAAAAGGTGGGAACACGAATAAGTGCCAACGA

ACCTGTTGCTGTTGCCGCCTAATAGATAGGCGGCCGTCCTCTCCGGAGTT

GGCTGGGCTCCGGAAGAGGGCGTGAGGGATCCAGCCTACCGATCTGGGCT

CCGCCTTCCGGCCCGGATCGGAAGGTTCAGGAAGGCGTGTGGGAAGCGAC

ACCCTGCCCGTGGGGGTCCTTCCCGAGACACGAAACACGGGCTGCGCTC

GGAGAAGCCCAGGGGCCTCCATCTTCNGACGCGGGTTCGATTCCCGCCAC

CTCCACCA

TABLE 56 tmDNA Sequence for *Deinococcus proteolyticus*

(SEQ ID NO: 64)
GGGGGCGGAAAGGATTCGACGGGGGAACGGAAAGCGCTGCTGCGTGCCGA

GGAGCCGTTGGCCTCGTAAACAAACGGCAAAGCCATTAACTGGCGAAAAT

AACTACGCTCTCGCTGCTTAAGTGAGACAGTGACCACGTAGCCCCGCCTT

TGGCGACGTGTGAACTGAGACAAAAGAAGGCTAGCTTAGGTGAGGTTCCA

TAGCCAAAAGTGAAACCAAATGGAAATAAGGCGGACGGCAGCCTGTTTGC

TABLE 56-continued tmDNA Sequence for *Deinococcus proteolyticus*

TGGCAGCCCAGGCCCGACAATTTAAGAGCAGACTACGCACGTAGATGCAC

GCTGGATGGACCTTTGGACGCGGGTTCGATTCCCGCCAGCTCCACCA

TABLE 57 tmDNA Sequence for *Prosthecobacter fusiformis* (*verrucomicrobia*)

(SEQ ID NO: 65)
GGGGCTGATTCTGGATTCGACGGGGAGTACAAGGATCAAAAGCTGCAAGC

CGAGGTGCCGTTACCTCGTAAAACAACGGCAAAAAAGAAGTGCCAACACA

AATTTAGCATTAGCTGCTTAATTTAGCAGCTACGCTCTTCTAACCCGGGC

TGGCAGGGTTAGAAGGGTGTCATAATGAGCCAGCTGCCCCTTCCGACTCC

CCTAAGGAAGGGAAAGATGTAGGGGATAGGTGCTTACAGAATCCTGCGGG

AGGGAGTCTGTAAGTGCCGAAAAGTTAAAACTCCCGCTAAGCTTGTAGAG

GCTTTTGATTCTTGCTCTCTGGACGCGGGTTCAACTCCCGCCAGCTCCAC

CA

TABLE 58 tmDNA Sequence for *Verrucomicrobium spinosum* (*verrucomicrobium*)

(SEQ ID NO: 66)
GGGNNNNATTTGGAATTCGCCGAATGCTAGAAGTGGAGGCTGCATGCCGC

GGATGATTCGTTGGCCGCTTTACCAATTCGGATCAAACAACTAAATGCGG

ACTCTAACGAGCTTGCCCTCGCCGCTTAATTGACGGTGACGTTCCTCCAG

TGAAGTCTGTGAATTGGAGGAGCGACTACTTACAGGCTGGCCAAAAGAGC

GGGCGACCGGCCCCAAGGCGAGATCTACAGGCCGCTGGATGGACGGCATC

CTGGCAGTAGGAGGCTGGACATCGAGATCAAATNATTGCCTGAGCATGGA

GACGCTTTCATAAAGGNGTTCGGACAGGG

Example 4

Alignment of tmRNA Sequences

The newly discovered tmRNA sequences and several known tmRNA sequences were aligned to identify target sites for drug development. The alignments of the sequences are shown in FIGS. 3A-11B. The nucleotides in the tmRNA sequences of these figures exist in several motifs (Felden et al., 1999). These motifs include nucleotides considered to be in RNA helices (Watson-Crick base-pairs GC or AU, or GU Wobble base-pairs). Nucleotides that are in in single stranded RNA domains, hence not base-paired. Some nucleotides in the single stranded domains are universally conserved nucleotides. Other nucleotides are the exceptions to a quasi-sequence conservation in the sequences alignment. Several nucleotides exist in well established non-canonical structural motifs in RNA structures; for example AG-GA pairs, AA pairs, etc. Some nucleotides are universally conserved Wobble GU base-pairs.

All the gene sequences have been decomposed in several structural domains that have been indicated with names at the top of each block of sequences. These domains are respectively from the 5'-end to the 3'-end of the sequences: H1, H5, H2, PK1, H4, PK2, PK3, PK4, H5 and H6. The bars delineate all the structural domains. H means helices and PK means pseudoknot. A pseudoknot is made of the pairing of parts of an RNA-loop with an upstream sequence. Consequently, two helices are made (shown in Felden et al., 1999) for all the 4 pseudoknots PK1 to PK4 for each sequence. Moreover, the tRNA-like domain as well as the coding sequence, namely the two functional units of the molecule, have also been indicated for each sequence.

The sequences, especially as identified by the sequence alignment, represent targets for the development of drugs which may be broadly applicable to many kinds of bacteria, or may be broadly applicable only to a particular genera of phylum of bacteria, or may be specifically applicable to a single species of bacteria.

Common Structural Features for Drug Targeting:

For all the novel tmRNA sequences, as well as with the ones that are already known, there are systematically several structural domains that are always found. These domains can be used as targets for the development of drugs which may be genera specific or which may be eubacteria specific. These domains are either RNA helices which can be sometimes interrupted by bulges or pseudoknots. The RNA helices which are always present are H1, H2, H5 and H6. Helices H1 and H6 are found in all canonical transfer RNAs. Thus, H1 and H6 are not good targets for drug development because drugs that would target them will also interfere with the biology of the individual that has a given disease. Consequently, very good candidates for development of drugs for targeting as many bacteria as possible are helices H2 and H5. Moreover, helices H2 and H5 are critical for the folding of all these tmRNA since both of them connect the two ends of the molecule together. Disruption of either H2 or H5 with a specific drug would lead to inactive tmRNA molecules in vivo. Similarly, pseudoknots PK1, PK2 and PK3 are always found in the bacterial tmRNAs. The PK1 structural domain is strictly conserved in the tmRNAs and is located upstream of the coding sequence. Since these pseudoknots are not found in all canonial transfer RNAs, they can also be targeted with specific drugs. Disruption of either PK1 or PK2 or PK3 with a specific drug would lead to inactive tmRNA molecules in vivo.

Specific Structural Features in Each Phylum that could be Targeted by Drugs:

In addition to developing drugs which broadly target many bacteria, drugs are developed which are more genera specific. For trying to target specifically a given bacteria or a complete phylum, the coding sequence (shown in all the alignments) is a very good candidate. Indeed, this region of the RNA is very accessible for DNA antisense binding, which has been shown for *Escherichia coli*, and thus, is also available for interaction with other drugs. Moreover, this is a critical functional domain of the molecule in its quality-control mechanism in cells. In addition, this coding sequence would be the ideal target to use for designing specific PCR-based diagnostic assays for infection diseases.

Interestingly, some structural domains are present only in a given bacterial phyla and could be targeted for discovering a drug that will be specific of a phylum, but not of the others. For example:

(1) in the cyanobacteria, the fourth pseudoknot PK4 is made of two smaller pseudoknots called PK4a and PK4b;

(2) in the mycoplasma, helix H2 is made of only 4 base-pairs instead of 5 in the other species;

(3) for two sequences of chlorobium as well as *Bacteroides thetaiotaomicron* and ppm gingiv., there is an additional domain just downstream of the coding sequence that is unique to them;

(4) there is always a stem-loop in the coding sequence of the actinobacteria (Felden et al., 1999); and (5) all the beta proteobacteria possess a sequence insertion in pseudoknot PK2 (shown in the alignment).

The novel sequences described herein, when aligned, show that specific structural domains within tmRNA are strictly conserved, as for example pseudoknot PK1 is located upstream (at the 5'-side) of the coding sequence. As previously disclosed, this pseudoknot is a target for future antibacterial drugs. Moreover, recent data have shown that this PK1 pseudoknot, among all the four pseudoknots within tmRNA gene sequences (sometimes there's only 2 or 3 detectable pseudoknots, depending upon the sequences), is the only one that its correct folding is essential for the biological activity of tmRNA (Nameki et al., 1999; Nameki et al., 2000).

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Andersson, S. G. et al. (1998). *Nature* 396:133-140.
Ando, H. et al. (1996). *Genes & Genet. Syst.* 71:47-50.
Breithaupt, H. (1999). *Nature Biotechnol.* 17:1165-1169.
Felden, B. et al. (1996). *Biochimie* 78:979-983.
Felden, B. et al. (1997). *RNA* 3:89-103.
Felden, B. et al. (1998). *EMBO J.* 17:3188-3196.
Felden et al. (1999). *Biochim. Biophys. Acta* 1446:145-148.
Gray, M. W. and Spencer, D. F. (1996). In *Evolution of Microbial Life*, Cambridge University Press, pp. 109-126.
Hickerson, R. P. et al. (1998). *J. Mol. Biol.* 279:577-587.
Himeno, H. et al. (1997). *J. Mol. Biol.* 268:803-808.
Huang, C. et al. (2000). *EMBO J.* 19:1098-1107.
Julio, S. M et al. (2000). *J. Bacteriol.* 182:1558-1563.
Keiler, K. C. et al. (1996). *Science* 271:990-993.
Komine, Y. et al. (1994). *Proc. Natl. Acad. Sci. USA* 20:9223-9227.
Mateeva, O. et al. (1997). *Nucleic Acids Res.* 25:5010-5016.
Muto, A. et al. (1998). *Trends Biochem. Sci.* 1:25-29.
Nameki, N. et al. (1999). *J. Mol. Biol.* 286:733-744.
Nakemi, N. et al. (2000). *FEBS Lett.* 470:345-349.
*Remington's Pharmaceutical Sciences*, 18th Ed., Mack Publishing Co., Easton, Pa., 1990.
Tu, G. F. et al. (1995). *J. Biol. Chem.* 270:9322-9326.
Ushida, C. et al. (1994). *Nucleic Acids Res.* 16:3392-3396.
Williams, K. P. (1999). *Nucleic Acids Res.* 27:165-166.
Williams, K. P. and Bartel, D. P. (1996). *RNA* 2:1306-1310.
Wower, J. and Zwieb, C. (1999). *Nucleic Acids Res.* 27:167.
Yang, D. et al. (1985). *Proc. Natl. Acad. Sci. USA* 82:4443-4447.

What is claimed is:

1. An isolated nucleic acid sequence selected from the group consisting of a tmRNA sequence for *Mycoplasma pneumoniae*, a tmDNA sequence encoding said tmRNA sequence, and a full-length complement of said tmDNA sequence, wherein the tmRNA sequence for *Mycoplasma pneumonia* has the sequence set forth in SEQ ID NO:112.

2. A method for diagnosing a bacterial infection associated with *Mycoplasma pneumonia* comprising determining the presence of a bacterial nucleic acid sequence selected from the group consisting of a tmRNA sequence for *Mycoplasma pneumoniae* set forth in SEQ ID NO:112, a tmDNA sequence encoding said tmRNA sequence, and a full-length complement of said tmDNA sequence, wherein the tmRNA sequence for *Mycoplasma pneumonia* has the sequence set forth in SEQ ID NO:112.

3. The method of claim 2, wherein the determination is made by performing an amplification-based assay.

4. The isolated nucleic acid sequence of claim 1, wherein the nucleic acid sequence is the tmDNA sequence encoding the tmRNA sequence for *Mycoplasma pneumoniae*.

5. The method of claim 2, wherein the bacterial nucleic acid sequence is the tmDNA sequence encoding the tmRNA sequence for *Mycoplasma pneumoniae*.

6. The method of claim 3, wherein the bacterial nucleic acid sequence is the tmDNA sequence encoding the tmRNA sequence for *Mycoplasma pneumoniae*.

\* \* \* \* \*

SEQUENCE LISTING

```
<160> NUMBER OF SEQ ID NOS: 175

<210> SEQ ID NO 1
<211> LENGTH: 21
<212> TYPE: DNA
<213> ORGANISM: Artificial
<220> FEATURE:
<223> OTHER INFORMATION: PCR primer

<400> SEQUENCE: 1
ggggctgatt ctggattcga c                                               21

<210> SEQ ID NO 2
<211> LENGTH: 21
<212> TYPE: DNA
<213> ORGANISM: Artificial
<220> FEATURE:
<223> OTHER INFORMATION: PCR primer

<400> SEQUENCE: 2
tggagctggc gggagttgaa c                                               21

<210> SEQ ID NO 3
<211> LENGTH: 21
<212> TYPE: DNA
<213> ORGANISM: Artificial
<220> FEATURE:
<223> OTHER INFORMATION: PCR primer
```

```
<400> SEQUENCE: 3
gggggcggaa aggattcgac g                                              21

<210> SEQ ID NO 4
<211> LENGTH: 21
<212> TYPE: DNA
<213> ORGANISM: Artificial
<220> FEATURE:
<223> OTHER INFORMATION: PCR primer

<400> SEQUENCE: 4
tggaggcggc gggaatcgaa c                                              21

<210> SEQ ID NO 5
<211> LENGTH: 21
<212> TYPE: DNA
<213> ORGANISM: Artificial
<220> FEATURE:
<223> OTHER INFORMATION: PCR primer

<400> SEQUENCE: 5
ggggatgtca tggttttgac a                                              21

<210> SEQ ID NO 6
<211> LENGTH: 21
<212> TYPE: DNA
<213> ORGANISM: Artificial
<220> FEATURE:
<223> OTHER INFORMATION: PCR primer

<400> SEQUENCE: 6
tggagatggc gggaatcgaa c                                              21

<210> SEQ ID NO 7
<211> LENGTH: 21
<212> TYPE: DNA
<213> ORGANISM: Artificial
<220> FEATURE:
<223> OTHER INFORMATION: PCR primer

<400> SEQUENCE: 7
ggggatgaca ggctatcgac a                                              21

<210> SEQ ID NO 8
<211> LENGTH: 21
<212> TYPE: DNA
<213> ORGANISM: Artificial
<220> FEATURE:
<223> OTHER INFORMATION: PCR primer

<400> SEQUENCE: 8
tggagatggc gggacttgaa c                                              21

<210> SEQ ID NO 9
<211> LENGTH: 352
<212> TYPE: DNA
<213> ORGANISM: Acidobacterium capsulatum

<400> SEQUENCE: 9
gggggcggaa aggattcgac ggggttgact gcggcaaaga ggcatgccgg ggggtgggca    60
cccgtaatcg ctcgcaaaac aatacttgcc aacaacaatc tggcactcgc agcttaatta   120
aataagttgc cgtcctctga ggcttcgcct gtgggccgag gcaggacgtc atacagcagg   180
ctggttcctt cggctgggtc tgggccgcgg ggatgagatc cacggactag cattctgcgt   240
```

```
atcttgtcgc ttctaagcgc agagtgcgaa acctaaagga atgcgactga gcatggagtc    300
tcttttctga caccaatttc ggacgcgggt tcgattcccg ccgcctccac ca            352

<210> SEQ ID NO 10
<211> LENGTH: 353
<212> TYPE: DNA
<213> ORGANISM: Coprothermobacter proteolyticus

<400> SEQUENCE: 10 ggggcggaa aggattcgac ggggagtcgg agccttgagc tgcaggcagg gttggctgcc     60
acaccttaaa aagggtagca aggcaaaaat aaatgccgaa ccagaatttg cactagctgc   120
ttaatgtaag cagccgctct ccaaactgag gctgcataag tttggaagag cgtcaaccca   180
tgcagcggct cttaagcagt ggcaccagct gtttaagggt gaaaagagtg gtgctgggca   240
gtgcggttgg gcttcctggg ctgcactgtc gagacttcac aggagggcta agcctgtaga   300
cgcgaaaggt ggcggctcgt cggacgcggg ttcgattccc gccgcctcca cca          353

<210> SEQ ID NO 11
<211> LENGTH: 399
<212> TYPE: DNA
<213> ORGANISM: Bacteroides thetaiotaomicron

<400> SEQUENCE: 11
ggggctgatt ctggattcga cagcgggcag aaatggtagg taagcatgca gtgggtcggt    60
aatttccact taaatctcag ttatcaaaac tttatctggc gaaactaatt acgctcttgc   120
tgcttaatcg aatcacagta gattagctta atccaggcac taggtgccag gacgagacat   180
cactcggaag ctgttgctcc gaagcattcc ggttcagtgg tgcagtaaca tcggggatag   240
tcagaagcgg cctcgcgttt ttgatgaaac tttagaggat aaggcaggaa ttgatggctt   300
tggttctgct cctgcacgaa aatttaggca aagataagca tgtagaaagc ttatgatttc   360
ctcgtttgga cgagggttca actcccgcca gctccacca                           399

<210> SEQ ID NO 12
<211> LENGTH: 352
<212> TYPE: DNA
<213> ORGANISM: Dictyoglomus thermophilum

<400> SEQUENCE: 12
ggggctgatt ctggattcga cagggagtac aaggatcaaa agctgcaagc cgaggtgccg    60
ttacctcgta aacaacggc aaaaagaag tgccaacaca aatttagcat tagctgctta    120
atttagcagc tacgctcttc taacccgggc tggcagggtt agaagggtgt cataatgagc   180
cagctgcccc ttccgactcc cctaaggaag ggaaagatgt aggggatagg tgcttacaga   240
atcctgcggg agggagtctg taagtgccga aaagttaaaa ctcccgctaa gcttgtagag   300
gcttttgatt cttgctctct ggacgcgggt tcaactcccg ccagctccac ca            352

<210> SEQ ID NO 13
<211> LENGTH: 313
<212> TYPE: DNA
<213> ORGANISM: Artificial
<220> FEATURE:
<223> OTHER INFORMATION: sequence isolated from rumenal fluid
```

```
<400> SEQUENCE: 13
acgcccttgt ctcagacgag ggcactcgtt aaaaagtctg aaaagaataa ctgcagaacc        60
tgtagctatg gctgcttaat ttaagggcaa cccttggatc cgcctccatc ccgaaggggt       120
ggcatccgag tcgcaaatcg ggataggatg gatcttggca acgaggagta catccgaaat       180
ttgtcgctgc tggctgaagc atcgccgttc ctctttgggc gtggcaaggc aagattaaat       240
tcagaggata agcgtgtagt agcgagtgag taggtgtttt tggacgcggg ttcaagtccc       300
gccatctcca cca                                                          313

<210> SEQ ID NO 14
<211> LENGTH: 350
<212> TYPE: DNA
<213> ORGANISM: Artificial
<220> FEATURE:
<223> OTHER INFORMATION: sequence isolated from sludge

<400> SEQUENCE: 14
ggggatgtca tggttttgac agggaaccag gaggtgtgag atgcatgccg gagacgctgt        60
ccgctccgtt atcaagcagc aaacaaaact aattgcaaac aacaattact ccttagcagc       120
gtaagcagct aacgttcaac ctctccggac cgccgggagg ggatttgggc gtcgaaacag       180
cgcggacgct ccgatagga cgcccataat atccggctaa gaccatgggt ctggctctcg       240
cgggtctgat tgtcttccac cgcgcgggcc gcgatcaaag acaactaagc atgtaggttc       300
ttgcatggcc tgttctttgg acgcgggttc gattcccgcc atctccacca                  350

<210> SEQ ID NO 15
<211> LENGTH: 359
<212> TYPE: DNA
<213> ORGANISM: Fibrobacter succinogenes

<400> SEQUENCE: 15
ggggctgatt ctggattcga cagggttacc gaagtgttag ttgcaagtcg aggtctcaga        60
cgagggctac tcgttaaaaa gtctgaaaaa aaataagtgc tgacgaaaac tacgcactcg       120
ctgcctaatt aacggcaacg ccgggcctca ttccgctccc atcggggtgt acgtccggac       180
gcaatatggg atagggaagt gtcatgcctg ggggcatctc ccgagatttt ctaggctggt       240
caaactccgc gccgaccttc ttgggcgtgg ataagacgag atcttaaatt cgaagggaac       300
acttgtagga acgtacatgg acgtgatttt ggacaggggt tcaactcccg ccagctcca       359

<210> SEQ ID NO 16
<211> LENGTH: 350
<212> TYPE: DNA
<213> ORGANISM: Fusobacterium mortiferum

<400> SEQUENCE: 16
ggggctgatt ctggattcga cggggttatg aggttatagg tagcatgcca ggatgaccgc        60
tgtgagaggt caacacatcg tttagatgga aacagaaatt acgctttagc tgcttaatta       120
gtcagctcac ctctggtttc tctcttctgt aggagaatcc aaccgaggtg ttaccaatat       180
acagattacc tttagtgatt tctctaagct caaagggaca ttttagagaa tagcttcagt       240
tagccctgtc tgcgggagtg attgttgcga aataaaatag tagactaagc attgtagaag       300
cctatggcgc tggtagtttc ggacacgggt tcaactcccg ccagctccaa                  350
```

<210> SEQ ID NO 17
<211> LENGTH: 377
<212> TYPE: DNA
<213> ORGANISM: Corynebacterium xerosis

<400> SEQUENCE: 17

```
ggggctgatt ctggattcga cttcgtacat tgagccaggg gaagcgtgcc ggtgaaggct      60
ggagaccacc gcaagcgtcg cagcaaccaa ttaagcgccg agaactctca gcgcgactac     120
gccctcgctg cctaagcagc gaccgcgtgt ctgtcagacc gggtaggcct ctgatccgga     180
ccctggcatc gtttagtggg gctcgctcgc cgacttggtc gcaagggtcg gcggggacac     240
tcacttgcga ctgggcccgt catccggtca tgttcgactg aaccggaggg ccgagcagag     300
accacgcgcg aactgcgcac ggagaagccc tggcgaggtg acggaggacc cgggttcaac     360
tcccgccagc tccacca                                                    377
```

<210> SEQ ID NO 18
<211> LENGTH: 372
<212> TYPE: DNA
<213> ORGANISM: Micrococcus luteus
<220> FEATURE:
<221> NAME/KEY: misc_feature
<222> LOCATION: (1)..(372)
<223> OTHER INFORMATION: n is an unknown base

<400> SEQUENCE: 18

```
ggggctattc tggattcgac ggtgtgtgtc gcgtcgggag aagcgggccg aggatgcaga      60
gtcatctcgt caaacgctct ctgcaaacca ataagtgccg aatccaagcg cactgacttc     120
gctctcgctg cctgatcagt gatcgagtcc gtcaccccga ggtcgctgtc gcctcggatc     180
gtggcgtcag ctagatagcc actgggcgtc accctcgccg ggggtcgtga cgccgacatc     240
aatccggctg ggtccgggtt ggccgcccgt ctgcgggacg ccaggaccg agcaacaccc      300
acagcagact gcgcccggag aagacctggc aacacctcat cggacgcggg ttcaactccc     360
gcantcccac ca                                                         372
```

<210> SEQ ID NO 19
<211> LENGTH: 372
<212> TYPE: DNA
<213> ORGANISM: Mycobacterium smegmatis

<400> SEQUENCE: 19

```
tcatctcggc ttgttcgcgt gaccgggaga tccgagtaga gacatagcga actgcgcacg      60
gagaggggct gattcctgga ttcgacttcg agcatcgaat ccaggaaagc gtgccggtgc     120
aggcaagaga ccaccgtaag cgtcgttgca accaattaag cgccgattcc aatcagcgcg     180
actacgccct cgctgcctaa gcgacggctg gtctgtcaga ccgggagtgc cctcggcccg     240
gatcctggca tcagctagag ggacccaccc acgggttcgg tcgcgggacc tgtggggaca     300
tcaaacagcg actgggatcg agcctcgagg acatgccgta ggacccgggt tcaactcccg     360
ccagctccac ca                                                         372
```

<210> SEQ ID NO 20
<211> LENGTH: 355
<212> TYPE: DNA
<213> ORGANISM: Bacillus badius

```
<400> SEQUENCE: 20
gggggtgatt ctggattcga cagggatagt tcgagcttgg gctgcgagcc ggagggccgt      60
cttcgtacca acgcaaacgc ctaaatataa ctggcaaaaa agatttagct ttagctgcct     120
aatataggtt cagctgctcc tcccgctatc gtccatgtag tcgggtaagg ggtccaaact     180
tagtggacta cgccggagtt ctccgcctgg ggacaaagga agagatcaat caggctagct     240
gcccggacgc ccgtcgatag gcaaaaggaa cagtgaaccc caaatatatc gactacgctc     300
gtagacgttc aagtggcgtt atctttggac gtgggttcaa ctcccgccag ctcca          355

<210> SEQ ID NO 21
<211> LENGTH: 357
<212> TYPE: DNA
<213> ORGANISM: Bacillus brevis

<400> SEQUENCE: 21
gggggcggaa aggattcgac ggggatggta gagcatgaga agcgagccgg ggggttgcgg      60
acctcgtcac caacgcaaac gccattaact ggcaacaaac aactttctct cgctgcttaa     120
taaccagtga ggctctccca ctgcatcggc ccgtgtgccg tggatagggc tcaactttaa     180
cgggctacgc cggaggcttc cgcctggagc caaaggaaga agaccaatca ggctaggtgc     240
caggtcagcg cgtcactccg cgaatctgtc accgaaactc taaacgagtg actgcgctcg     300
gagatgctca tgtatcgctg ttttcggacg ggggttcgat tcccgccgcc tcaccca        357

<210> SEQ ID NO 22
<211> LENGTH: 354
<212> TYPE: DNA
<213> ORGANISM: Bacillus thermoleovorans

<400> SEQUENCE: 22
gggggcggaa aggattcgac gggggtaggt cgagcttaag cggcgagccg aggggggacgt    60 cctcgtaaaa acgtcaccta aagataactg gcaaacaaaa ctacgcttta gctgcctaat    120
tgctgcagct agctcctccc gccatcgccc gcgtggcgtt cgagggggctc atatggagcg   180 ggctacgccc aaatccgccg cctgaggatg agggaagaga cgaatcaggc tagccgccgg    240
gaggcctgtc ggtaggcgga acggacggcg aagcgaaata taccgactac gctcgtagat    300
gcttaagtgg cgatgcctct ggacgtgggt tcgattcccg ccgcctcccc acca           354

<210> SEQ ID NO 23
<211> LENGTH: 384
<212> TYPE: DNA
<213> ORGANISM: Clostridium innocuum

<400> SEQUENCE: 23
gggggcggaa aggattcgac ggggatatgt ctggtacaga ctgcagtcga gtggttacgt     60
aataaccaat taaatttaaa cggaaaaact aaattagcta acctctttgg tggaaaccag   120
agaatggctt tcgctgctta ataaccgata taggttcgca gccgcctctg catgcttctt    180
ccttgaccat gtggatgtgc gcgtaagacg caagggataa ggaatctggt ttgcctgaga   240
tcagattcac gaaaattctt caggcacatt catcagcgga tgttcatgac ctgctgatgt    300
cttaatcttc atggactaaa ctgtagaggt ctgtacgtgg ggctgtttct ggacaggagt    360
tcgattcccg ccgcctcacc acca                                            384
```

-continued

<210> SEQ ID NO 24
<211> LENGTH: 349
<212> TYPE: DNA
<213> ORGANISM: Clostridium lentocellum

<400> SEQUENCE: 24
gggggcggaa aggattcgac gggggtcaca tctactgggg cagccatccg tagaacgccg 60
gagtctacgt taaaagctgg cacttaaagt aaacgctgaa gataatttag caatcgctgc 120
ctaattaagg cgcagtcctc ctaggtcttc cgcagcctag atcagggctt cgactcgcgg 180
atccttcacc tggcaaagct ttgagccaac gtgaacacta tgaagctact aaaatctaga 240
gcctgtcttt gggcgctaga tggagggaat gtcaaaacaa agaatatgat ggtagagacc 300
acgctatatg ggctttcgga caggggttcg attcccgccg ccttcacca 349

<210> SEQ ID NO 25
<211> LENGTH: 358
<212> TYPE: DNA
<213> ORGANISM: Clostridium perfringens

<400> SEQUENCE: 25
ggggctgatt ctggattcga cgggggtaag atgggtttga taagcgagtc gagggaagca 60
tggtgcctcg ataataaagt atgcattaaa gataaacgca gaagataatt ttgcattagc 120
agcttaattt agcgctgctc atccttcctc aattgcccac ggttgagagt aagggtgtca 180
tttaaaagtg gggaaccgag cctagcaaag ctttgagcta ggaacggaat ttatgaagct 240
taccaaagag gaagtttgtc tgtggacgtt ctctgaggga attttaaaac acaagactac 300
actcgtagaa agtcttactg gtctgctttc ggacacgggt tcaactcccg ccactcca 358

<210> SEQ ID NO 26
<211> LENGTH: 362
<212> TYPE: DNA
<213> ORGANISM: Clostridium stercorarium

<400> SEQUENCE: 26
gggggcggaa aggattcgac ggggttattg aagcaagagt agcgggtaga ggattctcgt 60
tggcctcttt aaaaaacgag agctaaaaat aaacgcaaac aacgataact acgctttagc 120
tgctgcgtaa gtaacacgca gcccgtcggc cccggggttc ctgcgcctcg ggataccggc 180
gtcatcaagg cagggaacca gccggatcag gcttcaggtc cggtgggatt taatgaagct 240
accgacttat aaagcctgtc tctgggcgtt ataagaaggg aatgtcaaaa cagagactgc 300
acccggagaa gctcttgtgg atatggttcc ggacacgagt tcgattcccg ccgcctccac 360
ca 362

<210> SEQ ID NO 27
<211> LENGTH: 369
<212> TYPE: DNA
<213> ORGANISM: Enterococcus faecium
<220> FEATURE:
<221> NAME/KEY: misc_feature
<222> LOCATION: (1)..(369)
<223> OTHER INFORMATION: n is an unknown base

<400> SEQUENCE: 27
ggggctgatt atggattcga caggatngtt gagcttgaat tgcgtttcgt aggttacggc 60
tacgttaaaa cgttacagtt aaatataact gctaaaaacg aaaacaattc tttcgcttta 120
gctgcctaaa aaccagctag cgaagatcct cccggcatcg cccatgtgct cgggtcaggg 180

```
tcctaatcga agtgggatac gctaaatttt tccgtctgta aaatttagag gagcttacca      240
gactagcaat acaagaatgc ctgtcactcg gcacgctgta aagcgaacct ttaaatgagt      300
gtctatgaac gtagagattt aagtgggaat atgttttgga cgcgggttca actcccgcca      360
gctccacca                                                             369

<210> SEQ ID NO 28
<211> LENGTH: 353
<212> TYPE: DNA
<213> ORGANISM: Heliobacillus mobilis

<400> SEQUENCE: 28
ggggctgatt ctggattcga cggggaacgt gtttgcttgg gatgcgagcc gggttgccgc       60
caggaccgta aaagggcgg aaggctttaa ttgccgaaga taactacgct ttagctgctt      120
aattgcagtc taacctcttc tcctctgtgc tctcggtgag gatgtaaggg gtcatttaag      180
agagctggct tcgaccaatt ctcggaggtc caagcgagat ttatcgagat agcctgacca      240
acgctctgtc tgccgtgcgg aaggaaggcg aaatctaaaa cgacagacta cgctcgtagt      300
gtcctttgtg ggcatttctt cggacgcggg ttcaactccc gccagctcca cca            353

<210> SEQ ID NO 29
<211> LENGTH: 353
<212> TYPE: DNA
<213> ORGANISM: Heliospirillum gestii

<400> SEQUENCE: 29
ggggctgatt ctggattcga cggggaacgt gtttgcttag gacgcgagcc gggttgccgc       60
caggaccgta aaagggcgg aaggctttaa ttgccgaaga taactacgct ttagctgctt      120
aattgcagtc taacctcttc tcctctgtgc tctcggtgag gatgtaaggg gtcatttaag      180
agagctggct cgaaccaatt ctcggaggtt cgggtaagac ttatcgagat agcctgacca      240
acgctctgtc tgccgtgcgg aaggatggcg aaatctaaaa cgacagaata cgctcgtagt      300
gtcctttgtg ggcatttctt cggacgcggg ttcaactccc gccagctcca cca            353

<210> SEQ ID NO 30
<211> LENGTH: 368
<212> TYPE: DNA
<213> ORGANISM: Lactobacillus acidophilus

<400> SEQUENCE: 30
ggggctgatt ctggattcga caggcgtaga cccgcattga ctgcggttcg taggttacgt       60
ctacgtaaaa acgttacagt taaatataac tgcaaataac aaaaattctt acgcattagc      120
tgcttaattt agcgcatgcg ttgctctttg tcggtttact cgtggctgac actgagtatc      180
aacttagcga gttacgttta actacctcac ctgaatagtt gaaaagagtc ttagcaggtt      240
agctagtcca tactagccct gttatatggc gttttggact agtgaagttc aagtaatata      300
actatgatcg tagaggtcag tgacgagatg cgtttggaca gcgggttcaa ctcccgccag      360
ctccacca                                                             368

<210> SEQ ID NO 31
<211> LENGTH: 360
<212> TYPE: DNA
<213> ORGANISM: Staphylococcus epidermidis
```

```
<400> SEQUENCE: 31
ggggctgatt ctgcattcga caggggtccc cgagcttatt aagcgtgtgg agggttggct      60
ccgtcatcaa cacatttcgg ttaaatataa ctgacaaatc aaacaataat ttcgcagtag     120
ctgcgtaata gccactgcat cgcctaacag catctcctac gtgctgttaa cgcgattcaa     180
ccctagtagg atatgctaaa cactgccgct tgaagtctgt ttagatgaaa tataatcaag     240
ctagtatcat gttggttgtt tattgcttag catgatgcga aaattatcaa taaactacac     300
acgtagaaag atttgtatca ggacctctgg acgcgggttc aactcccgcc agctccacca     360

<210> SEQ ID NO 32
<211> LENGTH: 368
<212> TYPE: DNA
<213> ORGANISM: Streptococcus faecium

<400> SEQUENCE: 32
ggggctgatt ctggattcga caggcacagt ttgagcttga attgcgtttc gtaggttacg      60
tctacgttaa aacgttacag ttaaatataa ctgctaaaaa cgaaaacaac tcttacgctt     120
tagctgccta aaaacagtta gcgtagatcc tctcggcatc gcccatgtgc tcgagtaagg     180
gtctcaaatt tagtgggata cgtgacaact ttccgtctgt aagttgttaa agagatcatc     240
agactagcga tacagaatgc ctgtcactcg gcaagctgta aagcgaaacc acaaatgagt     300
tgactatgaa cgtagatttt taagtggcga tgtgtttgga cgcgggttca actcccgccg     360
ttccacca                                                              368

<210> SEQ ID NO 33
<211> LENGTH: 328
<212> TYPE: DNA
<213> ORGANISM: Thermoanaerobacterium saccharolyticum

<400> SEQUENCE: 33
ggggtagtag aggtaaaagt agcgagccga ggttccatct gctcgtaaaa cggtggactt      60
aaatataaac gcaaacgata atttagctta cgctgcttaa ttacaagcag ccgttcaacc     120
tttgattccc acatcaaagg attgggcgtc gatttagtgg ggaactgatt tatcaaagct     180
ttgagataaa tcggatttta tgaagctacc aaagcagtta tcctgtcact gggagaactg     240
cagagggaat gtcaaaacag tgactgcgct cggagaagct tttactgtga caccttcgga     300
ccggggttca actcccgcca gcccacca                                        328

<210> SEQ ID NO 34
<211> LENGTH: 379
<212> TYPE: DNA
<213> ORGANISM: Mycoplasma fermentans

<400> SEQUENCE: 34
ggggctgatt ctggattcga catgcattgg gtgatactaa tatcagtagt ttggcagact      60
ataatgcatc taggctttat aatcgcagaa gataaaaaag cagaagaagt taatatttct     120
tcacttatga ttgcacaaaa aatgcaatca caatcaaacc ttgctttcgc ttagttaaaa     180
gtgacaagtg gttttaaagt tgacattttc ctatatattt taaaatcggc ttttaaggag     240
aacaggagtc tgaaagggtt ccaaaaatct atattgtttg catttcggta gtatagatta     300
attagaaatg ataaactgta aaagtattg gtattgactt ggtgtgtgga ctcgggttca     360
actcccgcca gctccacca                                                  379
```

<210> SEQ ID NO 35
<211> LENGTH: 373
<212> TYPE: DNA
<213> ORGANISM: Mycoplasma hyorhinis

<400> SEQUENCE: 35

| | | | | | |
|---|---|---|---|---|---|
| ggggctgatt | ctggattcga | catacataaa | aggatataaa | ttgcagtggt | cttgtaaacc | 60 |
| ataagacaat | ttctttacta | agcggaaaag | aaaacaaaaa | agaagattat | tcattattaa | 120 |
| tgaatgcttc | aactcaatca | aatctagctt | ttgcattta | aaaaactagt | agaccaattt | 180 |
| gcttctcacg | aattgtaatc | tttatattag | agaatagtta | aaaatctgat | cactttttaa | 240 |
| tgaatttata | gatcacaggc | ttttttaatc | tttttgttat | tttagataaa | gagtcttctt | 300 |
| aaaaataact | aaactgtagg | aatttatatt | taattatgcg | tggacccggg | ttcaactccc | 360 |
| gccagctcca | cca | | | | | 373 |

<210> SEQ ID NO 36
<211> LENGTH: 399
<212> TYPE: DNA
<213> ORGANISM: Mycoplasma pirum

<400> SEQUENCE: 36

| | | | | | |
|---|---|---|---|---|---|
| ggggagtcat | ggttttgaca | tgaatgatgg | acccatagag | gcagtggggt | atgcccctta | 60 |
| tagctcaagg | tttaaattaa | ccgacaaaac | tgacgaaaac | gttgccgttg | atacaaattt | 120 |
| attaatcaac | caacaagctc | aatttaacta | cgcatttgca | tagtataaaa | aaataaattg | 180 |
| tgctactcat | tgtaattagg | ttactaaatt | actttgtttt | atatagtcct | gtaactagtt | 240 |
| ctagtgatgt | ctataaacta | gaatgagatt | tatagactta | tttgttggcg | gttgtgccat | 300 |
| agcctaaatc | aacaaagaca | atttatttat | ggtactaaac | tgtagattct | atgatgaaat | 360 |
| tatttgtgga | aacgggttcg | attcccgcca | tctccacca | | | 399 |

<210> SEQ ID NO 37
<211> LENGTH: 385
<212> TYPE: DNA
<213> ORGANISM: Mycoplasma salivarium

<400> SEQUENCE: 37

| | | | | | |
|---|---|---|---|---|---|
| ggggctgatt | ctggattcga | caggcattcg | attcattatg | ttgcagtggt | ttgcaaacca | 60 |
| taaggcacta | ggcttttttta | aacgcaaaag | accaaaaaac | agaagatcaa | gcagttgatc | 120 |
| tagcatttat | gaataattca | caaatgcaat | caaatctagt | tttcgcttag | taaaattagt | 180 |
| caatttatta | tggtgctcaa | cataataaat | ggtagtatga | gcttaatatc | atatgatttt | 240 |
| agttaatatg | ataggatttg | taactaaaact | atgttataga | aatttgtaaa | ttatatatat | 300 |
| gacataggaa | atttaattta | ctaaactgta | gatgcataat | gttgaagatg | tgtggaccgg | 360 |
| ggttcaactc | ccgccagctc | cacca | | | | 385 |

<210> SEQ ID NO 38
<211> LENGTH: 362
<212> TYPE: DNA
<213> ORGANISM: Herpetosiphon aurantiacus

<400> SEQUENCE: 38

| | | | | | |
|---|---|---|---|---|---|
| gggggcggaa | aggattcgac | ggggagggcc | aatcgtaagt | ggcaagccga | gacgctgagc | 60 |
| ctcgttaaat | cggcaacgcc | attaactggc | aaaaacactt | tccgcgctcc | tgtagcgctt | 120 |
| gctgcctaat | taaggcaaca | cgtctctact | agcctcagcc | cgatgggctt | gtagcggcga | 180 |

```
cacttagtcg ggtcgctccc ctagttatgt ctgtgggcta ggggctaaga ttaacaggct    240
ggtcgtggcc cgctttgtct atcgggtggt gcaccgataa gatttaatca atagactacg    300
cttgtagatg cttgcggttt aacttttggg acgcgggttc gattcccgcc gcctcaccac    360
ca                                                                   362
```

<210> SEQ ID NO 39
<211> LENGTH: 355
<212> TYPE: DNA
<213> ORGANISM: Thermomicrobium roseum

<400> SEQUENCE: 39

```
ggggctgatt ctggattcga cagggccgta ggtgcgagga ttgcaggtcg aggtcgccca     60
cgaactcgta aaaggggca gccaagtaac tggcgagcgc gaactcgctc tggctgcgta    120
attcacgcag ccacgtctgc ccggacccct ccctggtggg ttcggagcgg gcgccgcaag    180
accggggtgc ccctggccca agcgccgtg cgggccaggt caagcgtgat ccggctcggc    240
tgaccgggat cctgtcggtg ggagcctggc agcgacagta gaacaccgac taagcctgta    300
gcatatcctc ggctgaacgc tctggacgcg ggttcaactc ccgccagctc cacca         355
```

<210> SEQ ID NO 40
<211> LENGTH: 405
<212> TYPE: DNA
<213> ORGANISM: Chlorobium limicola

<400> SEQUENCE: 40

```
ggggctgatt ctggattcga caggatacgt gtgagatgtc gttgcactcc gagtttcagc     60
atggacggac tcgttaaaca agtctatgta ccattagatg cagacgatta ttcgtatgca    120
atggctgcct gattagcaca agttaactca gacgccatcg tcctgcggtg aatgcgctta    180
ctctgaagcc gccggatggc ataacccgcg cttgagccta cgggttcgcg caagtaagct    240
ccgtacattc atgcccgagg ggctgtgcgg gtaatttctc gggataaggg gacgaacgct    300
gctggcggtg taatcggccc acgaaaaccc aatcaccaga gatgagtgtg gtgactgcat    360
cgagcagtgt tttggacgcg ggttcaactc ccgccagctc cacca                    405
```

<210> SEQ ID NO 41
<211> LENGTH: 362
<212> TYPE: DNA
<213> ORGANISM: Pirellula staleyi

<400> SEQUENCE: 41

```
ggggctgatt ctggattcga ccggatagcc tgaagcgaat acggcgtgcc gtggttgatc     60
agatggccac gtaaaaagct gatcacaaac ttaactgccg agagcaatct cgcacttgct    120
gcctaactaa acggtagctt ccgactgagg gctttagccg gagaggccca aaagttggtc    180
accaaatccg gaccgcctcg tgccatgatc gaaacgcacg aggtcaaaaa gtttcgatc    240 tagtgcaggg tgtagccagc agctaggcga caaactgtgc aaaaatcaaa ttttctgcta    300
cgcacgtaga tgtgttcgtg aaaatgtctc gggacggggg ttcaactccc gccactccac    360
ca                                                                   362
```

<210> SEQ ID NO 42
<211> LENGTH: 346
<212> TYPE: DNA
<213> ORGANISM: Planctomyces limnophilus

```
<220> FEATURE:
<221> NAME/KEY: misc_feature
<222> LOCATION: (1)..(346)
<223> OTHER INFORMATION: n is an unknown base

<400> SEQUENCE: 42
ggggctgatt ctggattcga caacctctca agaggagcgt ggccactatg ggactcgatt    60
atgttgaatt cgtcatggat cttgaagaga ccttcgacat caaactggat gacaaacatt   120
tttcagcagt caaaacacca cgcgatttgg caatcattat tcgggatcaa ttagctgctg   180
aaggcagaat ctgggatgaa tcgaatgctt ttcgcaaaat ctcgaatttg aattggacga   240
tgttgcccga gttccggatg tggactcaaa tcaaaagctc tctaccagtt tcttttcacc   300
gactgcgtcc cagcacccgt ctcgttcaac tcccgccant ccacca               346

<210> SEQ ID NO 43
<211> LENGTH: 362
<212> TYPE: DNA
<213> ORGANISM: Planctomyces maris

<400> SEQUENCE: 43
ggggctgatt ctggattcga ctggttcacc gtatgttaag gtggcggtgc cgtggttgat    60
cagttggcca cgtaaaaagc tgatcacaat ctaattgcaa acaagcaatt ttcaatggct   120
gcttaataaa agcaaccccg gcttaggaat ctctgtctga ggagtccgac agctggtcac   180
aaaatcagac tggtatcaga tcaatgtccg ctccgtctga tacgagattc gtggtggact   240
ggtttccaac aggctctgtt tatcgtgccc gaagaaacga gactcaaacg ataaaatatg   300
caccgtagag gctttagctg agggttcaca ggacgcgggt tcaactcccg ccagctccac   360
ca                                                               362

<210> SEQ ID NO 44
<211> LENGTH: 360
<212> TYPE: DNA
<213> ORGANISM: Alcaligenes eutrophus

<400> SEQUENCE: 44
ggggttgatt ctggattcga cgtgggttac aaagcagtgg agggcatacc gaggacccgt    60
cacctcgtta atcaatggga atgcaataac tgctaacgac gaacgttacg cactggccgc   120
ttaattgcgg ccgtcctcgc actggctcgc tgacgggcta gggtcgcaag accacgcgag   180
gtcatttacg tcagataagc tccggaaggg tcacgaagcc ggggacgaaa acctagtgac   240
tcgccgtcgt agagcgtgtt cgtccgcgat gcgccggtta aatcaaatga cagaactaag   300
tatgtagaac tctctgtgga gggcttacgg acgcgggttc aactcccgcc agctccacca   360

<210> SEQ ID NO 45
<211> LENGTH: 362
<212> TYPE: DNA
<213> ORGANISM: Alcaligenes faecalis

<400> SEQUENCE: 45 ggggcggaa aggattcgac gggggtcaag aagcagcaca gggcgtgtcg agcaccagta    60
cgctcgtaaa tccactggaa aactataaac gccaacgacg agcgtttcgc tctagccgct   120
taaggctggg ccactgcact aatttgtctt tgggttaggt agggcaacct acagcagtgt   180
tatttacaaa gaatcgaatc ggtctgcgcc acgaagtccg gttctaaaac ttagtggatc   240
gccaaggaaa ggcctgtcaa ttggcatagt ccaaggttaa aacttaaaat taattgacta   300
```

```
cacatgtaga actgtctgtg gacggcttgc ggacgggggt tcgattcccg ccgcctccac    360
ca                                                                  362

<210> SEQ ID NO 46
<211> LENGTH: 366
<212> TYPE: DNA
<213> ORGANISM: Chromobacterium violaceum

<400> SEQUENCE: 46
ggggctgatt ctggattcga cgggggttgc gaagcagatg agggcatacc gggatttcag     60 tcacccccgta aaacgctgaa tttatatagt cgcaaacgac gaaacttacg ctctggcagc   120
ctaacggccg gccagacact acaacggttc gcagatgggc cggggcgtc aaaaccctgt    180 agtgtcactc tacatctgct agtgctgttc cgggttactt ggttcagtgc gaaataatag    240
gtaactcgcc aaagtccagc ctgtccgtcg gcgtggcaga ggttaaatcc aaatgacacg    300
actaagtatg tagaactcac tgtagaggac tttcggacgc gggttcaact cccgccagct    360
ccacca                                                              366

<210> SEQ ID NO 47
<211> LENGTH: 378
<212> TYPE: DNA
<213> ORGANISM: Hydrogenophaga palleroni

<400> SEQUENCE: 47
ggggctgatt ctggattcga cgtgggttcg gacgcgcagc agggcatgtc gaggttctgt     60
cacctcgtaa atcagcagaa aaaaaccaac tgcaaacgac gaacgtttcg cactcgccgc    120
ttaaacaccg gtgagccttg caacagcagg ccgatgggct gggcaagggg gtcgcaagac    180
ctcccggctg caaggtaatt tacatcggct ggttctgcgt cgggcaccttt ggcgcaggat    240 gagattcaag gatgctggct tcccgtttag cgtgccactg cgcgactcgg cggcgagac    300 ccaaatcaga cggctacaca tgtagaactg ctcgaaaaag gcttgcggac gggggttcaa    360
ctcccgccag ctccacca                                                 378

<210> SEQ ID NO 48
<211> LENGTH: 365
<212> TYPE: DNA
<213> ORGANISM: Methylobacillus glycogenes

<400> SEQUENCE: 48
gggggcggaa aggattcgac gggggttgca aagcagcgca gggcataccg aggcctagtc     60
acctcgtaaa taaactagaa caagtatagt cgcaaacgac gaaacttacg ctctagccgc    120
ttaatcccgg ctggacgctg caccgaaggg cctctcggtc gggtggggta acccacagca    180
gcgtcattaa gagaggatcg tgcgatattg ggttacttaa tatcgtatta aatccaaggt    240
aactcgcctg ctgtttgctt gctcgttggt gagcatcagg ttaaatcaaa caacacagct    300
aagtatgtag aactgtctgt ggagggcttg cggacggggg ttcgattccc gccgcctcac    360
cacca                                                               365

<210> SEQ ID NO 49
<211> LENGTH: 362
<212> TYPE: DNA
<213> ORGANISM: Nitrosomonas cryotolerans
```

```
<400> SEQUENCE: 49
ggggctgatt ctggattcga cgtgggttgc aaagcagcgc agggcatacc gaggaccaga      60
atacctcgta aatacatctg gaaaaaaata gtcgcaaacg acgaaaacta cgctttagcc     120
gcttaatacg gctagcctct gcaccgatgg gccttaacgt cgggtctggc aacagacagc     180
agagtcatta gcaaggatcg cgttctgtag ggtcacttta cagaacgtta acaataggt      240 gactcgcctg ccatcagccc gccagctggc ggttgtcagg ttaaattaaa gagcatggct     300
aagtatgtag aactgtctgt agaggacttg cggacgcggg ttcaactccc gccagtccac     360
ca                                                                    362

<210> SEQ ID NO 50
<211> LENGTH: 378
<212> TYPE: DNA
<213> ORGANISM: Pseudomonas testosteroni

<400> SEQUENCE: 50
ggggctgatt ctggattcga cgtgggttcg ggaccggtgc ggtgcatgtc gagcttgagt      60
gacgctcgta aatctccatt caaaaaacta actgcaaacg acgaacgttt cgcactcgcc     120
gcttaatccg gtgagccttg caacagcacg ctagtgggct gggcaagggg gtagcaatac     180
ctcccggctg caagggaatt tcattagct ggctggatac cgggcttctt ggtatttggc      240
gagattttag gaagctggct acccaagcag cgtgtgcctg cggggtttgg gtggcgagat     300
ttaaaacaga gcactaaaca tgtagatctg tccggcgaag gcttacggac gcgggttcaa     360
ctcccgccag ctccacca                                                   378

<210> SEQ ID NO 51
<211> LENGTH: 360
<212> TYPE: DNA
<213> ORGANISM: Ralstonia pickettii

<400> SEQUENCE: 51
gggggcggaa aggattcgac gggggttgcg aagcagcgga gggcataccg aggaccccgtc     60 acctcgttaa tcaatgggaa tgcaataact gctaacgacg aacgttacgc actggcagcc    120
taagggccgc cgtcctcgca ctggctcgct gacgggctag ggtcgcaaga ccagcgaggt    180
catttacgtc agataagctt taggtgagtc acggcctag agacgaaaac ttagtgaatc     240
gccgtcgtag agcgtgttcg tccgcgatgc ggcggttaaa tcaaatgaca gaactaagta    300
tgtagaactc tctgtggagg gcttgcggac gcgggttcga ttcccgccgc ctcaccacca    360

<210> SEQ ID NO 52
<211> LENGTH: 386
<212> TYPE: DNA
<213> ORGANISM: Variovorax paradoxus

<400> SEQUENCE: 52
ggggctgatt ctggattcga cgtgggttcg gagtcgcagc ggggcatgtc gagctgaatg      60
cgctcgtaaa acagattcaa acaaactaac tgcaaacgac gaacgtttcg cactcgctgc    120
ttaattgcca gtgagccttg caacagttgg ccgatgggct gggcaagggg gtctggagca    180
atcctgacct ccccggctgca aggataacta catgggctgg ctccgatccg ggtaccttgg    240
gtcggggcga gaaaatagg tactggcgtc cggtttagcg tgtgactgcg cgactccgga     300
agcgagactc aaaacagatc actaaacatg tagaactgcg cgatgaaggc ttgcggacgg    360
gggttcaact cccgccagct ccacca                                          386
```

```
<210> SEQ ID NO 53
<211> LENGTH: 346
<212> TYPE: DNA
<213> ORGANISM: Bdellovibrio bacteriovirus

<400> SEQUENCE: 53
gggggcggaa aggattcgac gggggtgctg aagcataagg agcataccgg ggcggatgag      60
gacctcgtta aaacgtcca ctttgtaatt ggcaacgatt acgcacttgc agcttaatta     120
agcagcacga tcaaccttgt ggtggttccg cacttggatt gatcgtcatt tagggacctc     180
ggcgtgttgg gttttctcca gcagacatgc ttaaatttac tggggagag gtcttaggga      240 ttttgtctgt ggaagcccga ggaccaatct aaaacactga ctaagtatgt agcgccttat     300
cgtggatcat ttgcggacgg gggttcgatt cccgccgcct ccacca                    346

<210> SEQ ID NO 54
<211> LENGTH: 366
<212> TYPE: DNA
<213> ORGANISM: Myxococcus xanthus

<400> SEQUENCE: 54
gggggcggaa aggattcgac gggggcattg aagttcgaga cgcgtgccga gcttgtcagg      60
tagctcgtaa attcaacccg gcaaagacac aaaagccaac gacaacgttg agctcgcgct     120
ggctgcctaa aaacagccca tagtgcgcgg tcccccgcc ctcggcctgt ggggttggga      180
cagaccgtca taatgcaggc tggctgccga gggtgcctgg acccgaggtg gcagatctt      240 cccaggaccg gctctgagta tcccgtccgt gggagcctca gggacgtagc aaatcgcgga     300
ctacgcacgt agggtcgaag agcggacggc tttcggacgc gggttcgatt cccgccgcct     360
ccacca                                                                 366

<210> SEQ ID NO 55
<211> LENGTH: 380
<212> TYPE: DNA
<213> ORGANISM: Sulfurospirillum deleyianum

<400> SEQUENCE: 55
ggggctgatt ctggattcga caggagtagt tttagcttat ggctgcatgt cgggagtgag      60
ggtcttccgt tacacaacct tcaaacaata actgctaaca acagtaacta tcgtcctgct     120
tacgcgctag ctgcgtaagt ttaacaaata atggactgct ctccccttg atgctatctt      180 aggaggtctt ggagagtatc atagatttga tagctatatt acatgaacgc ctttacatgt     240
aatgaagtta aaggctcgtt ttgcgtagtt ttctgattgt tgtacgaagc aaaattaaac     300
actatcaaca atatctaagc atgtagacgt cataggtggc tattttttgga ctgcgggttc     360 aactcccgcc agctccacca                                                  380

<210> SEQ ID NO 56
<211> LENGTH: 359
<212> TYPE: DNA
<213> ORGANISM: Chromatium vinosum

<400> SEQUENCE: 56
ggggctgatt ctggattcga cgtgggtcgc gaaacctaag gtgcatgccg aggtgcggtt      60
gacctcgtaa acccctccgc aaacttatag ttgccaacga cgacaactac gctctcgctg     120
cttaatccca gcgggcctct gaccgtcact tgcctgtggg cggcggattc caggggtaac     180
ctcacacagg atcgtggtga cgggagtccg gacctgatcc actaaaacct aacggaatcg     240
```

```
ccgactgatc gccctgccct tcgggcggca gaaggctaaa aacaatagag tgggctaagc    300
atgtaggacc gagggcagag ggcttgcgga cgcgggttca actcccgcca gctccacca    359

<210> SEQ ID NO 57
<211> LENGTH: 395
<212> TYPE: DNA
<213> ORGANISM: Pseudomonas fluorescens

<400> SEQUENCE: 57
ggggctgatt ctggattcga cgccggttgc gaacctttag gtgcatgccg agttggtaac     60
agaactcgta atccactgt tgcaactttc tatagttgcc aatgacgaaa cctacgggga    120
atacgctctc gctgcgtaag cagccttagc ccttccctcc tggtaccttc gggtccagca    180
atcatcaggg gatgtctgta aacccaaagt gattgtcata tagaacagaa tcgccgtgca    240
gtacgttgtg gacgaagcgg ctaaaactta cacaactcgc ccaaagcacc ctgcccgtcg    300
ggtcgctgag ggttaactta atagacacgg ctacgcatgt agtaccgaca gcagagtact    360
ggcggacgcg ggttcaactc ccgccagctc cacca                              395

<210> SEQ ID NO 58
<211> LENGTH: 362
<212> TYPE: DNA
<213> ORGANISM: Borrelia afzelii

<400> SEQUENCE: 58
ggggctgatt ctggattcga ctgaaaatgc taatattgta agttgcaagc agagggaatc     60
tcttaaaact tctaaaataa atgcaaaaaa taataacttt acaagttcaa accttgtaat    120
ggctgcttaa gttagcagag agttttgttg aatttggctt tgagattcac ttatactctt    180
ttagacatcg aagcttgctt aaaaatgttt tcaagttgat ttttagggac ttttatactt    240
gagagcaatt tggcggtttg ctagtatttc caaaccatat tgcttagtaa aatactagat    300
aagcttgtag aagcttatag tattgttttt aggacgcggg ttcaactccc gccagtccac    360
ca                                                                  362

<210> SEQ ID NO 59
<211> LENGTH: 363
<212> TYPE: DNA
<213> ORGANISM: Borrelia crocidurae

<400> SEQUENCE: 59
ggggctgatt ctggattcga ctaagaactt tagtagcata aatggcaagc agagtgaatc     60
tcttaaaact tctttaataa atgcaaaaaa taataacttt acaagttcag atcttgtaat    120
ggctgcttaa tttagcagag agttttgttg gattttgctt tgaggttcaa cttatactct    180
ttaagacatc aaagtatgcc taaaaatgtt tcaagttgat ttttagggac ctttaaactt    240
gagagtaatt tggtggtttg cttgttttcc aagccttatt gcttttttcta aaaattagct    300 aagcttgtag atatttatga tattattttt aggacgcggg ttcaactccc gccagttcca    360
cca                                                                 363

<210> SEQ ID NO 60
<211> LENGTH: 365
<212> TYPE: DNA
<213> ORGANISM: Borrelia hermsii
```

-continued

```
<400> SEQUENCE: 60
ggggctgatt ctggattcga ctaaaaactt tagtagcata aattgcaagc agagggaatc    60
tcttaaaact tctttaataa atgcaagaaa taataacttt acaagttcaa atcttgtaat   120
ggctgcttaa attagcagag agttctgctg gattttgctt tgaggttcag cttatactct   180
tttaagacat caaagcttgc ttaaaaatat ttcaagttga tttttaggga cttttaaatt   240
tgagagtaat ttggcggttt gctagttttt ccaaaccttta ttacttaaag aaaacactag  300
ctaagcttgt agatatttat gatattattt ttaggacgcg ggttcaactc ccgccagctc   360
cacca                                                                365

<210> SEQ ID NO 61
<211> LENGTH: 363
<212> TYPE: DNA
<213> ORGANISM: Borrelia garinii

<400> SEQUENCE: 61
ggggctgatt ctggattcga ctgaaaatgc gaatattgta agttgcaggc agagggaatc    60
tcttaaaact tctaaaataa atgcaaaaaa taataacttt acaagctcaa accttgtaat   120
ggctgcttaa gttagcaggg agtttcgttg aatttggctt tgaggttcac ttatactctt   180
ttcgatatcg aagcttgctt aaaaatgttt tcaagttaat ttttagggac ttttgtactt   240
gagagcaatt tggcggtttg ctagtatttc caaaccatat tgcttaagta aaatgctaga   300
taagcttgta gaagcttata atattgtttt taggacgcgg gttcaactcc cgccagtcca   360
cca                                                                 363

<210> SEQ ID NO 62
<211> LENGTH: 357
<212> TYPE: DNA
<213> ORGANISM: Thermodesulfobacterium commune

<400> SEQUENCE: 62
gggggcggaa aggattcgac ggggataggt aggattaaac agcaggccgt ggtcgcaccc    60
aaccacgtta aatagggtgc aaaaacacaa ctgccaacga atacgcctac gctttggcag   120
cctaagcgtg ctgccacgca cctttagacc ttgcctgtgg gtctaaaggt gtgtgaccta   180
acaggctttg ggaggcttaa tcggtggggt taagcctccc gagattacat cccacctggt   240
agggttgctt ggtgcctgtg acaagcaccc tacgagattt cccacaggc taagcctgta   300 gcggtttaat ctgaactatc tccggacgcg ggttcgattc cgccgcctc cccacca       357

<210> SEQ ID NO 63
<211> LENGTH: 358
<212> TYPE: DNA
<213> ORGANISM: Thermotoga neapolitana
<220> FEATURE:
<221> NAME/KEY: misc_feature
<222> LOCATION: (1)..(358)
<223> OTHER INFORMATION: n is an unknown base

<400> SEQUENCE: 63
gggggcggaa aggattcgac ggggatggag tcccctggga agcgagccga ggtccccacc    60
tcctcgtaaa aaaggtggga acacgaataa gtgccaacga acctgttgct gttgccgcct   120
aatagatagg cggccgtcct ctccggagtt ggctgggctc cggaagaggg cgtgagggat   180
ccagcctacc gatctgggct ccgccttccg gcccggatcg ggaaggttca ggaaggctgt   240
```
gggaagcgac accctgcccg tgggggtcc ttcccgagac acgaaacacg ggctgcgctc    300
ggagaagccc aggggcctcc atcttcngac gcgggttcga ttcccgccac ctccacca    358

<210> SEQ ID NO 64
<211> LENGTH: 347
<212> TYPE: DNA
<213> ORGANISM: Deinococcus proteolyticus

<400> SEQUENCE: 64
gggggcggaa aggattcgac gggggaacgg aaagcgctgc tgcgtgccga ggagccgttg    60
gcctcgtaaa caaacggcaa agccattaac tggcgaaaat aactacgctc tcgctgctta    120
agtgagacag tgaccacgta gccccgcctt tggcgacgtg tgaactgaga caaaagaagg    180
ctagcttagg tgaggttcca tagccaaaag tgaaaccaaa tggaaataag gcggacggca    240
gcctgtttgc tggcagccca ggcccgacaa tttaagagca gactacgcac gtagatgcac    300
gctggatgga cctttggacg cgggttcgat tcccgccagc tccacca    347

<210> SEQ ID NO 65
<211> LENGTH: 352
<212> TYPE: DNA
<213> ORGANISM: Prosthecobacter fusiformis

<400> SEQUENCE: 65
ggggctgatt ctggattcga cggggagtac aaggatcaaa agctgcaagc cgaggtgccg    60
ttacctcgta aacaacggc aaaaaagaag tgccaacaca aatttagcat tagctgctta    120
atttagcagc tacgctcttc taacccgggc tggcagggtt agaagggtgt cataatgagc    180
cagctgcccc ttccgactcc cctaaggaag ggaaagatgt aggggatagg tgcttacaga    240
atcctgcggg agggagtctg taagtgccga aaagttaaaa ctcccgctaa gcttgtagag    300
gcttttgatt cttgctctct ggacgcgggt tcaactcccg ccagctccac ca    352

<210> SEQ ID NO 66
<211> LENGTH: 329
<212> TYPE: DNA
<213> ORGANISM: Verrucomicrobium spinosum
<220> FEATURE:
<221> NAME/KEY: misc_feature
<222> LOCATION: (1)..(329)
<223> OTHER INFORMATION: n is an unknown base

<400> SEQUENCE: 66
gggnnnnatt tggaattcgc cgaatgctag aagtggaggc tgcatgccgc ggatgattcg    60
ttggccgctt taccaattcg gatcaaacaa ctaaatgcgg actctaacga gcttgccctc    120
gccgcttaat tgacggtgac gttcctccag tgaagtctgt gaattggagg agcgactact    180
tacaggctgg ccaaaagagc gggcgaccgg ccccaaggcg agatctacag gccgctggat    240
ggacggcatc ctggcagtag gaggctggac atcgagatca atnattgcc tgagcatgga    300 gacgctttca taaaggngtt cggacaggg    329

<210> SEQ ID NO 67
<211> LENGTH: 318
<212> TYPE: RNA
<213> ORGANISM: Thermoanaerobacterium saccharolyticum

<400> SEQUENCE: 67 cgggggguagu agagguaaaa guagcgagcc gagguuccau cugcucguaa aacgguggac    60
uuaaauauaa acgcaaacga uaauuuagcu uacgcugcuu aauuacaagc agccguucaa    120

-continued

```
ccuuugauuc ccacaucaaa ggauugggcg ucgauuuagu ggggaacuga uuuaucaaag    180
cuuugagaua aaucggauuu uaugaagcua ccaaagcagu uauccuguca cugggagaac    240
ugcagaggga augucaaaac agugacugcg cucggagaag cuuuuacugu gacaccuucg    300 gaccggggui caacuccc                                                  318
```

```
<210> SEQ ID NO 68
<211> LENGTH: 187
<212> TYPE: RNA
<213> ORGANISM: Clostridium acetobutylicum

<400> SEQUENCE: 68
aaucuggcgu cgagagcggg gaaacgagcc uuacaaagcu uugaguaagg aacggaauuu     60
augaagcuac ugaagugaaa agcuuguuug uaggcguuuc auggagggaa uguuaaaaua    120
caaacugcac ucggagaugc uuaaaugaaa ccauuuucgg acaggggiuuc gauuccccuc   180 gccucca                                                              187
```

```
<210> SEQ ID NO 69
<211> LENGTH: 335
<212> TYPE: RNA
<213> ORGANISM: Clostridium stercorarium

<400> SEQUENCE: 69
cgggguuauu gaagcaagag uagcggguag aggauucucg uuggccucuu uaaaaaacga     60
gagcuaaaaa uaaacgcaaa caacgauaac uacgcuuuag cugcugcgua aguaacacgc    120
agcccgucgg ccccgggguu ccugcgccuc gggauaccgg cgucaucaag gcagggaacc    180
agccggauca ggcuucaggu ccggugggau uuaaugaagc uaccgacuua uaaagccugu    240
cucugggcgu uauaagaagg gaaugucaaa acagagacac caaugcaccc ggagaagcuc    300
uuguggauau gguuccggac acgaguucga uuccc                               335
```

```
<210> SEQ ID NO 70
<211> LENGTH: 336
<212> TYPE: RNA
<213> ORGANISM: Clostridium perfringens

<400> SEQUENCE: 70 cgggggguaag augggguuuga uaagcgaguc gagggaagca uggugccucg auaauaaagu   60
augcauuaaa gauaaacgca gaagauaauu uugcauuagc agcuuaauuu agcgcugcuc    120
auccuuccuc aauugcccac gguugagagu aagggguguca uuuaaaagug gggaaccgag   180
ccuagcaaag cuuugagcua ggaacggaau uuaugaagcu uagaggaagu uugucugugg    240
acguucucug agggaauuuu aaaacacaag acacuaaaau cuaguacacu cguagaaagu    300
cuuacugguc ugcuuucgga cacggguuca acuccc                              336
```

```
<210> SEQ ID NO 71
<211> LENGTH: 305
<212> TYPE: RNA
<213> ORGANISM: Clostridium lentocellum

<400> SEQUENCE: 71
cgggggucac aucuacuggg gcagccaucc guagaacgcc ggagucuacg uuaaaagcug     60
gcacuuaaag uaaacgcuga agauaauuua gcaaucgcug ccuaauuaag gcgcaguccu    120
ccuaggucuu ccgcagccua gaucagggcu ucgacucgcg gauccuucac cuggcaaagc    180
uuugagccaa cgugaacacu augaagcuag ccugucuuug ggcgcuagau ggagggaaug    240
```

```
ucaaaacaaa gaauaugaug guagagacca cgcuauaugg gcuuucggac aggggUucga    300
uuccc                                                                305

<210> SEQ ID NO 72
<211> LENGTH: 319
<212> TYPE: RNA
<213> ORGANISM: Heliobacillus mobilis

<400> SEQUENCE: 72
cggggaacgu guuugcuugg gaugcgagcc ggguugccgc caggaccgua aaaagggcgg    60
aaggcuuuaa uugccgaaga uaacuacgcu uuagcgcuu uauugcaguc uaaccucuuc    120
uccucugugc ucucggugag gauguaaggg gucauuuaag agagcuggcu ucgaccaauu    180
cucggagguc caagcgagau uuaucgagau agccugacca acgcucuguc ugccgugcgg    240
aaggaaggcg aaaucuaaaa cgacagauac gcucguagug uccuuugugg gcauuucuuc    300
ggacgcgggu ucaacuccc                                                319

<210> SEQ ID NO 73
<211> LENGTH: 321
<212> TYPE: RNA
<213> ORGANISM: Heliospirillum gestii

<400> SEQUENCE: 73
cggggaacgu guuugcuuag gacgcgagcc ggguugccgc caggaccgua aaaagggcgg    60
aaggcuuuaa uugccgaaga uaacuacgcu uuagcgcuu aauugcaguc uaaccucuuc    120
uccucugugc ucucggugag gauguaaggg gucauuuaag agagcuggcu cgaaccaauu    180
cucggagguu cgguaagac uuaucgagau cagccugacc aacgcucugu cugccgugcg    240
gaaggauggc gaaaucuaaa acgacagaau acgcucguag uguccuuugu gggcauuucu    300
ucggacgcgg guucaacucc c                                             321

<210> SEQ ID NO 74
<211> LENGTH: 325
<212> TYPE: RNA
<213> ORGANISM: Brevibacillus brevis

<400> SEQUENCE: 74
cggggauggu agagcaugag aagcgagccg gggggUugcg gaccucguca ccaacgcaaa    60
cgccauuaac uggcaacaaa caacuuucuc ucgcugcuua auaaccagug aggcucuccc    120
acugcaucgg cccgugugcc guggauaggg ucaacuuua acgggcuacg ccggaggcuu    180
ccgccuggag ccaaaggaag aagaccaauc aggcuaggug ccaggucagc gcgucacucc    240
gcgaaucugu caccgaaacu cuaaacgagu gacugcgcuc ggagaugcuc auguaucgcu    300 guuucggac gggggUucga uuccc                                          325

<210> SEQ ID NO 75
<211> LENGTH: 360
<212> TYPE: RNA
<213> ORGANISM: Bacillus subtilis

<400> SEQUENCE: 75
ggggacguua cggauucgac aggauggau cgagcuugag cugcgagccg agaggcgauc    60
ucguaaacac gcacuuaaau auaacggca aacuaacag uuuuaaccaa acguagcau     120 uagcugccua auaagcgcag cgagcucuuc cugacauugc cuaugugucu gugaagagca    180
cauccaagua ggcuacgcuu gcguccccgu cugagaacgu aagaagagau gaacagacua    240
```

```
gcucucggaa ggcccgcccg caggcaagaa gaugagugaa accauaaaua ugcaggcuac    300
gcucguagac gcuuaaguaa ucgauguuuc uggacguggg uucgacuccc accgucucca    360

<210> SEQ ID NO 76
<211> LENGTH: 325
<212> TYPE: RNA
<213> ORGANISM: Bacillus badius

<400> SEQUENCE: 76
cagggauagu ucgagcuugg gcugcgagcc ggagggccgu cuucguacca acgcaaacgc     60
cuaaauauaa cuggcaaaaa agauuuagcu uuagcugccu aauauagguu cagcugcucc    120
ucccgcuauc guccauguag ucgdgguaagg gguccaaacu uaguggacua cgccggaguu    180
cuccgccugg ggacaaagga agagaucaau caggcuagcu gcccgacgc  ccgucgauag    240 gcaaaaggaa cagugaaccc caaauauauc gacuacgcuc guagacguuc aagug9cguu    300 aucuuuggac gugggUucaa cuccc                                         325

<210> SEQ ID NO 77
<211> LENGTH: 341
<212> TYPE: RNA
<213> ORGANISM: Bacillus megaterium

<400> SEQUENCE: 77
ggggacguua cggauucgac agggUaguuc gagcuuaggu ugcgagucga ggagauggcc     60
ucguuaaaac aucaacgcca auaauaacug gcaaaucuaa caauaacuuc gcuuuagcug    120
cauaauagua gcuuagcguu ccucccucca ucgcccaugu gguagggUaa gggacucacu    180
uuaagugggc uacgccggag uucgccgucu gaggacgaag gaagagaaua ucagagacuag    240 cgacugggac gccuguuggu aggcagaaca gcucgcgaau gaucaauaug ccaacagccg    300
uacacucgua gacgcuuaag uggccauauu ucuggacgug g                       341

<210> SEQ ID NO 78
<211> LENGTH: 315
<212> TYPE: RNA
<213> ORGANISM: Bacillus thermoleovorans

<400> SEQUENCE: 78
cgggggUagg ucgagcuuaa gcggcgagcc gaggggdacg uccucguaaa aacgucaccu     60
aaagauaacu ggcaaacaaa acuacgcuuu agcugccuaa uugcugcagc uagcuccucc    120
cgccaucgcc cgcguggcgu ucgaggggcu cauauggagc gggcuacgcc caaauccgcc    180
gccugaggau gagggaagag acgaaucagg cuccggagg ccugucggua ggcggaacgg     240
acggcgaagc gaaauauacc gacuacgcuc guagaugcuu aaguggcgau gccucuggac    300
gUgggUUcga uuccc                                                    315

<210> SEQ ID NO 79
<211> LENGTH: 335
<212> TYPE: RNA
<213> ORGANISM: Enterococcus faecium

<400> SEQUENCE: 79
caggcacagu uugagcuuga auugcguuuc guagguuacg cuacguuaa aacguuacag      60 uuaaauauaa cugcuaaaaa cgaaaacaac ucuuacgcuu uagcugccua aaaacaguua    120
gcguagaucc ucucggcauc gcccaugugc ucgaguaagg gucucaaauu uaguggggaua    180 cgugacaacu uuccgucugu aaguuguuaa agagaucauc agacuagcga uacagaaugc    240
```

```
cugucacucg gcaagcugua aagcgaaacc acaaaugagu ugauaugaac guagauuuuu    300
aaguggcgau uguuuggac gcgguucaa cuccc                                335

<210> SEQ ID NO 80
<211> LENGTH: 364
<212> TYPE: RNA
<213> ORGANISM: Enterococcus faecalis

<400> SEQUENCE: 80
gggggcguua cggauucgac aggcauaguu gagcuugaau ugcguuucgu agguuacggc    60
uacguuaaaa cguuacaguu aaauauaacu gcuaaaaacg aaaacaauuc uuucgcuuua   120
gcugccuaaa aaccagcuag cgaagauccu cccggcaucg cccaugugcu cggucaggg    180 uccuaaaucga agugggauac gcuaaauuuu ccgucugua aaauuuagag gagcuuacca   240
gacucagcaa uacagaaugc cugucacucg gcacgcugua aagcgaaccu uuaaaugagu   300
guuaugaacg uagagauuua aguggcaaua uguuuggacg cgguucgac ucccgccguc    360 ucca                                                                364

<210> SEQ ID NO 81
<211> LENGTH: 346
<212> TYPE: RNA
<213> ORGANISM: Streptococcus pyogenes

<400> SEQUENCE: 81 ggggduuguua cggauucgac aggcauuaug aggcauguuu ugcgucccau cggcagaugu    60
aaauugccag uuaaauauaa cugcaaaaaa uacaaacucu uacgcuuuag cugccuaaaa   120
accagcuagc gugacuucua caagauugcu uguguccugu uagaagucuc aaaauagcaa   180
gcuacgguua cgaaauuguc uaguuucgug acaagagauu gauagacucc gcaaacuaau   240
ggcuugaguu augugucuuu aguuuguuaa augaagacau aaccauggaa cguagacaaa   300
uauguuggca gguguuugga cgugggucg acucccacca gcucca                   346

<210> SEQ ID NO 82
<211> LENGTH: 344
<212> TYPE: RNA
<213> ORGANISM: Streptococcus pneumoniae

<400> SEQUENCE: 82
ggggucguua cggauucgac aggcauuaug aggcauauuu ugcgacucgu guggcgacgu    60
aaacgcucag uuaaauauaa cugcaaaaaa uaacacuucu uacgcucuag cugccuaaaa   120
accagcaggc gugacccgau uuggauugcu cguguucaau gacaggucuu auuauuagcg   180
agauacgauu aagccuuguc uagcgguuug auaagagauu gauagacucg caguuucuag   240
acuugaguua uguucgagg ggcuguuaaa auaaaucuaua acuauggluug uagacaaaua   300 uguuggcagg uguuuggacg uggguucgac ucccaccggc ucca                    344

<210> SEQ ID NO 83
<211> LENGTH: 364
<212> TYPE: RNA
<213> ORGANISM: Streptococcus gordonii

<400> SEQUENCE: 83
ggggucguua cggauucgac aggcauuaug aggcauauuu ugcgacucau cuagcggaug    60
uaaaacgcca guuaaauaua acugcaaaaa auaauacuuc uuacgcuuua gcugccuaaa   120
aaccagcggg cgugacccga uucggauugc uuguguucuga ugacaggucu uauuauuagc   180
```

```
aagcuacggu agaaucuugu cuagugauuu uacaagagau ugauagacua cguuagaacu    240
gagucagccg cuugauuugg gcuugaguua ugugucaaaa ucaaguuaaa acaauacaua    300
gcuaugguug uagacaaaua uguuggcaga uguuggacg ugggUucgac ucccaccggc    360
ucca                                                                364

<210> SEQ ID NO 84
<211> LENGTH: 329
<212> TYPE: RNA
<213> ORGANISM: Streptococcus mutans

<400> SEQUENCE: 84
ggggucguua cggauucgac aggcauuaug agaccuauuu ugcgacucau cuagcggaug     60
uaaaacgcca guuaaauaua acugcaaaaa auacaaauuc uuacgcagua gcugccuaaa    120
aaccagccug ugugaucaau aacaaauugc uuguguuugu ugauuggucu uauuguuaac    180
aagcugcugu ucuaaaagag uucuacugac uccgcaucgu uagaguuuga guuauguauu    240 guaacgguguu uaaauaaaca cauaaccuau aguuguagac aaaugggUuu gcagauguuu    300
ggacgugggu ucgacucccca ccggcucca                                    329

<210> SEQ ID NO 85
<211> LENGTH: 328
<212> TYPE: RNA
<213> ORGANISM: Staphylococcus epidermidis

<400> SEQUENCE: 85 caggggucec cgagcuuauu aagcgugucg gagggUuggc uccgucauca acacauuucg     60
guuaaauaua acugacaaau caaacaauaa uuucgcagua gcugcguaau agccacugca    120
ucgccuaaca gcaucccua cgugcuguua acgcgauuca acccuaguag gauaugcuaa    180
acacugccgc uugaagucug uuuagaugaa auauaaucaa gcuaguauca guuggUuugu    240
uuauugcuua gcaugaugcg aaaauuauca auaaacuaca cacguagaaa gauuuguauc    300
aggaccucug gacgcgggUu caacuccec                                     328

<210> SEQ ID NO 86
<211> LENGTH: 359
<212> TYPE: RNA
<213> ORGANISM: Staphylococcus aureus

<400> SEQUENCE: 86
ggggacguuc auggauucga caggggucec cgagcucauu aagcgugUuc ggagggUugu     60
cuucgucauc aacacacaca guuuauaaua acuggcaaau caaacaauaa uuucgcagua    120
gcugccuaau cgcacucugc aucgccuaac agcauuccu augugcuguu aacgcgauuc    180
aaccuuaaua ggauaugcua aacacugccg uuugaagucu guuuagaaga aacuuaauca    240
aacuagcauc auguuggUug uuuaucacuu uucaugaugc gaaaccuauc gauaaacuac    300
acacguagaa agaguguauuu caggaccuuu ggacgcgggUu caaucccg ccgucucca    359

<210> SEQ ID NO 87
<211> LENGTH: 334
<212> TYPE: RNA
<213> ORGANISM: Lactobacillus acidophilus

<400> SEQUENCE: 87
caggcguaga cccgcauuga cugcgguucg uagguuacgu cuacguaaaa acguuacagu     60
uaaauauaac ugcaaauaac aaaaaauucu uacgcauuagc ugcuuaauuu agcgcaugcg    120
```

```
uugcucuuug ucgguuuacu cguggcugac acugaguauc aacuuagcga guuacguuua    180
acuaccucac cugaauaguu gaaaagaguc uuagcagguu agcuagucca uacuagcccu    240
guuauauggc guuuuggacu agugaaguuc aaguaauaua acuaugaucg uagaggucag    300
ugacgagaug cguuuggaca ggggguucaac uccc                              334
```

<210> SEQ ID NO 88
<211> LENGTH: 347
<212> TYPE: RNA
<213> ORGANISM: Aquifex aeolicus

<400> SEQUENCE: 88

```
ggggcggaa aggauucgac ggggacaggc gguccccgag gagcaggccg gguggcuccc    60
guaacagccg cuaaaacagc ucccgaagcu gaacucgcuc ucgcugccua auuaaacggc   120
agcgcguccc cgguagguuu gcggguggcc uaccggaggg cgucagagac acccgcucgg   180
gcuacucggu cgcacgggc ugaguagcug acaccuaacc cgugcuaccc ucggggagcu    240
ugcccguggg cgacccgagg ggaaauccug aacacgggcu aagccuguag agccucggau   300
guggccgccg uccucggacg cgdgguucgau ucccgccgcc uccacca                 347
```

<210> SEQ ID NO 89
<211> LENGTH: 355
<212> TYPE: RNA
<213> ORGANISM: Thermotoga maritima

<400> SEQUENCE: 89

```
ggggcgaac gguuucgacg gggauggagu ccccugggaa gcgagccgag guccccaccu    60
ccucguaaaa aaggugggac aaagaauaag ugccaacgaa ccuguugcug uugccgcuua   120
auagauaagc ggccguccuc uccgaaguug gcugggcuuc ggaagagggc gugagagauc   180
cagccuaccg auucaguucg ccuuccggcc ugaaucggga aaacucagga aggcuguggg   240
agaggacacc cugcccgugg gaggucccuc ccgagagcga aaacacgggc ugcgcucgga   300
gaagcccagg ggccuccauc uucggacggg gguucgaauc ccccgccuc cacca         355
```

<210> SEQ ID NO 90
<211> LENGTH: 355
<212> TYPE: RNA
<213> ORGANISM: Thermotoga neapolitana

<400> SEQUENCE: 90

```
ggggcggaa aggauucgac ggggauggag uccccuggga agcgagccga gguccccacc    60
uccucguaaa aaagguggga acacgaauaa gugccaacga accuguugcu guugccgccu   120
aauagauagg cggccguccu ucccggaguu ggcugggcuc cggaagaggg cgugagggau   180
ccagccuacc gaucugggcu ccgccuuccg gcccggaucg ggaagguuca ggaaggcugu   240
gggaagcgac acccgcccg uggggggucc uucccgagac acgaaacacg ggcugcgcuc   300
ggagaagccc aggggccucc aucuucggac gggguucga ucccgccgc cucca          355
```

<210> SEQ ID NO 91
<211> LENGTH: 350
<212> TYPE: RNA
<213> ORGANISM: Thermus thermophilus

<400> SEQUENCE: 91

```
ggggugaaa cggucucgac ggggucgcc gagggcgugg cugcgcgccg aggugcgggu     60
ggccucguaa aaacccgcaa cggcauaacu gccaacacca acuacgcucu cgcggcuuaa   120
```

```
ugaccgcgac cucgcccggu agcccugccg ggggcucacc ggaagcgggg acacaaaccc    180
ggcuagcccg gggccacgcc cucuaaccc  gggcgaagcu ugaaggggc  ucgcuccugg    240
ccgcccgucc gcgggccaag ccaggaggac acgcgaaacg cggacuacgc gcguagaggc    300
cacgccccgg cgaccuucgg acggggguuc gauucccccc accuccacca               350
```

<210> SEQ ID NO 92
<211> LENGTH: 349
<212> TYPE: RNA
<213> ORGANISM: Deinococcus radiodurans

<400> SEQUENCE: 92

```
gggggugacc cgguuucgac aggggaacug aaggugaugu ugcgugucga ggugccguug     60
gccucguaaa caaacggcaa agccauuuaa cuggcaacca gaacuacgcu cucgcugcuu    120
aagugagaug acgaccgugc agcccggccu uuggcgucgc ggaagucacu aaaaaagaag    180
gcuagcccag gcgauucucc auagccgacg gcgaaacuuu auggagcuac ggccugcgag    240
aaccugccca cuggugagcg ccggcccgac aaucaaacag ugggauacac acguagacgc    300
acgcuggacg gaccuuugga cggcgguucg acuccgccca ccuccacca                349
```

<210> SEQ ID NO 93
<211> LENGTH: 347
<212> TYPE: RNA
<213> ORGANISM: Deinococcus proteolyticus

<400> SEQUENCE: 93

```
gggggcggaa aggauucgac gggggaacgg aaagcgcugc ugcgugccga ggagccguug     60
gccucguaaa caaacggcaa agccauuaac uggcgaaaau aacuacgcuc ucgcugcuua    120
agugagagca gugaccacgu agccccgccu uuggcgacgu gugaacugag acaaaagaag    180
gcuagcuuag gugagguucc auagccaaaa gugaaaccaa auggaaauaa ggcggacggc    240
agccuguuug cuggcagccc aggcccgaca auuuaagagc agacuacgca cguagaugca    300
cgcuggaugg accuuuggac ggcgguucga uucccgccgc cucacca                  347
```

<210> SEQ ID NO 94
<211> LENGTH: 334
<212> TYPE: RNA
<213> ORGANISM: Thermomicrobium roseum

<400> SEQUENCE: 94

```
cagggccgua ggugcgagga uugcaggucg aggucgccca cgaacucgua aaaggggca      60
ccaaguaacu ggcgagcgcg aacucgcucu ggcugcguaa uucacgcagc cacgucugcc    120
cggacccuuc ccuggugggu ucggagcggg cgccgcaaga ccggggugcc ccuggcccaa    180
gcgccggugc gggccagguc aagcgugauc cggcucggcu gaccgggauc cugucggugg    240
gagccuggca gcgacaguag aacaccgacu aagccuguag cauauccucg gcugaacgcu    300
cuggacgggg guucaacucc cgccagcucc acca                                334
```

<210> SEQ ID NO 95
<211> LENGTH: 353
<212> TYPE: RNA
<213> ORGANISM: Coprothermobacter proteolyticus

<400> SEQUENCE: 95

```
gggggcggaa aggauucgac ggggagucgg agccuugagc ugcaggcagg guuggcugcc     60
acaccuuaaa aagguagca  aggcaaaaau aaaugccgaa ccagaauuug cacuagcugc    120
```
uuaauguaag cagccgcucu ccaaacugag gcugcauaag uuuggaagag cgucaaccca    180
ugcagcggcu cuuaagcagu ggcaccagcu guuuaagggu gaaaagagug gugcugggca    240
gugcgguugg gcuuccuggg cugcacuguc gagacuucac aggagggcua agccuguaga    300
cgcgaaaggu ggcggcucgu cggacgcggg uucgauuccc gccgccucca cca           353

<210> SEQ ID NO 96
<211> LENGTH: 360
<212> TYPE: RNA
<213> ORGANISM: Herpetosiphon aurantiacus

<400> SEQUENCE: 96
gggggcggaa aggauucgac ggggagggcc aaucguaagu ggcaagccga gacgcugagc    60
cucguuaaau cggcaacgcc auuaacuggc aaaaacacuu ccgcgcucc uguagcgcuu     120 gcugccuaau uaaggcaaca cgucucuacu agccucagcc cgaugggcuu guagcggcga    180
cacuuagucg ggucgcuccc cuaguuaugu cuguggggcua ggggcuaaga uuaacaggcu   240
ggucguggcc cgcuuugucu aucggguggu gcaccgauaa gauuuaauca auagacuacg    300
cuuguagaug cuugcgguuu aacuuuuugg acgcggguuc gauucccgcc gccuccacca    360

<210> SEQ ID NO 97
<211> LENGTH: 355
<212> TYPE: RNA
<213> ORGANISM: Thermodesulfobacterium commune

<400> SEQUENCE: 97
gggggcggaa aggauucgac ggggauaggu aggauuaaac agcaggccgu ggucgcaccc    60
aaccacguua aauagggugc aaaaacacaa cugccaacga aucgccuac gcuuuggcag    120 ccuaagcgug cugccacgca ccuuuagacc uugccugugg gucuaaaggu gugugaccua    180
acaggcuuug ggaggcuuaa ucggugggggu uaagccuccc gagauuacau cccaccuggu   240
aggguugcuu ggugccugug acaagcaccc uacgagauuu ucccacaggc uaagccugua    300
gcgguuuaau cugaacuauc uccggacgcg gguucgauuc cgccgccuc cacca          355

<210> SEQ ID NO 98
<211> LENGTH: 329
<212> TYPE: RNA
<213> ORGANISM: Verrucomicrobium spinosum
<220> FEATURE:
<221> NAME/KEY: misc_feature
<222> LOCATION: (1)..(329)
<223> OTHER INFORMATION: n is an unknown base

<400> SEQUENCE: 98
gggnnnnauu uggaauucgc cgaaugcuag aaguggaggc ugcaugccgc ggaugauucg    60
uuggccgcuu uaccaauucg gaucaaacaa cuaaaugcgg acucuaacga gcuugcccuc    120
gccgcuuaau ugacggugac guuccuccag ugaagcucgu gaauuggagg agcgacuacu    180
uacaggcugg ccaaaagagc gggcgaccgg ccccaaggcg agaucuacag gccgcuggau    240
ggacggcauc cuggcaguag gaggcuggac aucgagauca aaunauugcc ugagcaugga    300
gacgcuuuca uaaaggnguu cggacaggg                                     329

<210> SEQ ID NO 99
<211> LENGTH: 351
<212> TYPE: RNA
<213> ORGANISM: Dictyoglomus thermophilum

```
<400> SEQUENCE: 99 ggggcggaa aggauucgac ggggaguaca aggaucaaaa gcugcaagcc gaggugccgu      60
uaccucguaa acaacggca aaaagaagu gccaacacaa auuuagcauu agcugcuuaa     120
uuuagcagcu acgcucuucu aacccgggcu ggcaggguua gaagggguguc auaaugagcc     180 agcugcccu uccgacuccc uaaggaagg gaaagaugua ggggauaggu gcuuacagaa       240 uccgcggga gggagucugu aagugccgaa aaguuaaaac ucccgcuaag cuuguagagg      300
cuuuugauuc uugcucucug gacgcggguu cgauucccgc cgccuccacc a              351

<210> SEQ ID NO 100
<211> LENGTH: 399
<212> TYPE: RNA
<213> ORGANISM: Synechocystis sp. PCC 6803

<400> SEQUENCE: 100
ggggccgcaa ugguuucgac agguuggcga aagcuugccc ugauacagg ucgagaguga     60 gucuccucuc gcaaaucaaa ggcucaaaaa aaaguaacug cgaauaacau cgucagcuuc     120
aaacggguag ccauagcagc cuagucugua aaagcuacau uuucuuguca agaccguuu     180 acuucuuuuc ugacuccguu aaggauuaga gguuaacccc aacggaugcu uguuuggcu      240 cuucucuagu uagcuaaaca aucaagacuc agacuagagc aucccaccau cagggauaau    300 cgauggucc cguccuaggg cuagaaggac uaaaccgug aaugagcgga aaguuaauac       360
ccaguuugga cagcaguuca auucugcucg gcuccacca                            399

<210> SEQ ID NO 101
<211> LENGTH: 385
<212> TYPE: RNA
<213> ORGANISM: Nostoc muscorum

<400> SEQUENCE: 101
ggguccgucg guuucgacag guuggcgaac gcuacucugu gauucagguc gagagugagu    60
cuccucugca aaucaaggcu caaaacaaaa guaaaugcga auaacaucgu uaaauuugcu    120
cguaaggacg cucuaguagc ugccuaaaua gccucuuuca gguucgagcg ucuucgguuu    180
gacuccguua aggacugaag accaaccccc aacggaugcu cuagcaaugu ucucuggguug   240 gcuugcuagc uaagauuuaa ucagagcauc cuacguucgg gauaaugaac gauucccgcc    300
uugaggguca gaaaggcuaa accgugaau gagcgggggg ucauacccca auuggacag      360 caguucgacu cugcucgauc cacca                                          385

<210> SEQ ID NO 102
<211> LENGTH: 393
<212> TYPE: RNA
<213> ORGANISM: Synechococcus PCC 6301

<400> SEQUENCE: 102
ggggcuguaa ugguuucgac guguuggugg auccuucacc ugauucagg ccgagaggga     60 guccacucuc guaaauccag gcucaaccaa aaguaacugc gaacaacauc guuccuuucg    120
cucguaaggc ugcuccugua gcugcuuaaa cgccacaaac uuucggcuc gagcgucuag     180 ucguagacuc cguuaauacg ccuagacuua aaccccaac ggaugcugag uggcggccuc     240
agguccgucc ucucgcuaag caaaaaccug agcaucccgc caacggggau aaucguuggc    300
ucccgcacag ugggucaacc gugcuaagcc ugugaacgag cggaaaguua cuagucaaug    360
cggacagcgg uucgauuccg cucagcucca cca                                393
```

<210> SEQ ID NO 103
<211> LENGTH: 312
<212> TYPE: RNA
<213> ORGANISM: Leptolyngbya sp. (ATCC 27894)

<400> SEQUENCE: 103

| ggcucaaaaa aauagaugca acaacaucg uaccuuucgc ucguaaaacu gcaccuguug | 60 |
| cagcauaaaa caccucuaau ucagguucga gcgcuuaccg ucugacaccg uuaaagauag | 120 |
| uaagcacaac cccaacgguu gcucuagaau uucgccuuug gucggcauuc uagcuaagac | 180 |
| aauaccaaag cauccuauug uccgggacaa aggacaguuc ccgcuucgag gauuagagaa | 240 |
| gcuaaaccug ugaaugauug auagagcuaa uacccaguuu ggacacgggu ucaacucccg | 300 |
| ccagcuccac ca | 312 |

<210> SEQ ID NO 104
<211> LENGTH: 323
<212> TYPE: RNA
<213> ORGANISM: Porphyra purpurea

<400> SEQUENCE: 104

| ggggcugcaa gguucuaca uugugaaaaa acaaauauau gaaaguaaaa cgagcucauu | 60 |
| auuagagcuu uuaguuaaau aaaugcagaa aauaauauua uugcuuuuuc ucgaaaauua | 120 |
| gcuguugcau aaauagucuc aauuuuugua auucgaagug auagacucuu auacacuacg | 180 |
| aauauucugu uagaguugcu cuuaauaaaa gaaaaguaaa aaaauacaaa uucuuauguu | 240 |
| uuuuaccuga auugauucaa uuuaagguua guauuuuug auuuuuacaa uggacguggg | 300 |
| uucaagucc accagcucca cca | 323 |

<210> SEQ ID NO 105
<211> LENGTH: 294
<212> TYPE: RNA
<213> ORGANISM: Cyanophora paradoxa

<400> SEQUENCE: 105

| ggggcuguuu agguuucgac guuuuuucu aauuauguuu guuaagcaag ucgaggauuu | 60 |
| guucuaucuc gaaaaucaag aacucucaaa auuuaaacgc aacuaauauu guacguuuua | 120 |
| accguaaagc agcuuucgcu guuuaauauu uacuuuuaau uuaaaaaccu aauuuuuuua | 180 |
| ggaauuuauu uauuuauugu uuauccugcu uaaugaauua aaaaaagcua uacuugugaa | 240 |
| uaaacgcaua auuuaaaaaaa acggacgugg guucaaaucc caccagcucc acca | 294 |

<210> SEQ ID NO 106
<211> LENGTH: 371
<212> TYPE: RNA
<213> ORGANISM: Odontella sinensis

<400> SEQUENCE: 106

| ggggcugacu ugguuucgac auuuaaaaau uguuacagua ugaugcaggu cgaaguuucu | 60 |
| aaucuucgua aaaaaagaga auuuauaau aaaugcuaau aauuuaauuu cuucuguguu | 120 |
| uaaaaguuua ucaacuaagc aaaauaguuu aaauuuaagu uuugcuguuu aaguuuuaug | 180 |
| cacauuuaau gaucuaguaa auaacuuugu ucgcuauaau uuauauuuau aacuagacuu | 240 |
| uugucuuuuu uauaguuuag aauaacuuua ucauuucaaa cccucguucca ucuaguugaa | 300 |
| cuaaaccugu gaacgaauac uauaauaaaa uuuuuagaug gacgggguu cgacucccau | 360 |
| cagcuccacc a | 371 |

<210> SEQ ID NO 107
<211> LENGTH: 348
<212> TYPE: RNA
<213> ORGANISM: Thls. weiss*

<400> SEQUENCE: 107

| | |
|---|---|
| ggggcugauu ugguuucgac auuuaaaacu ucuuucuaug gucaggguca aaguuuguau | 60 |
| ucuuuguaaa aaauacuaa aauacuaaua aaugcuaaua auauaauacc guuuauuuuu | 120 |
| aaagcaguaa aaacaaaaaa agaagcaaug gcuuuaaauu uugcuguaua guucauuaac | 180 |
| uuagguuauu aaauauuuuu ucauuauaac uggacuuuuu cucaguuuau aguuuagaau | 240 |
| aaauuuaaau uuugcaaaac ucguucgaaa auuuucgggc uaaaccugua aacgcaaaua | 300 |
| cuaagaaauu uuagauggac auggguucaa uucccaucag uuccacca | 348 |

<210> SEQ ID NO 108
<211> LENGTH: 330
<212> TYPE: RNA
<213> ORGANISM: Guillardia theta

<400> SEQUENCE: 108

| | |
|---|---|
| ggggcugauu uggauucgac auauaaauuu gcguguuuca uuaugaagca agucaaguuu | 60 |
| aaugaucuug uaaaaaacau uaaaguacaa auaaaugcaa gcauauagu uucauuuagu | 120 |
| ucaaaacguu uagucucuuu ugcauaagca aaaugguguu auaacuuucu aguagaaau | 180 |
| uggagaaguu uacuaagauu uauauuuacu ccauaauuau uuuaaagaug guaaaaaggu | 240 |
| gauucaucau uuguauguuu cuaaacuuug ugaaagaaua gugggcucca uuuauaauga | 300 |
| acgugggguuc aaaucccacc agcuccacca | 330 |

<210> SEQ ID NO 109
<211> LENGTH: 353
<212> TYPE: RNA
<213> ORGANISM: Mycoplasma hyorhinis

<400> SEQUENCE: 109

| | |
|---|---|
| cauacauaaa aggauauaaa uugcaguggu cuuguaaacc auaagacaau uucuuuacua | 60 |
| agcggaaaag aaaacaaaaa agaagauuau ucauuauuaa ugaaugcuuc aacucaauca | 120 |
| aaucuagcuu uugcauuuua aaaaacuagu agaccaauuu gcuucucacg aauuguaauc | 180 |
| uuuauauuag agaauaguua aaaacugau cacuuuuaa ugaauuuaua gaucacaggc | 240 |
| uuuuuuaauc uuuuuguuau uuuagauaaa gagucuucuu aaaaauaacu aaacuguagg | 300 |
| aauuuauauu uauuaugcg uggacccggg uucaacuccc gccagcucca cca | 353 |

<210> SEQ ID NO 110
<211> LENGTH: 411
<212> TYPE: RNA
<213> ORGANISM: Mycoplasma capricolum

<400> SEQUENCE: 110

| | |
|---|---|
| ggggauguca uggauuugac aggauaucuu uaguacauau aagcaguagu guuguagacu | 60 |
| auaaauacua cuagguuuaa aaaaacgcaa auaaaaacga agaaacuuuu gaaaugccag | 120 |
| cauuuaugau gaauaaugca ucagcuggag caaacuuuau guugcuuaa uaacuacuag | 180 |
| uuuaguuaua guauuucacg aauuauagau auuuuaagcu uuauuuauaa ccguauuacc | 240 |
| caagcuuaau agaauauaug auugcaauaa auauauuuga aaucuaauug caaaugauau | 300 |

-continued uuaaccuuua guuaauuuua guuaaauauu uuaauuagaa aauuaacuaa acuguagaaa 360
guauguauua auauaucuug gacgcgaguu cgauucucgc caucuccacc a 411

<210> SEQ ID NO 111
<211> LENGTH: 381
<212> TYPE: RNA
<213> ORGANISM: Mycoplasma pirum

<400> SEQUENCE: 111
caugaaugau ggacccauag aggcaguggg guaugccccu uauagcucaa gguuuaaauu 60
aaccgacaaa acugacgaaa acguugccgu ugauacaaau uuauuaauca accaacaagc 120
ucaauuuaac uacgcauuug cauaguauaa aaaaauaaau ugugcuacuc auuguaauua 180
gguuacuaaa uuacuuuguu uuauauaguc cuguaacuag uucuagugau gucuauaaac 240
uagaaugaga uuuauagacu uauuuguugg cgguugugcc auagccuaaa ucaacaaaga 300
caauuuauuu augguacuaa acuguagauu cuaugaugaa auuauuugug gaaacggguu 360
cgauucccgc caucuccacc a 381

<210> SEQ ID NO 112
<211> LENGTH: 387
<212> TYPE: RNA
<213> ORGANISM: Mycoplasma pneumoniae

<400> SEQUENCE: 112
ggggauguag agguuuugac auaauguuga aaggaaaaca guugcagugg gguaugcccc 60
uuacagcucu agguauaaua accgacaaaa auaacgacga aguuuuggua gauccaaugu 120
ugaucgcuaa ccaacaagca aguaucaacu acgcuuucgc uuagaacaua cuaaagcuac 180
acgaauugaa ucgccauagu uugguucgug ucacaguuua uggcucgggg uuaacugguu 240
caacuuaauc cuuaaauuau gaacuuaucg uuuacuuguu ugucuuauga ucuaaaguaa 300
gcgagacauu aaaacauaag acuaaacugu agaagcuguu uuaccaaucc uuuauggaaa 360
cggguucgau ucccgucauc uccacca 387

<210> SEQ ID NO 113
<211> LENGTH: 388
<212> TYPE: RNA
<213> ORGANISM: Mycoplasma genitalium

<400> SEQUENCE: 113
ggggauguuu uggguuugac auaaugcuga uagacaaaca guagcauugg gguaugcccc 60
uuacagcgcu agguucaaua accgacaaag aaaauaacga aguguuggua gauccaaauu 120
ugaucauuaa ccaacaagca aguguuaacu uugcuuuugc auaaguagau acuaaagcua 180
cagcugguga auagucauag uuugcuagcu gucauaguuu augacucgag guuaaaucgu 240
ucaauuuaac cuuuaaaaau agaacuuguu guuuccauga uuguuuugug aucaauugga 300
aacaagacaa aaauccacaa aacuaaaaug uagaagcugu uuguuguguc cuuuauggaa 360
acggguucga uucccgucau cuccacca 388

<210> SEQ ID NO 114
<211> LENGTH: 412
<212> TYPE: RNA
<213> ORGANISM: Ureaplasma urealyticum

<400> SEQUENCE: 114

```
ggggauguca cgguuucgac gugacacauu aauuuuuaau ugcaguggggg uuagccccuu      60
aucgcuuucg aggcauuuua aaugcagaaa auaaaaaauc uucugaagua gaauuaaacc     120
cagcguuuau ggcuucagcu acuaaugcaa acuacgcuuu ugcguacuaa uuaguuauua     180
guagaaacgu ucauuaacau aauuacuauu gguggguuuu ugggcuuauu uuacaauagu     240
uuuaaauuua aaauucuuau uguuguuaa auuuaaauag auuuaacaaa uaguuaguua     300
auuuuaaauu uguuuuauua guuauuaacu acacuauuuu uaauaaaacu aaacuguaga     360
uauuauuaau uaugguguugc ggaaagggggu ucgauucccc ucaucuccac ca            412
```

<210> SEQ ID NO 115
<211> LENGTH: 365
<212> TYPE: RNA
<213> ORGANISM: Mycoplasma salivarium

<400> SEQUENCE: 115

```
caggcauucg auucauuaug uugcaguggu uugcaaaccca uaaggcacua ggcuuuuua      60
aacgcaaaag accaaaaaac agaagaucaa gcaguugauc uagcauuuau gaauaauuca     120
caaaugcaau caaaucuagu uuucgcuuag uaaaauuagu caauuuauua uggugcucaa     180
cauaauaaau gguaguauga gcuuaauauc auaugauuuu aguuaauaug auaggauuug     240
uaacuaaacu auguuauaga aauuuguaaa uuauauauau gacauaggaa auuuaauuua     300
cuaaacugua gaugcauaau guugaagaug uguggaccgg gguucaacuc ccgccagcuc     360
cacca                                                                 365
```

<210> SEQ ID NO 116
<211> LENGTH: 363
<212> TYPE: RNA
<213> ORGANISM: Clostridium innocuum

<400> SEQUENCE: 116

```
cggggauaug ucugguacag acugcagucg aguggguuacg uaauaaccaa uuaaauuuaa      60
acggaaaaac uaaauuagcu aaccucuuug guggaaacca gagaauggcu uucgcugcuu     120
aauaaccgau auagguucgc agccgccucu gcaugcuucu uccuugacca uguggauguug    180
cgcguaagac gcaagggaua aggaaucugg uuugccugag aucagauuca cgaaaauucu     240
ucaggcacau ucaucagcgg auguucauga ccugcugaug ucuuaaucuu cauggacuaa     300
acuguagagg ucuguacgug gggcuguuuc uggacaggag uucgauuccc gccgccucca     360
cca                                                                   363
```

<210> SEQ ID NO 117
<211> LENGTH: 359
<212> TYPE: RNA
<213> ORGANISM: Mycoplasma fermentans

<400> SEQUENCE: 117

```
caugcauugg gugauacuaa uaucaguagu uuggcagacu auaaugcauc uaggcuuuau      60
aaucgcagaa gauaaaaaag cagaagaagu uaauauuucu ucacuuauga uugcacaaaa     120
aaugcaauca caaucaaacc uugcuuucgc uuaguuaaaa gugacaagug guuuaaagu     180
ugacauuuuc cuauauauuu uaaaaucggc uuuuaaggag aacaggaguc ugaaagggu     240
ccaaaaaaucu auauuguuug cauuucggua guauagauua auuagaaaug auaaacugua    300
aaaguauug guauugacuu ggugugugga cucggguuca acucccgcca gcuccacca      359
```

<210> SEQ ID NO 118
<211> LENGTH: 320
<212> TYPE: RNA
<213> ORGANISM: Acidobacterium capsulatum

<400> SEQUENCE: 118

| | | |
|---|---|---|
| cggggugac ugcggcaaag aggcaugccg ggggguggc acccguaauc gcucgcaaaa | 60 |
| caauacuugc caacaacaau cuggcacucg cagcuuaauu aaauaaguug ccguccucug | 120 |
| aggcuucgcc uguggccga ggcaggacgu cauacagcag gcugguuccu ucggcugggu | 180 |
| cugggccgcg gggaugagau ccacggacua gcauucugcg uaucuugucg cuucuaagcg | 240 |
| cagagugcga aaccuaaagg aaugcgacug agcauggagu cucuuucug acaccaauuu | 300 |
| cggacgcggg uucgauuccc | 320 |

<210> SEQ ID NO 119
<211> LENGTH: 319
<212> TYPE: RNA
<213> ORGANISM: Fusobacterium mortiferum

<400> SEQUENCE: 119

| | | |
|---|---|---|
| cggggguaug agguuauagg uagcaugcca ggaugaccgc ugugagaggu caacacaucg | 60 |
| uuuagaugga aacagaaaauu acgcuuuagc ugcuuaauua gucagcucac cucugguuc | 120 |
| ucucuucugu aggagaaucc aaccgaggug uuaccaauau acagauuacc uuuagugauu | 180 |
| ucucuaagcu caaagggaca uuuuagagaa uagcuucagu uagcccguc ugcgggagug | 240 |
| auuguugcga aauaaaauag uagacuaagc auuguagaag ccuauggcgc ugguaguuuc | 300 |
| ggacacgggu ucaacuccc | 319 |

<210> SEQ ID NO 120
<211> LENGTH: 329
<212> TYPE: RNA
<213> ORGANISM: Fibrobacter succinogenes

<400> SEQUENCE: 120

| | | |
|---|---|---|
| cagggguacc gaaguguuag uugcaagucg aggucucaga cgagggcuac ucguuaaaaa | 60 |
| gucugaaaaa aaauaagugc ugacgaaaac uacgcacucg cugccuaauu aacggcaacg | 120 |
| ccgggccuca uuccgcuccc aucgggugu acguccggac gcaauauggg auagggaagu | 180 |
| gucaugccug ggggcaucuc ccgagauuuu cuaggcuggu caaacuccgc gccgaccuuc | 240 |
| uugggcgugg auaagacgag aucuuaaauu cgaagggaac acuuguagga acguacaugg | 300 |
| acgugauuuu ggacagggu ucaacuccc | 329 |

<210> SEQ ID NO 121
<211> LENGTH: 300
<212> TYPE: RNA
<213> ORGANISM: Artificial
<220> FEATURE:
<223> OTHER INFORMATION: isolated from rumenal fluid

<400> SEQUENCE: 121

| | | |
|---|---|---|
| acgcccuugu cucagacgag ggcacucguu aaaagucug aaaagaauaa cugcagaacc | 60 |
| uguagcuaug gcugcuuaau uuaagggcaa cccuuggauc cgccuccauc ccgaagggu | 120 |
| ggcauccgag ucgcaaaaucg ggauaggaug gaucuuggca acgaggagua caauccgaaau | 180 |
| uugucgcugc uggcugaagc aucgccguuc cucuuuggu guggcaaggc aagauuaaau | 240 |
| ucagaggaua agcguguagu agcgagugag uagguguuuu uggacgcggg uucaagcccc | 300 |

```
<210> SEQ ID NO 122
<211> LENGTH: 330
<212> TYPE: RNA
<213> ORGANISM: Pirellula staleyi

<400> SEQUENCE: 122
ccggauagcc ugaagcgaau acggcgugcc gugguugauc agauggccac guaaaaagcu     60
gaucacaaac uuaacugccg agagcaaucu cgcacuugcu gccuaacuaa acgguagcuu    120
ccgacugagg gcuuuagccg gagaggccca aaaguugguc accaaauccg gaccgccucg    180
ugccaugauc gaaacgcacg aggucaaaaa aguuucgauc uagugcaggg guagccagc     240 agcuaggcga caaacugugc aaaaaucaaa uuuucugcua cgcacguaga uguguucgug    300
aaaaugucuc gggacgggggg uucaacuccc                                    330

<210> SEQ ID NO 123
<211> LENGTH: 329
<212> TYPE: RNA
<213> ORGANISM: Planctomyces maris

<400> SEQUENCE: 123
cugguucacc guauguuaag guggcggugc cgugguugau caguuggcca cguaaaaagc     60
ugaucacaau cuaauugcaa acaagcaauu uucaauggcu gcuuaauaaa agcaaccccg    120
gcuuaggaau cucugucuga ggaguccgac agcuggcuac aaaaucagac gguaucaga    180 ucaaugccg cuccgucuga uacgagauuc guggguggacu gguuccaac aggcucuguu     240 uaucgugccc gaagaaacga gacucaaacg auaaaauaug caccguagag gcuuuagcug    300 agggguucaca ggacgcgggu ucaacuccc                                     329

<210> SEQ ID NO 124
<211> LENGTH: 318
<212> TYPE: RNA
<213> ORGANISM: Artificial
<220> FEATURE:
<223> OTHER INFORMATION: isolated from sludge

<400> SEQUENCE: 124
cagggaacca ggagguguga gaugcaugcc ggagacgcug uccgcuccgu uaucaagcag     60
cacaacaaaa uaauugcaaa caacaauuac uccuuagcag cguaagcagc uaacguucaa    120
ccucuccgga ccgccgggag gggauuuggg cgucgaaaca gcgcggacgc uccggauagg    180
acgcccauaa uauccggcua agaccauggg ucuggcucuc gcgggucuga uugucuucca    240
ccgcgcgggc cgcgaucaaa gacaacuaag caugaagguu cuugcauggc cguucuuug     300 gacgcgggu cgauuccc                                                   318

<210> SEQ ID NO 125
<211> LENGTH: 407
<212> TYPE: RNA
<213> ORGANISM: Porphyromonas gingivalis

<400> SEQUENCE: 125
ggggcugacc ggcuuugaca gcgugaugaa gcgguaugua agcauguagu gcgugggugg     60
cuugcacuau aaucucagac aucaaaaguu uaauuggcga aaauaacuac gcucucgcug    120
cguaaucgaa gaauaguaga uuagacgcuu caucgccgcc aaaguggcag cgacgagaca    180
ucgcccgagc agcuuuuucc cgaaguagcu cgaugguccg gugcugacaa aucgggaaacc   240 gcuacaggau gcuuccugcc uggguucaga ucgaacggaa gauaaggauc gugcauuggg    300
```

```
ucguuucagc cuccgcucgc ucacgaaaau uccaacugaa acuaaacaug uagaaagcau      360
auugauucca uguuuggacg agggulcaau ucccuccagc uccacca                   407

<210> SEQ ID NO 126
<211> LENGTH: 379
<212> TYPE: RNA
<213> ORGANISM: Bacteroides thetaiotaomicron

<400> SEQUENCE: 126
cagcgggcag aaaugguagg uaagcaugca gugggucggu aauuccacu uaaaucucag       60 uuaucaaaac uuuaucuggc gaaacuaauu acgcucuugc ugcuuaaucg aaucacagua     120
gauuagcuua auccaggcac uaggugccca ggagagacau cacucggaag cuguugcucc     180
gaagcauucc gguucagugg ugcaguaaca ucggggauag ucagaagcgg ccucgcguuu     240
uugaugaaac uuuagaggau aaggcaggaa uugauggcuu ugguucugcu ccugcacgaa     300
aauuuaggca aagauaagca guagaaagc uuaugauuuc cucguuugga cgagggulca      360 acucccgcca gcuccacca                                                  379

<210> SEQ ID NO 127
<211> LENGTH: 404
<212> TYPE: RNA
<213> ORGANISM: Chlorobium tepidum

<400> SEQUENCE: 127
ggggaugaca ggcuaucgac aggauaggug ugagaugucg uugcacuccg aguuucagca      60
uggacggacu cguuaaacaa gucuaugac caauagaugc agacgauuau ucguaugcaa     120
uggcugccug auuagcacaa guuaauucag aagccaucgu ccugcgguga augcgcuuac     180
ucugaagccg ccggauggca uaacccgcgc uugagccuac ggguucgcgc aaguaagcuc     240
cguacauuca ugcccgaggg ggugugcggg uaaccaaucg ggauaagggg acgaacgcug     300
cuggcggugu aaucggacca cgaaaaacca accaccagag augaguguggg uaacugcauc     360 gagcagaguc cuggacgcgg guucaagucc cgccaucucc acca                     404

<210> SEQ ID NO 128
<211> LENGTH: 372
<212> TYPE: RNA
<213> ORGANISM: Chlorobium limicola

<400> SEQUENCE: 128
caggauacgu gugagauguc guugcacucc gaguuucagc auggacggac ucguuaaaca      60
agucuaugua ccauuagaug cagacgauua uucguaugca auggcugccu gauuagcaca     120
aguuaacuca gacgccaucg uccugcggug aaugcgcuua cucugaagcc gccggauggc     180
auaacccgcg cuugagccua cgggulcgcg caaguaagcu ccguacauuc augcccgagg     240
ggcugugcgg guaauuucuc gggauaaggg gacgaacgcu gcuggcggug uaaucggccc     300
acgaaaaccc aaucaccaga gaugaguguug ugacugcau cgagcagugu uuggacgcg     360 gguucaacuc cc                                                         372

<210> SEQ ID NO 129
<211> LENGTH: 420
<212> TYPE: RNA
<213> ORGANISM: Chlamydia trachomatis
```

<400> SEQUENCE: 129

```
ggggguguaa agguuucgac uuagaaauga agcguuaauu gcaugcggag ggcguuggcu      60
ggccuccuaa aaagccgaca aaacaauaaa ugccgaaccu aaggcugaau gcgaaauuau     120
cagcuucgcu gaucucgaag aucuaagagu agcugcuuaa uuagcaaagu guuaccuaa      180
auacggguga cccggguguuc gcgagcucca ccagagguuu cgaaacacc gucauguauc     240
ugguuagaac uuagguccuu uaauucucga ggaaaugagu uugaaauuua augagagucg     300
uuagucucua aggggguuuc uagcugagga gacauaacgu auaguaccua ggaacuaagc     360
auguagaggu uagcggggag uuuacuaagg acgagaguuc gacucucucc accuccacca    420
```

<210> SEQ ID NO 130
<211> LENGTH: 421
<212> TYPE: RNA
<213> ORGANISM: Chlamydia mousep*

<400> SEQUENCE: 130

```
ggggguguaa agguuucgac uuagaaauga agcguuaauu gcaugcggag ggcguuggcu      60
ggccuccuaa aaagccgaca aaacaauaaa ugccgaaccu aaggcugaau gcgaaauuau     120
cagcuucgcu gaucuuaaug aucuaagagu ugcugcuuaa uuagcaaagu guuaccuaa      180
guacuggguaa cccggguguuc gcgagcucca ccagagguuu cgaaacgcc gucauuuauc    240
ugguuagaau uagggccuuu uaacucucaa gggaacuaau uugaauuuua augagagucg     300
uuggucucua agagguuuc uagcugagga gauauaacgu aaaauauucu agaaacuaag     360
caugagagg uuagcgggga guuuacuaag gacgagaguu cgaaucucuc caccuccacc     420
a                                                                    421
```

<210> SEQ ID NO 131
<211> LENGTH: 426
<212> TYPE: RNA
<213> ORGANISM: Chlamydia pneumoniae

<400> SEQUENCE: 131

```
gggggugunau agguuucgac uugaaaauga aguguuaauu gcaugcggag ggcguuggcu      60
ggccuccuaa aaagccaaca aaacaauaaa ugccgaaccu aaggcugaau gcgaaauuau     120
uagcuuguuu gacucaguag aggaaagacu agcugcuuaa uuagcaaaag uuguuagcua     180
gauaaucucu agguaacccg guacugcga gcuccaccag aggcuugcaa aauaccguca      240
uuuaucuggu uggaacuuac uuucucuaau ucucaaggaa guucguucga gauuuuugag     300
aguucauggc ugcuauagag gcuucuagcu aagggagucc aauguaaaca auucuagaag     360
auaagcaugu agagguuagc agggaguuug ucaaggacga gaguucgagu cucuccaccu    420
ccacca                                                               426
```

<210> SEQ ID NO 132
<211> LENGTH: 328
<212> TYPE: RNA
<213> ORGANISM: Micrococcus luteus

<400> SEQUENCE: 132

```
cggugugugu cgcgucggga gaagcgggcc gaggaugcag agucaucucg ucaaacgcuc      60
ucugcaaacc aauaagugcc gaauccaagc gcacugacuu cgcucucgcu gccugaucag    120
ugaucgaguc cgucaccccg aggucgcugu cgccucggau cguggcguca gcuagauagc    180
cacugggcgu cacccucgcc gggggucgug acgccgacau caauccggcu ggguccgggu    240
```

```
uggccgcccg ucugcgggac ggccaggacc gagcaacacc cacagcagac ugcgcccgga    300
gaagaccugg caacaccuca ucggacgc                                       328

<210> SEQ ID NO 133
<211> LENGTH: 368
<212> TYPE: RNA
<213> ORGANISM: Mycobacterium leprae

<400> SEQUENCE: 133
ggggcugaaa gguucgacu ucgcgcaucg aaucaaggga agcgugccgg ugcaggcaag     60
agaccaccgu aagcgucguu gcagcaauau aagcgccgau ucauaugagc gcgacuaugc    120
ucucgcugcc uaagcgaugg cuagucuguc agaccgggaa cgcccucguc ccggagccug    180
gcaucagcua gagggaucua ccaugggguu cggucgcggg acucgucggg acaccaaccg    240
cgacugggau cgucauccug gcuaguucgc gugaucagga gauccgagua gaggcauagc    300
gaacuacgca cggagaagcc uugagggaaa ugccguagga cccggguucg auucccggca    360
gcuccacc                                                             368

<210> SEQ ID NO 134
<211> LENGTH: 360
<212> TYPE: RNA
<213> ORGANISM: Mycobacterium tuberculosis

<400> SEQUENCE: 134
ggggcugaac gguucgacu ucgcgcaucg aaucaaggga agcgugccgg ugcaggcaag     60
agaccaccgu aagcgucguu gcgaccaaau aagcgccgau ucaucagc gcgacuacgc     120 ucucgcugcc uaagcgacgg cuagucuguc agaccgggaa cgcccucggc ccggaccccug  180 gcaucagcua ccaccgauga guccggucgc gggacuccuc gggacaacca cagcgacugg   240
gaucgucauc ucggcuaguu cgcgugaccg ggagauccga gcagaggcau agcgaacugc   300
gcacggagaa gccuugaggg aaugccguag dacccgagguu cgauucccgg cagcuccacc  360

<210> SEQ ID NO 135
<211> LENGTH: 373
<212> TYPE: RNA
<213> ORGANISM: Mycobacterium avium

<400> SEQUENCE: 135
ggggcugaaa gguucgacu ucgcgcaucg aaucaaggga agcgugccgg ugcaggcaac     60
ugaccaccgu aagcgucguu gcagauagau aagcgccgau ucaucagc gcgacuacgc     120 ucucgcugcc uaagcgacag cuagucgagg gaucgucagc ccgggaacgc ccucgacccg    180
gagccuggcg ucagcuagag ggauccaccg augaguucgg ucgcgggacu caucgggaca    240
ccaacagcga cugggaucgu cauccuggcu guucgcgug accaggagau ccgaguagag     300
gcauagcgaa cugcgcacgg agaagccuug agggaaugcc guaggacccg gguucgauuc    360
ccggcagcuc cac                                                       373

<210> SEQ ID NO 136
<211> LENGTH: 331
<212> TYPE: RNA
<213> ORGANISM: Corynebacterium xerosis

<400> SEQUENCE: 136
cuucguacau ugagccaggg gaagcgugcc ggugaaggcu ggagaccacc gcaagcgucg     60
cagcaaccaa uuaagcgccg agaacucuca gcgcgacuac gcccucgcug ccuaagcagc    120
```

```
gaccgcgugu cugucagacc ggguaggccu cugauccgga cccuggcauc guuuaguggg       180
gcucgcucgc cgacuugguc gcaagggucg gcggggacac ucacuugcga cugggcccgu       240
cauccgguca uguucgacug aaccggaggg ccgagcagag accacgcgcg aacugcgcac       300
ggagaagccc uggcgaggug acggaggacc c                                      331

<210> SEQ ID NO 137
<211> LENGTH: 354
<212> TYPE: RNA
<213> ORGANISM: Treponema pallidum

<400> SEQUENCE: 137
ggggaugacu agguuucgac uagggaugug ggguguugcg cugcaggugg agugucgauc        60
uccugauucg gcgccuuuau aacugccaau ucgacaguu ucgacuacgc gcucgccgcg        120
uaaucgcggg ccuguguuug cgcugcucug agcgaacaua ucgcccgac gccaaacgga        180 gcuugcucuu acguugugca cggcggacgu agggggacuu uugucugugc uaagacucug       240
gcgcgugcgg ugcaggccua gcagaguccg acaaacgcag uacgcaccgc uaaaccugua       300
ggcgcgcagc acucgcucuu uaggacgggg guucgauucc ccccaucucc acca             354

<210> SEQ ID NO 138
<211> LENGTH: 362
<212> TYPE: RNA
<213> ORGANISM: Borrelia burgdorferi

<400> SEQUENCE: 138
ggggauguuu uggauuugac ugaaaauguu aauauuguaa guugcaggca gagggaaucu        60
cuuaaaacuu cuaaaauaaa ugcaaaaaau aauaacuuua caagcucaaa ucuuguaaug       120
gcugcuuaag uuagcagagg guuuguuga auuggcuuu gagguucacu uauacucuuu        180
ucgacaucaa agcuugcuua aaaauguuuu caaguugauu uuuagggacu uuuauacuug       240
agagcaauuu gguggguuugc uaguauuucc aaaccauauu gcuuaauaaa auacuagaua      300
agcuuguaga agcuuauagu auuauuuuua ggacgcgggu ucaauucccg ccaucuccac       360
ca                                                                     362

<210> SEQ ID NO 139
<211> LENGTH: 364
<212> TYPE: RNA
<213> ORGANISM: Borrelia garinii

<400> SEQUENCE: 139
ggggcugauu cuggauucga cugaaaaugc gaauauugua aguugcaggc agagggaauc        60
ucuuaaaacu ucuaaaauaa augcaaaaaa uaauaacuuu acaagcucaa accuuguaau       120
ggcugcuuaa guuagcaggg aguuucguug aauuggcuu ugagguucac uuauacucuu       180
uucgauaucg aagcuugcuu aaaaauguuu ucaaguuaau uuuagggac uuuuguacuu       240 gagagcaauu uggcgguuug cuaguauuuc caaaccauau ugcuuaagua aaaugcuaga      300
uaagcuugua gaagcuuaua auauuguuuu uaggacgcgg guucaauucc cgccaucucc       360
acca                                                                   364

<210> SEQ ID NO 140
<211> LENGTH: 363
<212> TYPE: RNA
<213> ORGANISM: Borrelia afzelii
```

-continued

<400> SEQUENCE: 140

```
ggggcugauu cuggauucga cugaaaaugc uaauauugua aguugcaagc agagggaauc     60
ucuuaaaacu ucuaaaauaa augcaaaaaa uaauaacuuu acaaguucaa accuuguaau    120
ggcugcuuaa guuagcagag aguuuuguug aauuuggcuu ugagauucac uuauacucuu    180
uuagacaucg aagcuugcuu aaaaauguuu ucaaguugau uuuuagggac uuuuauacuu    240
gagagcaauu uggcgguuug cuaguauuuc caaaccauau ugcuuaguaa aauacuagau    300
aagcuuguag aagcuuauag uauuguuuuu aggacgcggg uucaauuccc gccaucucca    360
cca                                                                  363
```

<210> SEQ ID NO 141
<211> LENGTH: 363
<212> TYPE: RNA
<213> ORGANISM: Borrelia crocidurae

<400> SEQUENCE: 141

```
ggggcugauu cuggauucga cuaagaacuu uaguagcaua aauggcaagc agagugaauc     60
ucuuaaaacu ucuuuaauaa augcaaaaaa uaauaacuuu acaaguucag aucuuguaau    120
ggcugcuuaa uuuagcagag aguuuuguug gauuuugcuu ugagguucaa cuuauacucu    180
uuaagacauc aaaguaugcc uaaaaauguu ucaaguugau uuuuagggac cuuuaaacuu    240
gagaguaauu ugguguuug cuuguuuucc aagccuuauu gcuuuuucua aaaauuagcu    300
aagcuuguag auauuuauga uauuauuuuu uggacgcggg uucaauuccc gccaucucca    360
cca                                                                  363
```

<210> SEQ ID NO 142
<211> LENGTH: 365
<212> TYPE: RNA
<213> ORGANISM: Borrelia hermsii

<400> SEQUENCE: 142

```
ggggcugauu cuggauucga cuaaaaacuu uaguagcaua aauugcaagc agagggaauc     60
ucuuaaaacu ucuuuaauaa augcaagaaa uaauaacuuu acaaguucaa aucuuguaau    120
ggcugcuuaa auuagcagag aguucugcug gauuuugcuu ugagguucag cuuauacucu    180
uuuaagacau caaagcuugc uuaaaaauau uucaaguuga uuuuuaggga cuuuuaaauu    240
ugagaguaau uuggcgguuu gcuaguuuuu ccaaaccuua uuacuuaaag aaaacacuag    300
cuaagcuugu agauauuuau gauauuauuu uuaggacgcg gguucaauuc ccgccaucuc    360
cacca                                                                365
```

<210> SEQ ID NO 143
<211> LENGTH: 330
<212> TYPE: RNA
<213> ORGANISM: Alcaligenes faecalis

<400> SEQUENCE: 143

```
cgggggucaa gaagcagcac agggcguguc gagcaccagu acgcucguaa auccacugga     60
aaacuauaaa cgccaacgac gagcguuucg cucuagccgc uuaaggcugg gccacugcac    120
uaauuugucu uuggguuagg uagggcaacc uacagcagug uuauuuacaa agaaucgaau    180
cggucugcgc cacgaagucc gguucuaaaa cuuaguggau cgccaaggaa aggccuguca    240
auuggcauag uccaagguua aaacuuaaaa uuaauugacu acacauguag aacugucugu    300
ggacggcuug cggacggggg uucgauuccc                                     330
```

<210> SEQ ID NO 144
<211> LENGTH: 340
<212> TYPE: RNA
<213> ORGANISM: Alcaligenes eutrophus

<400> SEQUENCE: 144 cgugggiuuac aaagcagugg agggcauacc gaggacccgu caccucguua aucaauggga    60
augcaauaac ugcuaacgac gaacguuacg cacuggccgc uuaauugcgg ccguccucgc    120
acuggcucgc ugacgggcua gggucgcaag accacgcgag gucauuuacg ucagauaagc    180
uccggaaggg ucacgaagcc ggggacgaaa accuagugac ucgccgucgu agagcguguu    240
cguccgcgau gcgccgguua aucaaauga cagaacuaag uauguagaac ucucuggga    300 gggcuuacgg acgcggguuc gauucccgcc ggcuccacca    340

<210> SEQ ID NO 145
<211> LENGTH: 326
<212> TYPE: RNA
<213> ORGANISM: Ralstonia pickettii

<400> SEQUENCE: 145 cgggggiuugc gaagcagcgg agggcauacc gaggacccgu caccucguua aucaauggga    60
augcaauaac ugcuaacgac gaacguuacg cacuggcagc cuaagggccg ccguccucgc    120
acuggcucgc ugacgggcua gggucgcaag accagcgagg ucauuuacgu cagauaagcu    180
uuaggugagu cacggcccua gagacgaaaa cuuagugaau cgccgucgua gagcguguuc    240
guccgcgaug cggcgguuaa aucaaaugac agaacuaagu auguagaacu cucuguggag    300
ggcuugcgga cgcgggguucg auccc    326

<210> SEQ ID NO 146
<211> LENGTH: 363
<212> TYPE: RNA
<213> ORGANISM: Neisseria gonorrhoeae

<400> SEQUENCE: 146
gggggcgacc uugguuucga cggggguugc gaagcagaug cgggcauacc ggggucucag    60
auccccguaa aacacugaau ucaaauaguc gcaaacgacg aaacuuacgc uuuagccgcu    120
uaaggcuagc cguugcagca gucgucaauu gggcuguguc gugaaagcca ccgcaacguc    180
aucuuacauu gacugguuuc cagccggguu acuuggcagg aaauaagacu uaagguaacu    240
gguuuccaaa aggccuguug gucggcauga uggaaauaag auuuucaaau agacacaacu    300
aaguauguag aacgcuuugu agaggacuuu cggacggggg uucgauuccc cccgccucca    360
cca    363

<210> SEQ ID NO 147
<211> LENGTH: 363
<212> TYPE: RNA
<213> ORGANISM: Neisseria meningitidis

<400> SEQUENCE: 147
gggggcgacc uugguuucga cggggguugc gaagcagaug cgggcauacc ggggucucag    60
auccccguaa aacacugaau ucaaauaguc gcaaacgacg aaacuuacgc uuuagccgcu    120
uaaggcuagc cguugcagca gucgucaauu gggcuguguc gcgaaagcca ccgcaacguc    180
aucuuacauu gacugguuuc cugccggguu auuggcagg aaaugagauu uaagguaacu    240
gguuuccaaa aggccuguug gucggcauga uggaaauaag auuuucaaau agacacaacu    300

| | |
|---|---:|
| aaguauguag aacgcuuugu agaggacuuu cggacggggg uucgauuccc cccgccucca | 360 |
| cca | 363 |

<210> SEQ ID NO 148
<211> LENGTH: 333
<212> TYPE: RNA
<213> ORGANISM: Chromobacterium violaceum

<400> SEQUENCE: 148

| | |
|---|---:|
| cgggggguugc gaagcagaug agggcauacc gggauuucag ucaccccgua aaacgcugaa | 60 |
| uuuauauagu cgcaaacgac gaaacuuacg cucuggcagc cuaacggccg gccagacacu | 120 |
| acaacgguuc gcagaugggc cggggcguc aaacccugu agugcacuc uacaucugcu | 180 |
| agugcuguuc cgguuacuu gguucagugc gaaauaauag guaacucgcc aaagccagc | 240 |
| cuguccgucg gcguggcaga gguuaaaucc aaaugacacg acuaaguaug uagaacucac | 300 |
| uguagaggac uuucggacgc ggguucaacu ccc | 333 |

<210> SEQ ID NO 149
<211> LENGTH: 330
<212> TYPE: RNA
<213> ORGANISM: Nitrosomonas cryotolerans

<400> SEQUENCE: 149

| | |
|---|---:|
| cgugggguugc aaagcagcgc agggcauacc gaggaccaga auaccucgua aaucaucug | 60 |
| gaaaaaaaua gucgcaaacg acgaaaacua cgcuuuagcc gcuuaauacg gcuagccucu | 120 |
| gcaccgaugg gccuuaacgu cgggucuggc aacagacagc agagucauua gcaaggaucg | 180 |
| cguucuguag ggucacuuua cagaacguua acaauaggu gacucgccug ccaucagccc | 240 |
| gccagcuggc gguugucagg uuaaauuaaa gagcauggcu aaguauguag aacugucugu | 300 |
| agaggacuug cggacgcggg uucaacuccc | 330 |

<210> SEQ ID NO 150
<211> LENGTH: 331
<212> TYPE: RNA
<213> ORGANISM: Methylobacillus glycogenes

<400> SEQUENCE: 150

| | |
|---|---:|
| cgggggguugc aaagcagcgc agggcauacc gaggccuagu caccucguaa auaaacuaga | 60 |
| acaaguauag ucgcaaacga cgaaacuuac gcucuagccg cuuaauccg gcuggacgcu | 120 |
| gcaccgaagg gccucucggu cggguggggu aacccacagc agcgucauua agagaggauc | 180 |
| gugcgauauu ggguuacuua auacguauu aaauccaagg uaacucgccu gcuguuugcu | 240 |
| ugcucguugg ugagcaucag guuaaaucaa acaacacagc uaaguaugua gaacugucug | 300 |
| uggagggcuu gcggacgggg guucgauucc c | 331 |

<210> SEQ ID NO 151
<211> LENGTH: 375
<212> TYPE: RNA
<213> ORGANISM: Pseudomonas testosteroni

<400> SEQUENCE: 151

| | |
|---|---:|
| ggggccgauu cuggauucga cgugggucg ggaccggugc ggugcaugu gagcuugagu | 60 |
| gacgcucgua aaucuccauu caaaaaacua acugcaaacg acgaacguuu cgcacucgcc | 120 |
| gcuuaauccg gugagccuug caacagcacg cuaguggcu gggcaagggg guagcaauac | 180 |
| cucccggcug caagggaauu uucauuagcu ggcuggauac cggcuucuu gguauuuggc | 240 |

-continued

```
gagauuuuag gaagcuggcu acccaagcag cgugugccug cggggguuugg guggcgagau    300 uuaaaacaga gcacuaaaca uguagaucug uccggcgaag gcuuacggac gcggguucaa    360
uucccgccgg cucca                                                     375
```

<210> SEQ ID NO 152
<211> LENGTH: 353
<212> TYPE: RNA
<213> ORGANISM: Variovorax paradoxus

<400> SEQUENCE: 152

```
cgugggguucg gagucgcagc ggggcauguc gagcugaaug cgcucguaaa acagauucaa     60
acaaacuaac ugcaaacgac gaacguuucg cacucgcugc uuaauugcca gugagccuug    120
caacaguugg ccgaugggcu gggcaagggg gucuggagca auccugaccu cccggcugca    180
aggauaacua caugggcugg cuccgauccg gguaccuugg gucggggcga gaaaauaggg    240
uacuggcguc cgguuuagcg ugugacugcg cgacuccgga agcgagacuc aaaacagauc    300
acuaaacaug uagaacugcg cgaugaaggc uugcggacgg ggguucaacu ccc           353
```

<210> SEQ ID NO 153
<211> LENGTH: 345
<212> TYPE: RNA
<213> ORGANISM: Hydrogenophaga palleroni

<400> SEQUENCE: 153

```
cgugggguucg gacgcgcagc agggcauguc gagguucugu caccucguaa aucagcagaa     60
aaaaaccaac ugcaaacgac gaacguuucg cacucgccgc uuaaacaccg gugagccuug    120
caacagcagg ccgaugggcu gggcaagggg gucgcaagac cucccggcug caagguaauu    180
uacaucggcu gguucugcgu cggcaccuu ggcgcaggau gagauucaag gaugcuggcu    240
ucccguuuag cgugccacug cgcgacucgg gcggcgagac ccaaaucaga cggcuacaca    300
uguagaacug cucgaaaaag gcuugcggac gggggguucaa cuccc                   345
```

<210> SEQ ID NO 154
<211> LENGTH: 387
<212> TYPE: RNA
<213> ORGANISM: Bordetella pertussis

<400> SEQUENCE: 154

```
ggggccgauc cggauucgac gugggucaug aaacagcuca gggcaugccg agcaccagua     60
agcucguuaa uccacuggaa cacuacaaac gccaacgacg agcgucucgc ucucgccgcu    120
uaagcgguga gccgcugcac ugaucugucc uugggucagg cgggggaagg caacuuccca    180
gggggcaacc ccgaaccgca gcagcgacau ucacaaggaa ucggccaccg cuggggucac    240
acggcguugg uuuaaauuac gugaaucgcc cugguccggc ccgucgaucg gcuaagucca    300
ggguuaaauc caaauagauc gacuaagcau guagaacugg uugcggaggg cuugcggacg    360
gggguucaau uccccccggc uccacca                                        387
```

<210> SEQ ID NO 155
<211> LENGTH: 323
<212> TYPE: RNA
<213> ORGANISM: Legionella pneumophila

<400> SEQUENCE: 155

```
cgugggguugc aaaaccggaa gugcaugccg agaaggagau cucucguaaa uaagacucaa     60
uuaaauauaa augcaaacga ugaaaacuuu gcuggugggg aagcuaucgc ugccuaauaa    120
```

```
gcacuuuagu uaaaccauca cuguguacug gccaauaaac ccaguauccc guucgaccga    180
gcccgcuuau cgguaucgaa ucaacgguca uaagagauaa gcuagcgucc uaaucuaucc    240
cggguuaugg cgcgaaacuc agggaaucgc uguguaucau ccugcccguc ggaggagcca    300
caguuaaauu caaaagacaa ggc                                          323

<210> SEQ ID NO 156
<211> LENGTH: 315
<212> TYPE: RNA
<213> ORGANISM: Chromatium vinosum

<400> SEQUENCE: 156 cguggguuegc gaaaccuaag gugcaugccg aggugcgguu gaccucguaa aacccuccgc    60
aaacuuauag uugccaacga cgacaacuac gcucucgcug cuuaauccca gcggccucu    120 gaccgucacu ugccuguggg cggcggauuc caggggauaac cucacacagg aucguggga    180 cgggaguccg gaccgauccc acuaaaaccu aacggaaucg ccgacugauc gcccugcccu    240
ucgggcggca gaaggcuaaa aacaauagag ugggcuaagc auguaggacc gagggcagag    300
ggcuugcgga cgcgg                                                    315

<210> SEQ ID NO 157
<211> LENGTH: 318
<212> TYPE: RNA
<213> ORGANISM: Dichelobacter nodosus

<400> SEQUENCE: 157
cucgaggugc augucgagaa ugagagaauc ucguuaaaua cuuucaaaac uuauaguugc    60
aaacgacgac aacuacgcuu uagcggcuua auucccgcuu cgcuuaccu agauuugucu    120 gugggguuac cguaagcgac auuaacacag aaucgcuggu uaacgcgucc gcuguuaauc    180
gguuaaauua agcggaaucg cuuguaaaau gccugagcgu uggcuguuua ugaguuaaac    240
cuaauuaacu gcucuaaaca uguaguacca aaaguuaagg auucgcggac ggggguucaa    300
auccccccgc cuccacca                                                 318

<210> SEQ ID NO 158
<211> LENGTH: 354
<212> TYPE: RNA
<213> ORGANISM: Pseudomonas aeruginosa

<400> SEQUENCE: 158
ggggccgauu aggauucgac gccgguaaca aaacuugagg ggcaugccga gcugguagca    60
gaacucguaa auucgcugcu gcaaacuuau aguugccaac gacgacaacu acgcucuagc    120
ugcuuaaugc ggcuagacag ucgcuagggg augccguaa acccgaaacg acugucagau    180
agaacaggau cgccgccaag uucgcuguag acguaacggc uaaaacucau acagcucgcu    240
ccaagcaccc ugccacucgg gcggcgcgga guuaacucag uagagcuggc uaagcaugua    300
gaaccgauag cggagagcug gcggacgggg guucaaaucc ccccggcucc acca          354

<210> SEQ ID NO 159
<211> LENGTH: 350
<212> TYPE: RNA
<213> ORGANISM: Pseudomonas fluorescens

<400> SEQUENCE: 159
cgccgguugc gaaccuuuag gugcaugccg aguuggguaac agaacucgua aauccacugu    60
ugcaacuuuc uuaguugcca augacgaaac cuacgggaa uacgcucucg cugcguaagc    120
```

```
agccuuagcc cuucccuccu gguaccuucg gguccagcaa ucaucagggg augucuguaa    180
acccaaagug auugucauau agaacagaau cgccgugcag uacguugugg acgaagcggc    240
uaaaacuuac acaacucgcc caaagcaccc ugcccgucgg gucgcugagg guuaacuuaa    300
uagacacggc uacgcaugua guaccgacag cagaguacug gcggacgggg              350

<210> SEQ ID NO 160
<211> LENGTH: 323
<212> TYPE: RNA
<213> ORGANISM: Marinobacter hydrocarbonoclasticus

<400> SEQUENCE: 160
cgccggugac gaacccuugg gugcaugccg agauggcagc gaaucucgua aauccaaagc    60
ugcaacguaa uagucgcaaa cgacgaaaac uacgcacugg cggcguaagc cguuccaguc   120
guccuggcug aggcgccuau aacucaguag caacauccca ggacgucauc gcuuauaggc   180
ugcuccguuc accagagcuc acugguguuc ggcuagagau aaaagagcucg ccucuugcac   240 ccugaccuuc gggucgcuug agguuaaauc aauagaagga cacuaagcau guagaccuca   300
aggccuagug cuggcggacg cgg                                           323

<210> SEQ ID NO 161
<211> LENGTH: 355
<212> TYPE: RNA
<213> ORGANISM: Shewanella putrefaciens

<400> SEQUENCE: 161
gggggcgauu cuggauucga caggauucac gaaacccugg gagcaugccg aggggcgguu    60
ggccucguaa aaagccgcaa aguuauaguu gcaaacgacg auaacuacgc ucuagccgcu   120
uaaugccgcu agccaucuac cacacgcuuu gcacaugggc aguggauuug auggucaucu   180
cacaucgugc uagcgaggga acccugucug ggggugaacc gcgaaacagu accggacuca   240
ccguguggga uccugucuuu cggaguucaa acgguuaaac aauagaaaga cuaagcaugu   300
agcgccuugg auguagguuu ucuggacgcg gguucaaguc ccgccgccuc cacca        355

<210> SEQ ID NO 162
<211> LENGTH: 314
<212> TYPE: RNA
<213> ORGANISM: Pseudoalteromonas haloplanktis

<400> SEQUENCE: 162
cggaauucaa gaagcccgag gugcaugucg aggugcgguu ugccucguaa aaaagccgca    60
auuuaaagua aucgcaaacg acgauaacua cucucuagca gcuuaggcug gcuagcgcuc   120
cuuccaugua uucuugugga cuggauuuug gagugucacc cuaacaccug aucgcgacgg   180
aaacccuggc cggggguugaa gcguuaaaac uaagcggccu cgccuuuauc uaccguguuu   240
guccgggauu uaaagguuaa uuaaaugaca auacuaaaca guaguaccg acggucgagg    300 cuuuucggac gggg                                                     314

<210> SEQ ID NO 163
<211> LENGTH: 316
<212> TYPE: RNA
<213> ORGANISM: Aeromonas salmonicida

<400> SEQUENCE: 163
caagauucac gaaacccaag gugcaugccg aggugcggua ggccucguua acaaaccgca    60
aaaaaauagu cgcaaacgac gaaaacuacg cacuagcagc uuaauaaccu gcauagagcc   120
```

```
cuucuacccu agcuugccug uguccuaggg aaucggaagg ucauccuuca caggaucgug    180
uggaaguccu gcucggggcg gaagcauuaa aaccaaucga gcuagucaau ucgggcgug    240 ucucuccgca gcggguuggc gaauguaaag agugacuaag caugaguac cgaggaugua    300 guaauuuugg acgggg                                                   316

<210> SEQ ID NO 164
<211> LENGTH: 363
<212> TYPE: RNA
<213> ORGANISM: Salmonella typhimurium

<400> SEQUENCE: 164
ggggcugauu cuggauucga cgggauuugc gaaacccaag gugcaugccg aggggcgguu    60
ggccucguaa aaagccgcaa aaaauaguc gcaaacgacg aaaccuacgc uuuagcagcu    120
uaauaaccug cuuagagccc ucucuccccua gccuccgcuc uuaggacggg gaucaagaga    180
ggucaaaccc aaaagagauc gcgcggaugc ccugccuggg guugaagcgu uaaaacgaau    240
caggcuaguc ugguaguggc guguccgucc gcaggugcca ggcgaaugua aagacugacu    300
aagcauguag uaccgaggau guaggaauuu cggacgcggg uucaacuccc gccagcucca    360
cca                                                                 363

<210> SEQ ID NO 165
<211> LENGTH: 363
<212> TYPE: RNA
<213> ORGANISM: Escherichia coli

<400> SEQUENCE: 165
ggggcugauu cuggauucga cgggauuugc gaaacccaag gugcaugccg aggggcgguu    60
ggccucguaa aagccgcaa aaaauagucg caaacgacga aaacuacgcu uuagcagcuu    120
aauaaccugc uuagagcccu cucucccuag ccuccgcucu uaggacgggg aucaagagag    180
gucaaaccca aaagagaucg cguggaagcc cugccugggg uugaagcguu aaaacuuaau    240
caggcuaguu uguuaguggc guguccgucc gcagcuggca agcgaaugua aagacugacu    300
aagcauguag uaccgaggau guaggaauuu cggacgcggg uucaacuccc gccagcucca    360
cca                                                                 363

<210> SEQ ID NO 166
<211> LENGTH: 364
<212> TYPE: RNA
<213> ORGANISM: Yersinia pestis

<400> SEQUENCE: 166
ggggcugauu cuggauucga cgggauucgc gaaacccaag gugcaugccg aggugcggug    60
gccucguaaa aaccgcaaa aaaauaguu gcaaacgacg aaaacuacgc acuagcagcu    120
uaauaaccug cuuagagccc ucucuccccua gccuccgcuc uuaggacggg gaucaagaga    180
ggucaaaccu aaaagagcuc gugugggaac cuugccuggg guggaagcau uaaaacuaau    240
caggauaguu ugucaguagc guguccaucc gcagcuggcc ggcgaaugua augauuggac    300 uaagcauagua gugccgacgg uguaguaauu ucggacgggg guucaaaucc ccccagcucc    360
acca                                                                364

<210> SEQ ID NO 167
<211> LENGTH: 367
<212> TYPE: RNA
<213> ORGANISM: Vibrio cholerae
```

-continued

```
<400> SEQUENCE: 167 gggcugauu caggauucga cgggaauuuu gcagucugag gugcaugccg aggugcggua      60
ggccucguua acaaaccgca aaaaaauagu cgcaaacgac gaaaacuacg cacuagcagc    120
uuaauacccu gcucagagcc cuccucccu agcuccgcu guaagacgg ggaaaucagg       180 aaggucaaac caaaucaagc uggcguggau uccccaccu gagggaugaa gcgcagagauc   240 uaauucaggu uagccauucg uuagcguguc gguucgcagg cgguggugaa auuaaagauc    300
gacuaagcau guaguaccaa agaugaaugg uuuucggacg ggguucaac ucccccagc     360 uccacca                                                              367

<210> SEQ ID NO 168
<211> LENGTH: 366
<212> TYPE: RNA
<213> ORGANISM: Haemophilus influenzae

<400> SEQUENCE: 168 gggcugauu cuggauucga cgggauuagc gaagcccaag gugcacgucg aggugcggua     60
ggccucguaa auaaaccgca aaaaauacu cgcaaacgac gaacaauacg cuuuagcagc    120
uuaauaaccu gcauuuagcc uucgcgcucc agcuccgcu cguaagacgg ggauaacgcg    180
gagucaaacc aaaacgagau cguguggaag ccaccguuug aggaucgaag cacuaaauug    240
aaucaaacua gcuuaaguuu agcgugucug ccgcaugcu uaagugaaau uaagacgag    300 acuaaacgug uaguacugaa gguagaguaa uuucggacgg gguucaacu cccccagcu     360 ccacca                                                              366

<210> SEQ ID NO 169
<211> LENGTH: 366
<212> TYPE: RNA
<213> ORGANISM: Haemophilus actinomycetemcomitans

<400> SEQUENCE: 169 gggcugauu cuggauucga cgggauuagc gaagcccgaa gugcacgucg aggugcggua     60
ggccucguaa auaaaccgca aaaaauagu cgcaaacgac gaacaauacg cuuuagcagc    120
uuaauaaccu gccuuuagcc uucgcucccc agcuccgcu cguaagacgg ggauaaagcg    180
gagucaaacc aaaacgagau cguguggaag ccaccguuug aggaucgaag cauuaaauua    240
aaucaaagua gcuuauugu cgcguguccg ucagcaggau uaagugaauu uaagaccgg    300 acuaaacgug uagugcuaac ggcagaggaa uuucggacgg gguucaacu cccccagcu     360 ccacca                                                              366

<210> SEQ ID NO 170
<211> LENGTH: 354
<212> TYPE: RNA
<213> ORGANISM: Desulfovibrio desulfuricans

<400> SEQUENCE: 170 cgggacgug aagccguag cggcaggucg aggcgccgcu ggccucguaa aaagcggcac     60
aaaaguaauu gccaacaacg auuacgacua cgcuuacgcu gccaauaac agcgaggcaa   120 ugaccguuua acggucgcgc cgaucagggc caugccugau aacccugauu cacuuaucag    180
gcuggcgaaa accggcucuc gccggguuu uucgcgagga guuuaccggc gggauuccug    240
cguugugccu ggcaggggc caacagcgcg gugaaauaca uacuugaccu aaaccuguag    300
augcuucgug uggaauguuc ucggacgggg guucaaaucc ccccggcucc acca         354
```

<210> SEQ ID NO 171
<211> LENGTH: 366
<212> TYPE: RNA
<213> ORGANISM: Myxococcus xanthus

<400> SEQUENCE: 171

| | | | | | |
|---|---|---|---|---|---|
| gggggcggaa | aggauucgac | gggggcauug | aaguucgaga | cgcgugccga | gcuugucagg | 60 |
| uagcucguaa | auucaacccg | gcaaagacac | aaaagccaac | gacaacguug | agcucgcgcu | 120 |
| ggcugccuaa | aaacagccca | uagugcgcgg | ucccccccgcc | cucggccugu | ggggguuggga | 180 |
| cagaccguca | uaaugcaggc | uggcugccga | gggugccugg | acccgaggug | gcagaucuu | 240 |
| cccaggaccg | gcucugagua | ucccguccgu | gggagccuca | gggacguagc | aaaucgcgga | 300 |
| cuacgcacgu | agggucgaag | agcggacggc | uuucggacgc | ggguucgauu | cccgccgccu | 360 |
| ccacca | | | | | | 366 |

<210> SEQ ID NO 172
<211> LENGTH: 346
<212> TYPE: RNA
<213> ORGANISM: Bdellovibrio bacteriovirus

<400> SEQUENCE: 172

| | | | | | |
|---|---|---|---|---|---|
| gggggcggaa | aggauucgac | gggggugcug | aagcauaagg | agcauaccgg | ggcggaugag | 60 |
| gaccucguua | aaaacgucca | cuuuguaauu | ggcaacgauu | acgcacuugc | agcuuaauua | 120 |
| agcagcacga | ucaaccuugu | ggugguuccg | cacuuggauu | gaucgucauu | uagggaccuc | 180 |
| ggcguguugg | guuuucucca | gcagacaugc | uuaaauuuac | uggggagag | gucuuaggga | 240 |
| uuuugucugu | ggaagcccga | ggaccaaucu | aaaacacuga | cuaaguaugu | agcgccuuau | 300 |
| cguggaucau | uugcggacgg | ggguucgauu | cccgccgccu | ccacca | | 346 |

<210> SEQ ID NO 173
<211> LENGTH: 386
<212> TYPE: RNA
<213> ORGANISM: Helicobacter pylori

<400> SEQUENCE: 173

| | | | | | |
|---|---|---|---|---|---|
| ggggcugacu | uggauuucga | cagauuucuu | gucgcacaga | uagcaugcca | agcgcugcuu | 60 |
| guaaaacagc | aacaaaaaua | acuguaaaca | acacagauua | cgcuccagcu | uacgcuaaag | 120 |
| cugcgugagu | uaaucuccuu | uuggagcugg | acgauuaga | auuucuagcg | uuuuaaucgc | 180 |
| uccauaaccu | uaagcuagac | gcuuuuaaaa | gguggucgc | cuuuuaaacu | aagaaacaag | 240 |
| aacucuugaa | acuaucucaa | gguuuagaa | aguuggacca | gagcuaguuu | uaaggcuaaa | 300 |
| aaaccaacca | auuuucuaag | cauuguagaa | guuuguguuu | agggcaagau | uuuuggacug | 360 |
| ggguucgauu | ccccacagcu | ccacca | | | | 386 |

<210> SEQ ID NO 174
<211> LENGTH: 359
<212> TYPE: RNA
<213> ORGANISM: Campylobacter jejuni

<400> SEQUENCE: 174

| | | | | | |
|---|---|---|---|---|---|
| gggagcgacu | uggcuucgac | aggaguaagu | cugcuuagau | ggcaugucgc | uuugggcaaa | 60 |
| gcguaaaaag | cccaaauaaa | auuaaacgca | aacaacguua | aauucgcucc | ugcuuacgcu | 120 |
| aaagcugcgu | aaguucaguu | gagccugaaa | uuuaagucau | acuaucuagc | uuaauuuucg | 180 |
| gucauuuuug | auagugцagc | cuugcguuug | acaagcguug | aggugaaaua | aagucuuagc | 240 |

-continued

```
cuugcuuuug aguuuuggaa gaugagcgaa guagggugaa guagucaucu uugcuaagca        300
uguagagguc uuuguggggau uauuuuugga caggggguucg auuccccucg cuuccacca       359

<210> SEQ ID NO 175
<211> LENGTH: 355
<212> TYPE: RNA
<213> ORGANISM: Sulfurospirillum deleyianum

<400> SEQUENCE: 175
caggaguagu uuuagcuuau ggcugcaugu cgggagugag ggucuuccgu uacacaaccu         60
ucaaacaaua acugcuaaca acaguaacua ucguccugcu uacgcgcuag cugcguaagu       120
uuaacaaaua auggacugcu cuccccuuug augcuaucuu aggaggucuu ggagaguauc       180
auagauuuga uagcuauauu acaugaacgc cuuuacaugu aaugaaguua aaggcucguu       240
uucguaguuu ucugauuguu guacgaagca aaauuaaaca cuaucaacaa uaucuaagca       300
uguagacguc auagguggcu auuuuuggac uggggguucaa cucccgccag cucca           355
```